(12) United States Patent
Liu

(10) Patent No.: US 11,236,088 B2
(45) Date of Patent: Feb. 1, 2022

(54) HETEROCYCLIC COMPOUNDS AND THEIR APPLICATION IN MEDICINE

(71) Applicant: KIND PHARMACEUTICAL, Hangzhou (CN)

(72) Inventor: Dong Liu, Hangzhou (CN)

(73) Assignee: KIND PHARMACEUTICAL, Hangzhou (CN)

( * ) Notice: Subject to any disclaimer, the term of this patent is extended or adjusted under 35 U.S.C. 154(b) by 25 days.

(21) Appl. No.: 16/762,478

(22) PCT Filed: Nov. 13, 2018

(86) PCT No.: PCT/CN2018/115142
§ 371 (c)(1),
(2) Date: May 7, 2020

(87) PCT Pub. No.: WO2019/096106
PCT Pub. Date: May 23, 2019

(65) Prior Publication Data
US 2021/0179609 A1 Jun. 17, 2021

(30) Foreign Application Priority Data
Nov. 14, 2017 (CN) .......................... 201711123800.2

(51) Int. Cl.
*C07D 471/04* (2006.01)
(52) U.S. Cl.
CPC ................... *C07D 471/04* (2013.01)
(58) Field of Classification Search
CPC .................................................. C07D 471/04
USPC ................................................... 514/210.18
See application file for complete search history.

(56) References Cited

FOREIGN PATENT DOCUMENTS

| WO | WO 2014/106848 A1 | 7/2014 |
|---|---|---|
| WO | WO 2014/135843 A1 | 9/2014 |
| WO | WO 2014/141292 A2 | 9/2014 |
| WO | WO 2014/151899 A1 | 9/2014 |
| WO | WO 2014/165723 A2 | 10/2014 |
| WO | WO 2016/097072 A1 | 6/2016 |
| WO | WO 2016/202161 A1 | 12/2016 |
| WO | WO 2017/174757 A1 | 10/2017 |
| WO | WO 2018/077630 A1 | 5/2018 |

OTHER PUBLICATIONS

Miller et al., Tetrahedron (2002), 58(30), 6061-6067.*
International Search Report and Written Opinion of the International Searching Authority issued for International Application No. PCT/CN2018/115142 dated Feb. 12, 2019.
Bogen et al., "Depeptidization efforts on P3-P'2 α-ketoamide inhibitors of HCV NS3-4A serine protease: Effect on HCV replicon activity", Bioorganic & Medicinal Chemistry Letters, 2006, 16: 1621-1627.
Itoh et al., "A General Palladium-Catalyzed Coupling of Aryl Bromides/Triflates and Thiols", Organic Letters, 2004, 6(24): 4587-4590.
Myers et al., "A New Family of Small Molecules To Probe the Reactivation of Mutant p53", J. Am. Chem. Soc., 2005, 127: 6152-6153.
Schiemenz, "Diphenyl-p-Bromophenylphosphine", Organic Syntheses, Coll. vol. 5, p. 496 (1973); vol. 49, p. 66 (1969).
Weir et al., "AZD9496: An Oral Estrogen Receptor Inhibitor That Blocks the Growth of ER-Positive and ESR1-Mutant Breast Tumors in Preclinical Models", Cancer Research, 2016, 76(11): 3307-3318.

* cited by examiner

*Primary Examiner* — Niloofar Rahmani
(74) *Attorney, Agent, or Firm* — Bozicevic, Field & Francis LLP; James S. Keddie

(57) ABSTRACT

This invention relates to heterocyclic compounds and their use in medicine. In particular, the present invention discloses heterocyclic compound of formula I, or an isotopically labeled compound thereof, or an optical isomer thereof, a geometric isomer thereof, a tautomer thereof or a mixture of various isomers, or a pharmaceutically acceptable salt thereof, or a prodrug thereof. The invention also relates to the use of these compounds in medicine.

18 Claims, 3 Drawing Sheets

| Example No. | Western Blot Immunoblotting (MCF-7 cells) | Western Blot Immunoblotting (MCF-7/TAMR1 cells) |
|---|---|---|
| Example 15 |  |  |
| Example 16 |  |  |
| Example 17 |  |  |
| Example 18 |  |  |

HETEROCYCLIC COMPOUNDS AND THEIR APPLICATION IN MEDICINE

CROSS-REFERENCE TO RELATED APPLICATION

This application is a National Stage of International Patent Application No. PCT/CN2018/115142, filed on Nov. 13, 2018, which claims priority to Chinese Patent Application No. 201711123800.2, filed on Nov. 14, 2017, both of which are incorporated herein by reference in their entirety.

TECHNICAL FIELD

The present disclosure belongs to the field of medicine and relates to a compound useful for treatment of diseases such as breast cancer associated with estrogen receptor, its preparation and its application in medicine.

BACKGROUND

Estrogen comprises estrone, estradiol and the like, the most of which is secreted by ovary, and the minority of which is secreted by liver, adrenal cortex and breast. As the main sex hormone of female animals, estrogen promotes maturity of female accessory organs and appearance of secondary sexual characteristics, and maintains a normal sexual desire and a reproductive function. It works as below. Estrogen diffuses into nucleus and specifically binds to estrogen receptor (ER) to form a complex and the activated estrogen receptor quickly forms a homo or heterodimer, which binds a DNA enhancer. Including an estrogen response element ERE and the like, and gather other transcription factors to form a transcription initiation complex to induce transcription. In addition, the activated estrogen receptors can also gather transcriptional co-factors and bind to activating protein 1 (AP-1) located in the promoter region of target genes, thereby regulating gene transcription activity.

The estrogen receptor includes two structurally similar proteins: ERα and ERβ, and their functional regions comprises: a. ligand independent activation function 1 (AF-1), the transcriptional activity of which does not depend on the presence of a ligand (estrogen), and can be phosphorylated by MAPK kinase to enhance its activity; b. a DNA binding domain (DBD), which contains a double zinc finger structure and which binding to specific DNA is regulated synergistically for achieving the purpose of transcription of a target gene; c. a hinge domain located between a DNA binding domain and a ligand binding domain (LBD); d. a ligand binding domain, which functions as binding to estrogen, receptor dimerization, nuclear localization, and binding to transcription cofactors (activated or unactivated). In addition, the ligand binding domain also comprises another ligand-dependent transcription activation function 2, AF 2, which is unlike AF-1, and whose function dependent on estrogen. AF 2 when binding to different estrogens will induce different conformations and combine corresponding co-activator or co-inhibitor, to initiate or close gene transcription.

Although estrogen plays an important role in normal physiological activities, too much or too little estrogen activity can induce related diseases, including breast cancer, endometrial cancer, cardiovascular disease, and osteoporosis. Among them, breast cancer caused by high expression of estrogen receptor accounts for 66% of all breast cancers. At present, treatment of such tumors is mainly through selective Estrogen Receptor Modulators (SERMs) drugs, including tamoxifen, raloxifene and so on. These drugs work as below. The drugs bind to the ligand-binding domain of estrogen receptor to form dimer complexes, change conformation of estrogen receptor, and exclude estrogen and transcriptional activators from binding to it, thereby blocking estrogen receptor growth promotion in breast cancer cells. Although SERM drugs have a good effect on estrogen-overexpressing breast cancer, more and more studies showed that there are polymorphisms in the biological effects of estrogen receptors, which are specifically manifested as estrogen receptors binding to SERM in different tissues may gather different transcriptional activators or transcriptional inhibitors, as "antagonist" or "agonist", and cause serious side effects such as osteoporosis. In addition, resistance caused by mutations in estrogen receptor genes also severely limits the use of SERM drugs.

Selective Estrogen Receptor Degraders (SERDs) bind to estrogen receptor to induce its conformational change, which leads to the exposure of hydrophobic residues to the molecular surface, and thus recruits E3 ubiquitin ligase. Ubiquitin ligase is degraded by modifying the estrogen receptor ubiquitination and eventually directing it to proteasome. By degrading estrogen receptor, we can more completely block estrogen signaling pathway and prevent it from recruiting transcriptional activators as "agonists." In addition, SERD can degrade mutant estrogen receptors, thereby preventing the emergence of resistance.

There are already some patent documents on SERD, such as WO2014165723, WO2014151899, WO2014141292, WO2014135843, WO2014106848, and WO2016202161.

Although SERD shows compelling broad prospects for the treatment of diseases associated with ER such as breast cancer, to date, there is no small molecule drugs for SERD that can be taken orally in the market. Therefore, it is still necessary to find new small molecule drugs for SERD so that patients can have more options in the future.

SUMMARY

1. Compounds of the Present Disclosure

It is one of objects of the present disclosure to provide a novel SERD.

Accordingly, one aspect of the present disclosure provides a compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof, wherein the compound of Formula I is as follows

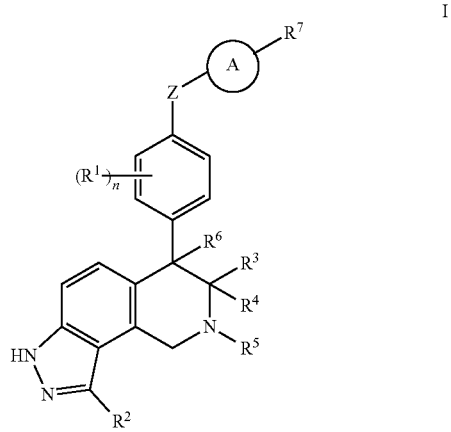

in which $R^1$ and $R^2$ are each independently selected from the group consisting of hydrogen, halo, cyano, C1 to C4 alkyl and substituted alkyl;

n is 1, 2, 3, or 4;

$R^3$, $R^4$, $R^6$ are each independently selected from the group consisting of hydrogen, C1 to C6 alkyl and substituted alkyl, aryl and heteroaryl;

$R^5$ is selected from the group consisting of C1 to C6 alkyl and substituted alkyl, aryl and heteroaryl;

$R^7$ is selected from the group consisting of C1 to C6 alkyl and substituted alkyl, C2 to C6 alkenyl and substituted alkenyl, C2 to C6 alkynyl and substituted alkynyl, and acyl having 1 to 6 carbon atoms;

Z is selected from the group consisting of O, S, $NR^8$, C(=O), C)($R^9$)($R^{10}$, wherein $R^8$, $R^9$ and $R^{10}$ are each independently selected from hydrogen, C1 to C6 alkyl and substituted alkyl;

A is a saturated four to six membered ring, which is a full carbocyclic ring or a heterocyclic ring containing one oxygen atom, one nitrogen atom, or two nitrogen atoms as ring atoms.

In some preferred embodiments of the present invention, in Formula I, $R^6$ is selected from the group consisting of hydrogen, C1 to C4 alkyl and substituted C1 to C4 alkyl. In some preferred embodiments of the present invention, in Formula I, $R^6$ is selected from the group consisting of hydrogen, C1 to C4 alkyl and halogen substituted C1 to C4 alkyl. In some preferred embodiments of the present invention, in Formula I, $R^6$ is hydrogen, methyl or fluorine substituted methyl. In some preferred embodiments of the present invention, in Formula I, $R^6$ is hydrogen or methyl. In some particularly preferred embodiments of the present invention, in Formula I, $R^6$ is hydrogen. In some particularly preferred embodiments of the present invention, in Formula I, $R^6$ is methyl.

In some preferred embodiments of the present invention, in Formula I, $R^5$ is selected from the group consisting of C1 to C4 alkyl and substituted C1 to C4 alkyl. In some preferred embodiments of the present invention, in Formula I, $R^5$ is selected from the group consisting of C1 to C4 alkyl and halogen substituted C1 to C4 alkyl. In some preferred embodiments of the present invention, in Formula I, $R^5$ is methyl or fluorine substituted methyl. In some particularly preferred embodiments of the present invention, in Formula I, $R^5$ is methyl.

In some preferred embodiments of the present invention, in Formula I, $R^3$ and $R^4$ are each independently selected from the group consisting of hydrogen, C1 to C4 alkyl, and substituted C1 to C4 alkyl. In some preferred embodiments of the present invention, in Formula I, preferably $R^3$ and $R^4$ are each independently selected from the group consisting of hydrogen, C1 to C4 alkyl and halogen-substituted C1 to C4 alkyl. In some preferred embodiments of the present invention, in Formula I, preferably $R^3$ and $R^4$ are each independently selected from the group consisting of hydrogen and C1 to C4 alkyl groups. In some particularly preferred embodiments of the present invention, in Formula I, one of $R^3$ and $R^4$ is hydrogen and the other is C1 to C4 alkyl. In some particularly preferred embodiments of the present invention, in Formula I, one of $R^3$ and $R^4$ is hydrogen and the other is isobutyl or cyclopropylmethyl.

In some preferred embodiments of the invention, in Formula I, $R^7$ is selected from the group consisting of C1 to C6 alkyl, substituted C1 to C6 alkyl, and acyl having 1 to 6 carbon atoms. In some preferred embodiments of the invention, in Formula I, $R^7$ is selected from the group consisting of C1 to C6 alkyl, halogen substituted C1 to C6 alkyl, and acyl having 1 to 5 carbon atoms. In some preferred embodiments of the invention, in Formula I, $R^7$ is selected from the group consisting of C1 to C5 alkyl, halogen substituted C1 to C5 alkyl, and acyl having 1 to 4 carbon atoms. In some particularly preferred embodiments of the present invention, in Formula I, $R^7$ is selected from the group consisting of ethyl, propyl, butyl, pentyl, formyl, acetyl, propanoyl, butyryl, and fluoro or difluoro propyl and fluoro or difluoro butyl including any isomers of these groups. In some particularly preferred embodiments of the invention, in Formula I, $R^7$ is propyl (or any isomer thereof). In some particularly preferred embodiments of the invention, in Formula I, $R^7$ is butyl (or any isomer thereof). In some particularly preferred embodiments of the invention, in Formula I, $R^7$ is pentyl (or any isomer thereof). In some particularly preferred embodiments of the present invention, in Formula I, $R^7$ is formyl (or any isomer thereof). In some particularly preferred embodiments of the present invention, in Formula I, $R^7$ is acetyl (or any isomer thereof). In some particularly preferred embodiments of the invention, in Formula I, $R^7$ is propanoyl (or any isomer thereof). In some particularly preferred embodiments of the invention, in Formula I, $R^7$ is butyryl (or any isomer thereof). In some particularly preferred embodiments of the present invention, in Formula I, $R^7$ is fluoro or difluoro propyl (or any isomer thereof). In some particularly preferred embodiments of the present invention, in Formula I, $R^7$ is fluoro or difluoro butyl (or any isomer thereof).

In some preferred embodiments of the invention, in Formula I, $R^2$ is selected from the group consisting of hydrogen, C1 to C4 alkyl, substituted C1 to C4 alkyl, and halogen. In some preferred embodiments of the invention, in Formula I, $R^2$ is selected from the group consisting of hydrogen, C1 to C4 alkyl, halogen-substituted C1 to C4 alkyl, and halogen. In some preferred embodiments of the invention, in Formula I, $R^2$ is selected from the group consisting of hydrogen, C1 to C2 alkyl, F or Cl substituted C1 to C2 alkyl, F and Cl. In some preferred embodiments of the invention, in Formula I, $R^2$ is hydrogen or methyl or fluorine-substituted methyl or F or Cl. In some preferred embodiments of the invention, in Formula I, $R^2$ is hydrogen or methyl. In some particularly preferred embodiments of the invention, in Formula I, $R^2$ is hydrogen. In some particularly preferred embodiments of the invention, in Formula I, $R^2$ is methyl. In some particularly preferred embodiments of the invention, in Formula I, $R^2$ is F. In some particularly preferred embodiments of the invention, in Formula I, $R^2$ is Cl.

In some preferred embodiments of the invention, in Formula I, $R^1$ is selected from the group consisting of hydrogen, C1 to C4 alkyl, substituted C1 to C4 alkyl, and halogen. In some preferred embodiments of the invention, in Formula I, $R^1$ is selected from the group consisting of hydrogen, C1 to C4 alkyl, halogen-substituted C1 to C4 alkyl, and halogen. In some preferred embodiments of the invention, in Formula I, $R^1$ is selected from the group consisting of hydrogen, C1 to C2 alkyl, F or Cl substituted C1 to C2 alkyl, F and Cl. In some preferred embodiments of the invention, in Formula I, $R^1$ is hydrogen, methyl, F or Cl substituted methyl, F or Cl. In some preferred embodiments of the invention, in Formula I, $R^1$ is hydrogen or methyl or F or Cl. In some particularly preferred embodiments of the invention, in Formula I, $R^1$ is hydrogen. In some particularly preferred embodiments of the invention, in Formula I, $R^1$ is methyl. In some particularly preferred embodiments of the invention, in Formula I, $R^1$ is F. In some particularly preferred embodiments of the invention, in Formula I, $R^1$ is Cl.

In some preferred embodiments of the present invention, in Formula I, the number n of $R^1$ is 1 or 2 or 3. In some preferred embodiments of the present invention, in Formula I, the number n of $R^1$ is 1 or 2.

In some particularly preferred embodiments of the present invention, in Formula I, $R^8$, $R^9$, and $R^{10}$ are each independently selected from the group consisting of hydrogen, C1 to C6 alkyl, and substituted C1 to C6 alkyl. In some particularly preferred embodiments of the present invention, in Formula I, $R^8$, $R^9$, and $R^{10}$ are each independently selected from the group consisting of hydrogen, C1 to C4 alkyl, and substituted C1 to C4 alkyl. In some particularly preferred embodiments of the present invention, in Formula I, $R^8$, $R^9$, and $R^{10}$ are each independently selected from the group consisting of hydrogen, C1 to C4 alkyl, and halogen-substituted C1 to C4 alkyl. In some particularly preferred embodiments of the present invention, in Formula I, $R^8$, $R^9$ and $R^{10}$ are each independently selected from the group consisting of hydrogen, methyl, ethyl, F or Cl substituted methyl. In some particularly preferred embodiments of the invention, in Formula I, $R^8$, $R^9$ and $R^{10}$ are each independently selected from the group consisting of hydrogen and methyl. In some particularly preferred embodiments of the present invention, in Formula I, $R^8$, $R^9$ and $R^{10}$ are all hydrogen.

In some preferred embodiments of the present invention, in Formula I, Z is selected from the group consisting of O, S, NH, C(=O) and $CH_2$. In some preferred embodiments of the present invention, in Formula I, Z is selected from the group consisting of O, S and NH. In some particularly preferred embodiments of the invention, in Formula I, Z is O. In some particularly preferred embodiments of the invention, in Formula I, Z is S.

In some preferred embodiments of the present invention, in Formula I, A is a saturated four-membered carbocyclic ring, a saturated five-membered carbocyclic ring or a saturated six-membered carbocyclic ring, or is a four-membered heterocyclic ring, a five-membered heterocyclic ring, or a six-membered heterocyclic ring containing one oxygen atom, one nitrogen atom or two nitrogen atoms as ring atoms. In some particularly preferred embodiments of the present invention, in Formula I, A is a saturated four-membered carbocyclic ring or a four-membered heterocyclic ring containing one oxygen atom, one nitrogen atom, or two nitrogen atoms as ring atoms. In some particularly preferred embodiments of the present invention, in Formula I, A is a saturated five-membered carbocyclic ring or a five-membered heterocyclic ring containing one oxygen atom, one nitrogen atom, or two nitrogen atoms as ring atoms. In some particularly preferred embodiments of the present invention, in Formula I, A is a saturated six-membered carbocyclic ring or a six-membered heterocyclic ring containing one oxygen atom, one nitrogen atom, or two nitrogen atoms as ring atoms. In some particularly preferred embodiments of the present invention, in Formula I, A is an azetidine ring.

In a preferred embodiment of the present invention, in Formula I, the substituted alkyl refers to alkyl substituted with halogen, more preferably alkyl substituted with F or Cl, and the most preferably alkyl substituted with one or two or three F atoms.

In the various preferred embodiments above, the preference for each substituent may be combined with one another, and various combinations thereof are within the scope of the invention.

In the most preferred embodiments of the invention, the compound of Formula I is each specific compound shown in Examples 1 to 34 herein.

For simplicity, as used herein, "a compound as shown by Formula I" or "a compound of Formula I" or "a compound of the invention" or "a compound according to the invention" also encompasses any optical isomer, geometric isomer, tautomer or a mixture of various isomers of the compound of Formula I.

The term "an optical isomer" refers that when a compound has one or more chiral centers, each chiral center may have an R configuration or an S configuration, and the various isomers thus constituted are known as an optical isomer. Optical isomers comprise all diastereomers, enantiomers, meso forms, racemates or mixtures thereof. For example, optical isomers can be separated by a chiral chromatography or by chiral synthesis.

The term "geometric isomer" refers that when a double bond is present in a compound, the compound may exist as a cis isomer, a trans isomer, an E isomer, and a Z isomer. A geometric isomer comprises cis isomers, trans isomer, E isomer, Z isomer, or a mixture thereof.

The term "tautomer" refers to an isomer that is formed by rapid movement of an atom at two positions in a single molecule. It will be understood by those skilled in the art that tautomers can be mutually transformed, and in a certain state, may coexist by reaching an equilibrium state. As used herein, "a compound as shown by Formula I" also encompasses any tautomer of the compound of formula I.

Unless otherwise indicated, reference to "a compound as shown by Formula I" or "a compound of Formula I" or "a compound of the invention" or "a compound according to the invention" herein also encompasses isotopically-labeled compounds obtained by replacing any atom of the compound with its isotopic atom.

The invention comprises all pharmaceutically acceptable isotopically-labeled compounds of Formula I wherein one or more atoms are replaced by atoms having the same atomic number but different atomic mass or mass number than those normally found in nature.

Examples of isotopes suitable for inclusion in the compounds of the invention include isotopes of hydrogen, such as $^2H$ (D) and $^3H$ (T), of carbon, such as $^{11}C$, $^{13}C$ and $^{14}C$, of chlorine, such as $^{36}Cl$, of fluorine, such as $^{18}F$, of iodine, such as $^{123}I$ and $^{125}I$, of nitrogen, such as $^{13}N$ and $^{15}N$, of oxygen, such as $^{15}O$, $^{17}O$ and $^{18}O$, and of sulphur, such as $^{35}S$.

Certain isotopically-labelled compounds of formula (I), for example, those incorporating a radioactive isotope, are useful in drug and/or substrate tissue distribution studies. The radioactive isotopes deuterium, i.e. $^2H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Certain compounds of the invention may exist in unsolvated form as well as solvated forms, including hydrated forms. In general, the compounds of formula I, whether present in solvated form or in unsolvated form, are included within the scope of the invention.

Certain compounds of the invention may exist in different crystalline or amorphous forms, and the compounds of Formula I present in any form, are included within the scope of the invention.

To avoid ambiguity, the definitions of the terms used herein are given below. Unless otherwise stated, the meanings of the terms used herein are as follows.

The term "hydroxy" refers to —OH.

The term "halogen" or "halo" refers to —F, —Cl, —Br, or —I.

The term "amino" refers to —NH$_2$.

The term "cyano" refers to —CN.

The term "carboxy" refers to —C(═O)OH.

The term "acyl" refers to —C(═O)R, in which R is H or alkyl or substituted alkyl.

The term "substituted" means that one or more (preferably 1 to 5, more preferably 1 to 3) hydrogen atoms in a group are independently replaced by a corresponding number of substituents.

The term "independently" means that when the number of substituents is more than one, these substituents may be the same or different.

The term "optional" or "optionally" means that the event described therein may or may not occur. For example, an "optionally substituted" group means that the group may be unsubstituted or substituted.

The term "heteroatom" as used herein refers to oxygen (O), nitrogen (N), or S(O)$_m$ in which m may be 0, 1 or 2, i.e. a sulfur atom S, or a sulfoxide group SO, or a sulfonyl group S(O)$_2$).

The term "alkyl" refers to a group formed by removing a hydrogen atom at any carbon atom from a saturated hydrocarbon consisting solely of two elements, C and H. The "alkyl group" described herein includes an acyclic alkyl group such as a linear alkyl group or a branched alkyl group; and a cycloalkyl group such as a monocyclic alkyl group, a spirocycloalkyl group, a fused cycloalkyl group, or a bridged cycloalkyl group.

The "alkyl" as used herein includes an optionally substituted acyclic alkyl group which preferably has from 1 to 20 carbon atoms, more preferably from 1 to 12 carbon atoms, and most preferably from 1 to 6 carbon atoms; for example, methyl, ethyl, n-propyl, isopropyl, n-butyl, sec-butyl, isobutyl, tert-butyl, n-pentyl, n-hexyl, chloromethyl, fluoroethyl, trifluoromethyl or 1,1,1-trifluoroethyl and the like.

The "alkyl" as used herein also includes an optionally substituted cycloalkyl (e.g., C3-C20 cycloalkyl or C3-C12 cycloalkyl or C3-C8 cycloalkyl), for example, cyclopropyl, cyclobutyl, cyclopentyl, cyclohexyl, cycloheptyl, cyclooctyl, decalinyl, norbornyl, adamantyl, fluorocyclopropyl, 2-iodocyclobutyl, 2,3-dimethyl cyclopentyl, 2,2-dimethoxycyclohexyl and 3-phenylcyclopentyl and the like.

The "C1-C6alkyl", also known as "lower acyclic alkyl", is a subset of alkyl which refers to a linear or branched alkyl group having from 1 to 6 carbon atoms, including, for example, methyl, ethyl, n-propyl, isopropyl, n-butyl, sec-butyl, isobutyl, tert-butyl, n-pentyl, n-hexyl, and the like.

"Alkyl" may be unsubstituted or may be substituted. The "alkyl" as used herein is optionally substituted by one or more substituents, wherein the substituents are independently selected from the group consisting of halo, cyano, nitro (—NO$_2$), hydroxy, amino, carboxy, acyl, alkyl, heterocyclyl, alkenyl, alkynyl, aryl, heteroaryl, ═O, ═S, —SH, R$^{16}$O—, R$^{16}$S—, R$^{16}$(O═)S—, R$^{16}$(O═)$_2$S—, wherein R$^{16}$ is alkyl, heterocyclyl, alkenyl, alkynyl, aryl or heteroaryl.

Preferably, the "alkyl" as used herein is optionally substituted with from 1 to 3 substituents, wherein the substituents are independently selected from the group consisting of hydroxy, halo, nitro, cyano, amino, carboxy, C1-C6 acyclic alkyl, C3-C8 cycloalkyl, C2-C6 acyclic alkenyl-, C2-C6 acyclic alkynyl-, C3-C8 cycloalkyl, C3-C8 cycloalkenyl, C6-C14 aryl, heteroaryl having 5 to 14 ring members, C1-C6 acyclic alkyl-O—, C3-C8 cycloalkyl-O—, C2-C6 acyclic alkenyl-O—, C2-C6 acyclic alkynyl-O—, C3-C8 cycloalkenyl-O—, C6-C14 aryl-O—, heteroaryl-O— having 5 to 14 ring members, C1-C6 acyclic alkyl-S—, C3-C8 cycloalkyl-S—, C2-C6 acyclic alkenyl-S—, C2-C6 acyclic alkynyl-S—, C3-C8 cycloalkenyl-S—, C6-C14 aryl-S—, heteroaryl-S— having 5 to 14 ring members, heterocycloalkyl having 3 to 8 ring members, heterocycloalkenyl having 3 to 8 ring members, ═O, ═S, —SH, —CF$_3$, —CO$_2$C1-C6 acyclic alkyl group, C1-C6 acyclic alkyl-S—, C1-C6 acyclic alkyl (O═)S— and C1-C6 acyclic alkyl (O═)$_2$S—.

The "alkyl" as used herein preferably refers to an acyclic alkyl group, more preferably an unsubstituted acyclic alkyl group or a halogen substituted acyclic alkyl group, examples of which include, but are not limited to; for example, methyl, ethyl, n-propyl, isopropyl, n-butyl, sec-butyl, isobutyl, tert-butyl, n-pentyl, n-hexyl, fluoromethyl, chloromethyl, fluoroethyl, chloroethyl, fluoropropyl (1-fluoropropyl, 2-fluoropropyl, or 3-fluoropropyl), trifluoromethyl or 1,1,1-trifluoroethyl, and the like.

The term "alkenyl" refers to a group formed by removing a hydrogen atom at any carbon atom from a hydrocarbon that consists of only two elements, C and H, and which contains one or more carbon-carbon double bonds without carbon-carbon triple bonds or aromatic bonds. The "alkenyl" as used herein includes an acyclic alkenyl group such as a linear or branched alkenyl group; and also includes a cyclic alkenyl group such as a monocycloalkenyl group, a spirocycloalkenyl group, a fused cycloalkenyl group or a bridged cycloalkenyl group. The alkenyl group may be unsubstituted or substituted.

The "alkenyl" as used herein includes an optionally substituted alkenyl group, preferably having from 2 to 20 carbon atoms, more preferably from 2 to 12 carbon atoms, most preferably from 2 to 6 carbon atoms; for example, vinyl, 1-propenyl, 2-propenyl, 1-butenyl, 2-butenyl, isobutenyl, 1-pentenyl, 2-pentenyl, isopentenyl, 1-hexenyl, 2-hexenyl, 3-hexenyl, isohexenyl, 1-heptenyl, 2-heptenyl, 3-heptenyl, 1-octenyl, 2-octenyl, 3-octenyl, 4-octenyl, 1-nonenyl, 1-decenyl, 1-undecenyl, 1-dodecenyl, and the like.

The "alkenyl" as used herein also includes an optionally substituted cycloalkenyl (e.g., C3-C20 cycloalkenyl or C3-C12 cycloalkenyl or C3-C8 cycloalkenyl), for example, cyclobutenyl, cyclopentenyl, cyclohexenyl, cycloheptenyl, cyclobutadienyl, cyclopentadienyl, cycloheptatrienyl, and the like.

"Alkenyl" may be unsubstituted or substituted. The "alkenyl" as used herein is optionally substituted by one or more (e.g., 1-3) substituents, wherein the choice and preference of the substituents are the same as those for the "alkyl".

The "alkenyl" as used herein is preferably an acyclic alkenyl group, more preferably an unsubstituted acyclic alkenyl group or a halogen-substituted acyclic alkenyl group, examples of which include, but are not limited to, for example, vinyl, 1-propenyl, 2-propenyl, 1-butenyl, 2-butenyl, isobutenyl, 1-pentenyl, 2-pentenyl, isopentenyl, 1-hexenyl, 2-hexenyl, 3-hexenyl, isohexenyl, 1-heptenyl, 2-heptenyl, 3-heptenyl, 1-octenyl, 2-octenyl, 3-octenyl, 4-octenyl, 1-nonenyl, 1-decenyl, 1-undecenyl, 1-dodecenyl, and the like.

The term "alkynyl" refers to a group formed by removing a hydrogen atom at any carbon atom from a hydrocarbon that consists of only two elements C and H and which contains one or more carbon-carbon triple bonds without aromatic bonds. The "alkynyl" as used herein includes an acyclic alkynyl group such as a linear or branched alkynyl group, and includes a cycloalkynyl group such as monocycloalkynyl, spirocycloalkynyl, fused cycloalkynyl, or bridged alkynyl. The alkynyl group can optionally contain one or more carbon-carbon double bonds. The alkynyl group may be unsubstituted or substituted.

As used herein, "alkynyl" includes an optionally substituted acylicalkynyl group, preferably having from 2 to 20 carbon atoms, more preferably from 2 to 12 carbon atoms, most preferably from 2 to 6 carbon atoms; for example, acetynyl, propynyl, 1-butynyl, 2-butynyl, isobutynyl, 1-pentynyl, 2-pentynyl, isopenynyl, 3-methyl-3-butynyl, 1-hexynyl, 2-hexynyl, 3-hexynyl, 3-heptynyl, 1-octynyl, 1-nonynyl, 1-decynyl, 1-undecynyl, 1-dodecynyl and the like.

The "alkynyl" as used herein also includes optionally substituted cycloalkynyl (e.g., C8-C18 cycloalkynyl), for example, cyclooctynyl, and the like.

"Alkynyl" may be unsubstituted or substituted. The "alkynyl" as used herein is optionally substituted by one or more (e.g., 1-3) substituents, wherein the choice and preference of the substituents are the same as those for the "alkyl".

The "alkynyl" as used herein is preferably an acyclic alkenyl group, more preferably an unsubstituted acyclic alkenyl group or a halogen-substituted acyclic alkenyl group, examples of which include, but are not limited to, for example, ethynyl, propynyl, 1-butynyl, 2-butynyl, isobutynyl, 1-pentynyl, 2-pentynyl, isopentynyl, 3-methyl-3-butynyl, 1-hexynyl, 2-hexynyl, 3-hexynyl, 3-heptynyl, 1-octynyl, 1-nonynyl, 1-decynyl, 1-undecynyl, 1-dodecynyl and the like.

The term "aromatic group", also known as "aryl", refers to a group having a conjugated pi-electron system derived from 6 to 14 membered pure carbon monocyclic or fused polycyclic compound. The aryl ring may be fused to a heteroaromatic ring, a heterocyclic ring, cycloalkane, spirocycloalkane, fused cycloalkane, bridged cycloalkane, cycloalkenylene, spirocycloalkene, fused cycloalkene, bridged cycloalkene, cycloalkyne, spirocycloalkyne, fused cycloalkyne or bridged cycloalkyne. The aryl group may be unsubstituted or substituted. Examples thereof include, but are not limited to, phenyl, naphthyl, 2-methylphenyl, 3-methylphenyl, 4-methylphenyl, methoxyphenyl (such as 2-methoxyphenyl, 3-methoxyphenyl, 4-methoxyphenyl), chlorophenyl (such as 2-chlorophenyl, 3-chlorophenyl, 4-chlorophenyl), fluorophenyl (such as 2-fluorophenyl, 3-fluorophenyl, 4-fluorophenyl), bromophenyl (such as 2-bromophenyl, 3-bromophenyl, 4-bromophenyl), 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methyl phenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, and the like.

The "aryl" as used herein are optionally substituted with from 1 to 4 or from 1 to 3 substituents, wherein the choice and preference of the substituents are the same as those for the "alkyl".

The term "heteroaromatic group", also known as "heteroaryl" refers to a group derived from an aromatic system containing from 5 to 18 ring members, preferably from 5 to 14 ring members, one or four ring members of which are heteroatoms selected from the group consisting of oxygen, nitrogen and sulfur. The heteroaryl ring may be fused to an aryl ring, a heterocyclic ring, cycloalkane, spirocycloalkane, fused cycloalkane, bridged cycloalkane, cycloalkenylene, spirocycloalkene, fused cycloalkene, bridged cycloalkene, cycloalkyne, spirocycloalkyne, fused cycloalkyne or bridged cycloalkyne. The "heteroaryl" may be unsubstituted or substituted. Examples of heteroaryl groups include, but are not limited to, thienyl, furanyl, pyrrolyl, pyridyl, pyrimidinyl, imidazolyl, pyrazinyl, oxazolyl, thiazolyl, benzothienyl, benzofuranyl, benzooxazolyl, benzimidazolyl, indenyl, quinolyl, isoquinolyl and quinazolinyl, and the like.

The "heteroaryl" as used herein are optionally substituted with from 1 to 4 or from 1 to 3 substituents, wherein the choice and preference of the substituents are the same as those for the "alkyl".

The term "acyl" as used herein refers to RC(=O)—, wherein R is H or C1-C18 (preferably C1-C12, more preferably C1-C6) alkyl. Examples of "acyl" include, but are not limited to, formyl, acetyl, benzoyl, nicotinyl, propionyl, isobutyryl, oxalyl, and the like.

The acyl group RC(=O)— as used herein is optionally substituted by one or more (e.g., 1-3) substituents, wherein the choice and preference of the substituents are the same as those for the "alkyl".

The term "form a ring" or "ring" as used herein means forming a cyclic structure such as a cycloalkane ring, a cycloalkene ring, a cycloalkyne ring, an aromatic ring, a heterocycloalkane ring, a heterocycloalkene ring, a heterocycloalkyne ring, a heteroaryl ring or the like wherein the cyclic structure may be a monocyclic, bicyclic or polycyclic structure including its fused ring, bridged ring, and spiro ring structure.

The term "saturated ring" as used herein refers to a cyclic structure forming a cycloalkane ring or a heterocycloalkane ring, in which the cyclic structure may be a monocyclic, bicyclic, or polycyclic structure, including its fused ring, bridged ring, and spiro ring structure. "Saturated ring" includes all-carbocyclic rings and saturated heterocyclic rings, which are preferably 3 to 12 membered rings, particularly preferably 3 to 8 membered rings, and most preferably 4 to 6 membered rings. Examples of the all-carbocyclic ring include, for example, a cyclopropane ring, a cyclobutane ring, a cyclopentane ring, a cyclohexane ring, a cycloheptane ring, and the like. The term "saturated heterocyclic rings" refers to a saturated ring structure containing one or more heteroatoms as ring atoms, example of which comprises for example piperidinyl, pyrrolidinyl, piperazinyl, azetidinyl, aziridinyl, morpholinyl, thiacyclobutyl, oxacyclopentyl (tetrahydrofuryl), oxacyclohexyl (tetrahydropyranyl) and the like. The ring structure is optionally substituted with one or more (e.g., 1-3) substituents, wherein the choice and preference of the substituents are the same as those for the "alkyl".

Herein, a numerical range relating to the number of substituents, the number of carbon atoms, and the number of ring members represents an enumeration of all integers in the range, and the range is only a simplified representation thereof. For example:

"1-4 substituents" means 1, 2, 3 or 4 substituents;
"1-3 substituents" means a 1, 2 or 3 substituent;
"3 to 12-membered ring" means a 3, 4, 5, 6, 7, 8, 9, 10, 11 or 12-membered ring;
"3 to 8 membered ring" means a 3, 4, 5, 6, 7, or 8 membered ring;
"1-12 carbon atoms" or "C1-C12" means 1 (C1), 2 (C2), 3 (C3), 4 (C4), 5 (C5), 6 (C6), 7 (C7), 8 (C8), 9 (C9), 10 (C10), 11 (C11) or 12 (C12) carbon atoms;
"1-6 carbon atoms" or "C1-C6" means 1 (C1), 2 (C2), 3 (C3), 4 (C4), 5 (C5) or 6 (C6) carbon atoms;
"1-4 carbon atoms" or "C1-C4" means 1 (C1), 2 (C2), 3 (C3), 4 (C4) carbon atoms;
"2-6 carbon atoms" or "C2-C6" means 2 (C2), 3 (C3), 4 (C4), 5 (C5) or 6 (C6)carbon atoms;
"C3-C8" means 3 (C3), 4 (C4), 5 (C5), 6 (C6), 7 (C7) or 8 (C8) carbon atoms;
"3 to 8 ring members" means 3, 4, 5, 6, 7, or 8 ring members.

Thus, a numerical range associated with the number of substituents, the number of carbon atoms, and the number of ring members also encompasses any one of its subranges, and each subrange is also considered to be disclosed herein.

2. Application of the Compounds of the Invention

Another object of the present invention is to provide a novel medical application of the compound represented by Formula I.

The inventors have found through experiments that the compound according to the present invention is a small molecule drug that degrades ER and can be used as a SERD. It is suitable for cancer, immune deficiency, nervous system defects including neurodegenerative diseases, cardiovascular diseases, reproductive system defects, metabolic system defects, and the like.

In particular, the diseases which are suitable for being treated and/or prevented by the administration of a compound of Formula I include, but not limited to, cancer such as breast cancer, ovarian cancer, colorectal cancer, prostate cancer, and endometrial cancer, immune deficiency such as insulin resistance, lupus erythematosus, arthritis, and multiple sclerosis, neurous system defects such as stroke, Alzheimer's disease, Parkinson's disease, and depression, cardiovascular diseases such as coronary heart disease, hypertension, myocardial infarction, and aortic valve sclerosis, reproductive system defects such as endometriosis and infertility, metabolic system defects such as obesity, osteoporosis, and osteopenia, and the like.

Accordingly, one aspect of the present invention relates to a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, for use as a selective estrogen receptor degradation agent (SERD).

Another aspect of the present invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, as a selective estrogen receptor degradation agent (SERD).

Another aspect of the present invention related to a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, as a medicament for the treatment and/or prevention of a disease associated with ER.

Another aspect of the present invention related to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, for the manufacture of a medicament for the treatment and/or prevention of a disease associated with ER.

Another aspect of the invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof for the preparation of a selective estrogen receptor degradation agent (SERD).

Another aspect of the invention relates to use of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof for the manufacture of a medicament for the treatment and/or prophylaxis of a disease associated with ER.

Another aspect of the invention relates to a method of treating and/or preventing a disease associated with ER, the method comprising administering to a patient in need thereof a therapeutically effective amount of a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof.

Another aspect of the invention relates to a method of treating and/or preventing a disease associated with ER, the method comprising administering to a patient in need thereof a therapeutically effective amount of a pharmaceutical composition, the pharmaceutical composition comprising a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, and one or more pharmaceutically acceptable carriers, diluents or excipients.

As used herein, the term "patient" refers to all mammals, including humans. Examples of patients include humans, cows, dogs, cats, goats, sheep, rats, pigs, and rabbits.

As used herein, the term "diseases associated with ER" comprises, but not limited to: cancer such as breast cancer, ovarian cancer, colorectal cancer, prostate cancer, and endometrial cancer, osteoporosis, neurodegenerative disease, cardiovascular disease, insulin resistance, lupus erythematosus, endometriosis, obesity, and the like.

As used herein, the term "pharmaceutically acceptable salt" of a compound of Formula I refers to an inorganic or organic acid addition salt or an organic or inorganic base addition salt of the compound suitable for use in mammals (i.e., being safe and effective when applied). These salts can be prepared in situ during the final isolation and purification of the compound, or can be obtained by reacting a free form of the pure compound with a suitable organic or inorganic acid or base and then separating the formed salt. Typical salts include hydrobromides, hydrochlorides, sulfates, hydrogen sulfates, nitrates, acetates, oxalates, valerates, oleates, palmitates, stearates, laurates, borates, benzoates, lactates, phosphates, tosylates, citrates, maleates, fumarates, succinates, tartrates, glucoheptonates, lactate, lauryl sulfonate, and the like. These salts may include salts of cations from alkali metals and alkaline earth metals (such as sodium, lithium, potassium, calcium, magnesium, and the like), as well as non-toxic ammonium, quaternary ammonium, and amine cations including, but not limited to, ammonium, tetramethylammonium, tetraethylammonium, methylamine, dimethylamine, trimethylamine, triethylamine, ethylamine, or the like.

As used herein, the term "prodrug" of a compound of Formula I refers to a derivative of the compound suitable for use in mammals (i.e., being safe and effective when applied), which releases the compound of Formula I or a pharmaceutically acceptable salt thereof in vivo after being administered. Examples of prodrugs include esters, amides and the like.

3. Pharmaceutical Compositions and Pharmaceutical Dosage Forms Containing the Compounds of the Invention For therapeutic use, the compounds of Formula I are typically administered to a patient in the form of a pharmaceutical composition comprising at least one of the above compounds as an active ingredient, optionally including a pharmaceutically acceptable adjuvant and/or excipient and/or a pharmaceutically acceptable solid or liquid carrier.

Another aspect of the invention relates to a pharmaceutical composition comprising a compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof, and one or more pharmaceutically acceptable carriers, adjuvants or excipients.

The present invention also relates to a process for the preparation of the above pharmaceutical composition comprising mixing the compound of Formula I (or a preferred compound of Formula I), or an isotopically labeled compound thereof, or an optical isomer thereof, a geometric isomer thereof, a tautomer thereof or a mixture of various isomers, or a pharmaceutically acceptable salt thereof, or a prodrug thereof with a pharmaceutically acceptable carrier, adjuvant or excipient.

The pharmaceutical compositions of the invention may be formulated as suitable dosage forms for oral, parenteral (including subcutaneous, intramuscular, intradermal and intravenous), bronchial or nasal administration as desire. Preferably, the pharmaceutical compositions of the invention may be formulated as suitable dosage forms for oral administration.

If a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula I according to the invention.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol;

(d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The amount of the compound of Formula I in pharmaceutical compositions and dosage forms can be suitably determined by those skilled in the art as needed. For example, the compound of Formula I can be present in a pharmaceutical composition or dosage form in a therapeutically effective amount.

4. Dosage of the Compound of the Invention

As used herein, the term "therapeutically effective amount" is such an amount of the compound of the present invention that, when administered to a patient, effectively delays or eliminates symptoms of the patient or improves health conditions of the patient. The specific application dosage can be determined by doctors according to the specific conditions of patients. The precise dosage to be used depends not only on the route of administration, conditions, severity of conditions to be treated, and various physical factors associated with the subject to be treated, but can also be determined in accordance with the judgment of health care practitioners. In vitro or in vivo tests can be used to help determine the optimal dosage range.

The compounds of the present invention can be administered to a patient at dosage levels in the range of about 0.01 to about 4,000 mg per day or 0.05 to 2000 mg per day, or 0.1 to 1000 mg per day or 0.1 to 500 mg per day. For a normal human adult having a body weight of about 70 kilograms, a dosage may be for example in the range of about 0.001 to about 100 mg per kilogram of body weight per day or in the range of about 0.01 to about 100 mg per kilogram of body weight per day or in the range of about 0.05 to about 50 mg per kilogram of body weight per day. The specific dosage used, however, can vary. The determination of optimum dosages for a particular patient is well-known to those skilled in the art.

The above daily dosages may be administered continuously. For example, it may be administrated every 2 hours, every 6 hours, every 8 hours, every 12 hours, about every 24 hours, or every 2 days, every 1 day, every 1 week, every two weeks, every three weeks, or every month once. The dosage and frequency during the entire course of treatment will be determined based on the judgment of health care practitioners. In one embodiment, the compound of the invention, or a pharmaceutically acceptable salt thereof, is administered concurrently with another therapeutic agent.

In one embodiment, a composition comprising an effective amount of the compound of the invention, or a pharmaceutically acceptable salt thereof, and an effective amount of another therapeutic agent in the same composition can be administered. Effective amounts of other therapeutic agents are known to those skilled in the art. Moreover, determining the range of optimal effective amount of other therapeutic agents is within the skill of the artisan.

5. Method for Preparing the Compound of the Present Invention

The compounds of Formula I of the present invention may be synthesized by a variety of methods familiar to those skilled in the art of organic synthesis. Some exemplary synthetic methods are given below which are well known in the art of synthetic chemistry. The compounds of Formula I are synthesized according to the methods described below, as well as in combination with the methods commonly employed by organic synthetic chemists. The synthetic routes of the compounds in the present invention are not limited to the methods summarized below. The synthesis of certain compounds may require adjustment of operating conditions to meet the requirements of various functional groups. Various protecting groups known to those skilled in the art may be necessary. Purification can be accomplished, if desired, by silica gel column elution with a suitable organic solvent system or by recrystallization. In addition, various specific examples herein also illustrate methods of synthesizing the compounds of the invention.

The compounds of the present invention are mainly synthesized by the following technical scheme including Route 1 and Route 2a, Route 2b. The following Route 1 and Route 2a, Route 2b schematically illustrate the synthesis of compounds of Formula I.

Route 1:

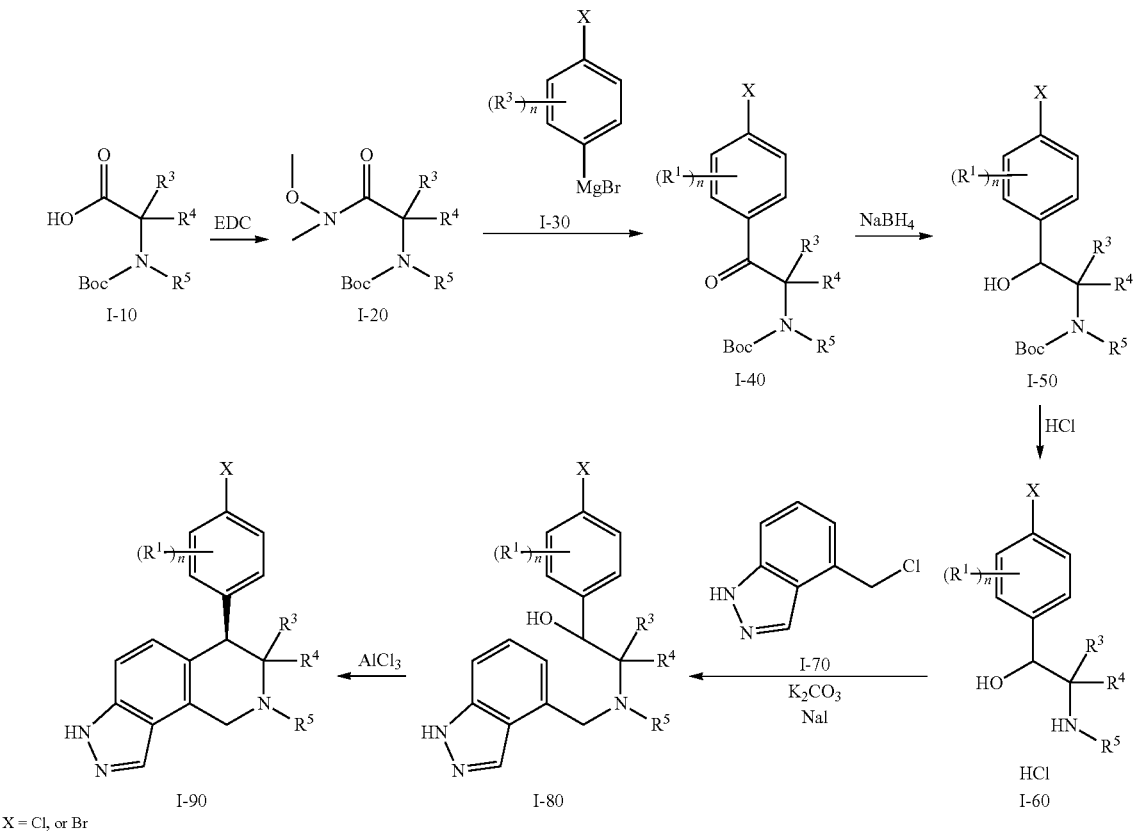

X = Cl, or Br

Route 1 involves the preparation of intermediate I-90, which may be used for Route 2a and Route 2b both: starting from a protected amino acid starting material I-10 which starting material itself can be purchased from a reagent supplier or synthesized from literature, this starting material is combined with N, O-dimethylhydroxylamine hydrochloride in the presence of a coupling agent such as EDC to affortWeinreb amide I-20; I-20 reacts with Grignard reagent I-30 which reagent iterself can be purchased from a reagent supplier or synthesized from literature to obtain ketone I-40; the ketone carbonyl of I-40 is reduced to affort a hydroxy compound I-50 under the action of a reducing agent such as sodium borohydride; the Boc protecting group on the nitrogen atom of I-50 is removed in the presence of an acidic medium such as hydrochloric acid or trifluoroacetic acid to affort intermediate I-60; I-60 is further hydrocarbylated with indazole I-70 which indazole itself can be purchased from a reagent supplier or synthesized from literature to affort intermediate I-80; and I-80 is ring-closed under the action of an acidic catalyst or a Lewis acid catalyst such as aluminum trichloride, thereby obtaining a tricyclic intermediate I-90.

Starting from I-90, the final compound of Formula I can be synthesized via Route 2a or Route 2b and the difference between Route 2a and Route 2b lies in the order in which I-90 is coupled to I-100 or I-100' and the side chain $R^7$ is introduced.

Route 2a:

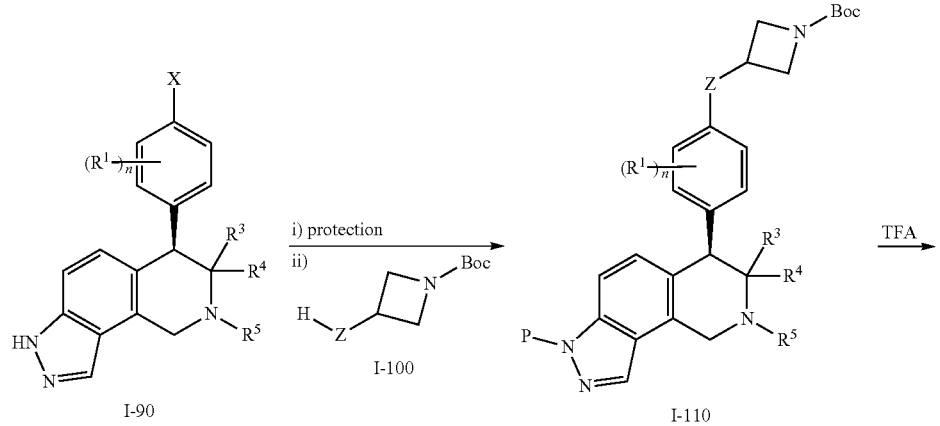

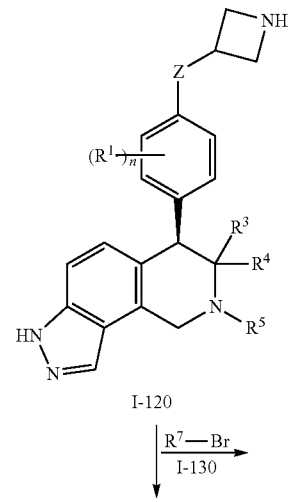

I-120

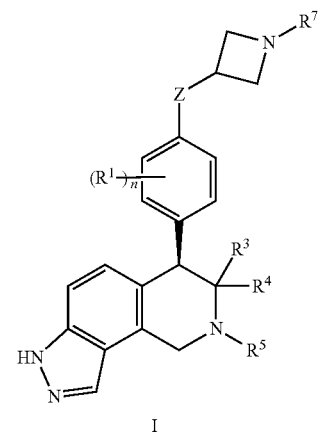

I

Route 2a in which I-90 is coupled first and then the side chain R⁷ is introduced in the first step, I-90 is protected with such as THP for its pyrazolemoiety and then is coupled with I-100 at its aryl-heteroatoms such as O, N, S, and the like, in the presence of metal catalysts such as copper or palladium, to affort intermediate I-110; in the next step, the Boc group and the THP protecting group for pyrazole of I-110 are removed with an acidic reagent such as trifluoroacetic acid, and the like to affort intermediate I-120; and in the final step, I-120 is selectively alkylated with an alkylating agent such as I-130, in which the nitrogen atom in the azetidine ring is alkylated, thereby obtaining the final product I.

Route 2b

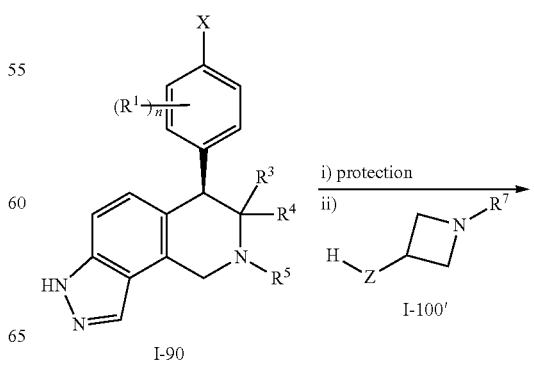

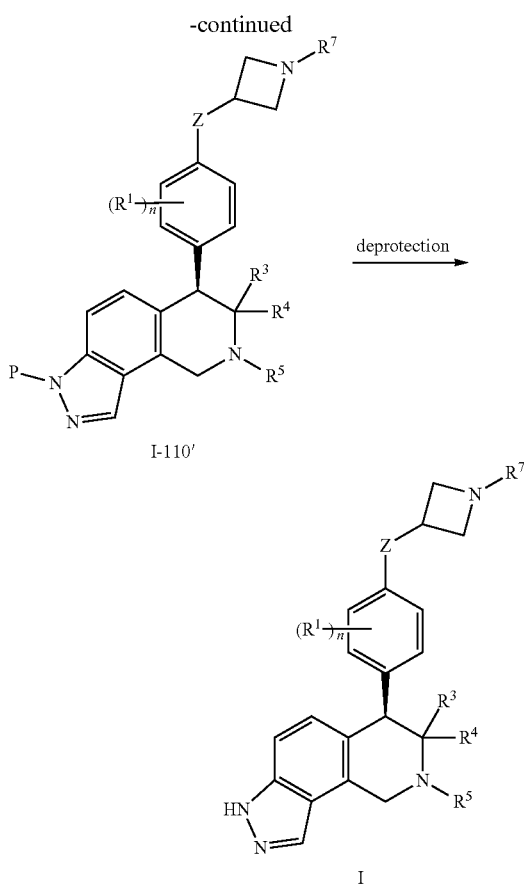

Route 2b in which the side chain R⁷ is introduced first and then I-90 is coupled: as in Route 2a, in the first step, I-90 is protected with such as THP for its pyrazole moiety and then is coupled with I-100' at its aryl-heteroatoms such as O, N, S, and the like, in the presence of metal catalysts such as copper or palladium, to affort intermediate I-110'; in the final step, the protecting group, such as THP for pyrazole of I-110' is removed with an acidic reagent such as trifluoroacetic acid, and the like, thereby obtaining the final product I.

Particular reaction conditions of the respective steps in the above respective synthesis schemes can be appropriately determined by those skilled in the art in accordance with principles and requirements of conventional chemical reactions. And the reaction conditions given in the following examples of the invention can be used as reference.

Referring to the various schemes in the present application, it would be apparent for those skilled in the art to appropriately adjust reactants, reaction conditions, and protecting groups and to easily design synthetic routes of other compounds of Formula I.

DETAILED DESCRIPTION OF EMBODIMENTS

Figure 1:
FIGS. 1, 2, and 3 show the immunoblot analysis results of compounds according to certain embodiments of the present invention, respectively.

The invention is further illustrated by the following examples; however, these examples do not limit the scope of the invention.

The structures of compounds were determined by liquid chromatography-mass spectrometry (LCMS) or nuclear magnetic resonance (NMR). The NMR chemical shift (δ) is expressed in units of $10^{-6}$ (ppm). The NMR spectrawere measured by Bruker-500 nuclear magnetic resonance apparatus in which deuterated dimethyl sulfoxide (DMSO-d6), deuterated chloroform (CDCl₃) and the like were used as solvent, and tetramethylsilane (TMS) was used as an internal standard. LCMS was determined using Shimadzu LCMS-2020.

Silica gel plates Huanghai HSGF254 available from Yantai, Shandong, China or plates GF254 from Qingdao, Shandong, Chinawere used as thin-layer chromatography silica gel plates. Generally, Huanghaisilica gel with 200 to 300 mesh available from Yantai, Shandong was used as a carrier for column chromatography.

All starting materials used in the present invention were purchased from chemical suppliers or can be synthesized by methods known in literatures.

The abbreviations used in the description of this article are as follows:
Boc: tert-butoxycarbonyl
br: nuclear magnetic broad peak
CAS: Chemical Abstracts Accession Number
CDCl₃: Deuterated chloroform
d: nuclear magnetic double peak
DIPEA: Diisopropylethylamine
DMF: N, N-dimethylformamide
DMSO-d6: dimethyl sulfoxide in which six hydrogen atoms are replaced by deuterium
EDC: 1-(3-dimethylaminopropyl)-3-ethylcarbodiimide hydrochloride
ESI: Electrospray ionization
ER: Estrogen receptor
LCMS: Liquid Chromatography-Mass Spectrometry
mg: microgram
ml: microliter
mmol: micromole
NMR: Nuclear Magnetic Resonance
ppm: one part per million
s: nuclear magnetic single peak
t: nuclear magnetic triplet peak
TFA: trifluoroacetic acid
TMS: tetramethylsilane
δ: chemical shift of nuclear magnetic resonance Preparation of Intermediate Compounds Preparation of Intermediate I-100'

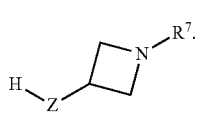

1-(2,3-difluoropropyl)azetidin-3-amine (I-100'-1)

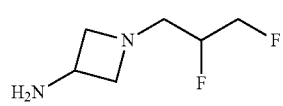

Step 1: 2-benzyloxymethyl oxide (I-100'-1-a)

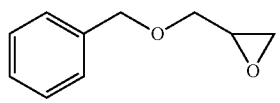

I-100'-1-a

NaOH (3.7 g), tetra-n-butylammonium iodide TBAI (3.43 g) and DMF (150 ml) were charged to a reaction flask and then cooled in an ice water bath. After that, ethylene oxide-2-ylmethanol (CAS: 52-5; 6.85 g) was dropped into the reaction flask and stirred for 2 hours; then benzyl bromide BnBr (17.3 g) was slowly added dropwise. After the addition was completed, the reaction was allowed to proceed at room temperature overnight. Then, water was added to quench the reaction, and the mixture was extracted with ethyl acetate. The ethyl acetate layer was collected and then washed twice with an aqueous diluted sodium chloride solution, dried over anhydrous sodium sulfate, filtered, and concentrated. The residue was purified by silica gel column chromatography to afford an oily product, I-100'-1-a (12 g). $^1$H NMR (500 MHz, DMSO-$d_6$) δ 7.41-7.26 (m, 5H), 4.53 (d, J=1.1 Hz, 2H), 3.76 (dd, J=11.5, 2.7 Hz, 1H), 3.30 (dd, J=11.5, 6.4 Hz, 1H), 3.15 (ddt, J=6.8, 4.2, 2.7 Hz, 1H), 2.74 (dd, J=5.1, 4.2 Hz, 1H), 2.57 (dd, J=5.1, 2.7 Hz, 1H).

Step 2: ((2,3-difluoropropoxy) methyl) benzene (I-100'-1-b)

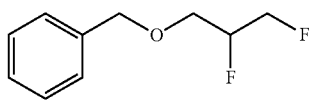

I-100'-1-b

I-100'-1-a (2 g) and Et$_3$N—HF (1.24 g) were added to a sealed tube and reacted at 150° C. for 1.5 hours. After cooling, aqueous saturated sodium bicarbonate solution was to quench the reaction, and the mixture was extracted with ethyl acetate. Then, the collected ethyl acetate layer was washed twice with aqeuous diluted sodium chloride solution, dried over anhydrous sodium sulfate, filtered, and concentrated, to afford crude product intermediate 3-benzyloxy-2-fluoro-1-propanol. Next, 20 ml of THF and DBU (2.04 g) were added to the above intermediate, which was cooled in an ice water bath, and then nonafluorobutylsulfonyl fluoride NfF (CAS: 375-72-4; 6.6 g) was added. The reaction was carried out for one hour. The reaction was quenched by the addition of an aqueous saturated sodium hydrogen carbonate solution, and the mixture was extracted with ethyl acetate. The collected ethyl acetate layer was washed twice with an aqueous diluted sodium chloride solution, dried over anhydrous sodium sulfate, filtered, and concentrated. The residue was purified by silica gel column chromatography to afford an oily product, I-100'-1-b (1.8 g). $^1$H NMR (500 MHz, DMSO-d6) δ 7.41-7.25 (m, 5H), 5.05-4.84 (m, 1H), 4.80-4.55 (m, 2H), 4.54 (d, J=1.3 Hz, 2H), 3.76-3.59 (m, 2H).

Step 3: 2,3-difluoropropyl2-nitrobenzenesulfonate (I-100'-1-c)

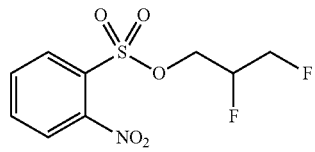

I-100'-1-c

I-100'-1-b (360 mg) and 10% palladium on carbon (76 mg) were mixed in 5 ml of THF, and the reaction was stirred overnight under a hydrogen blanket in a 40° C. oil bath to remove benzyl protection group. The reaction was then filtered to remove catalyst, and the filtrate was used directly in the next step. Then, to the filtrate, 5 ml of DCM was added and then Et$_3$N (1.44 ml), DMAP (23 mg) and 2-nitrobenzenesulfonyl chloride (480 mg) were added. The reaction was carried out at room temperature overnight. The reaction was quenched by the addition of an aqueous saturated sodium hydrogen carbonate solution, and the mixture was extracted with ethyl acetate. The collected ethyl acetate layer was washed twice with an aqueous diluted sodium chloride solution, dried over anhydrous sodium sulfate, filtered, concentrated, and purified by column chromatography to afford product I-100'-1-c (50 mg). $^1$H NMR (500 MHz, DMSO-$d_6$) δ 8.18 (ddd, J=9.3, 7.9, 1.3 Hz, 2H), 8.06 (td, J=7.8, 1.4 Hz, 1H), 7.98 (td, J=7.7, 1.3 Hz, 1H), 5.19-5.00 (m, 1H), 4.80-4.43 (m, 4H).

Step 4: benzyl (1-(2,3-difluoropropyl)azetidin-3-yl) carbamate (I-100'-1-d)

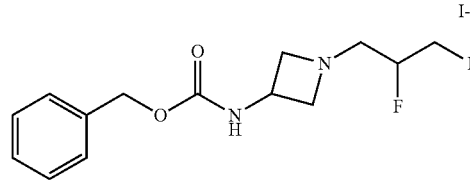

I-100'-1-d

I-100'-1-c (100 mg), benzyl azetidin-3-ylcarbamate hydrochloride (CAS: 914348-04-2; 100 mg) and diisopropylethyl amine (138 mg) were mixed in 1 ml of DMF; the reaction was stirred at room temperature overnight. The reaction was quenched by adding an aqueous solution, and the mixture was extracted with ethyl acetate. The collected ethyl acetate layer was then washed twice with an aqueous diluted sodium chloride solution, dried over anhydrous sodium sulfate, filtered, concentrated, and purified by a column chromatograph to afford product I-100'-1-d (98 mg). $^1$H NMR (500 MHz, DMSO-$d_6$) δ 7.78 (d, J=7.7 Hz, 1H), 7.41-7.27 (m, 5H), 5.00 (s, 2H), 4.81-4.42 (m, 3H), 4.14-4.00 (m, 1H), 3.54 (q, J=6.3 Hz, 2H), 2.93-2.84 (m, 2H), 2.65 (dd, J=22.8, 5.4 Hz, 2H).

Step 5: 1-(2,3-difluoropropyl)azetidin-3-amine (I-100'-1)

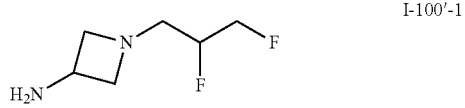

I-100'-1-d (3.5 mg) and 10% palladium on carbon (350 mg) were mixed in 40 ml of THF, and the reaction was stirred for 48 hours under a hydrogen blanket at room temperature to remove Cbz protection group. The reaction was then filtered to remove catalyst, and the filtrate was dried to afford product I-100'-1 (1.2 g). $^1$H NMR (500 MHz, DMSO-d$_6$) δ 4.78-4.41 (m, 3H), 3.51 (ddt, J=9.4, 5.0, 2.5 Hz, 2H), 3.34 (d, J=6.7 Hz, 1H), 2.65-2.58 (m, 4H), 1.85 (s, 2H).

(1-(3,3,3-trifluoropropyl)azetidin-3-amine (I-100'-2)

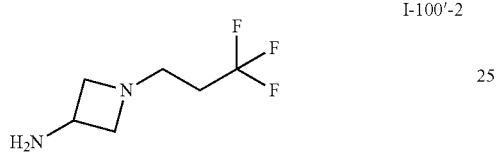

Step 1: benzyl (1-(3,3,3-trifluoropropyl)azetidin-3-yl) carbamate (I-100'-2-d)

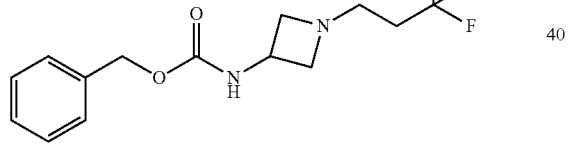

The synthetic route for I-100'-1-d was repeated, which starts from 1,1,1-trifluoro-3-iodopropane, benzyl azacyclbutan-3-ylcarbamate hydrochloride (CAS: 914348-04-2), and diisopropylethylamine (138 mg) to afford product I-100'-2-d. $^1$H NMR (500 MHz, DMSO-d6, δ, ppm): 7.77 (d, J=8.0 Hz, 1H), 7.4-7.3 (m, 5H), 5.00 (s, 2H), 4.1-4.0 (m, 1H), 3.51 (t, J=7.0 Hz, 2H), 2.81 (t, J=7.0 Hz, 2H), 2.54 (t, J=7.5 Hz, 2H), 2.3-2.2 (m, 2H).

Step 2: (1-(3,3,3-trifluoropropyl)azetidin-3-amine (I-100'-2)

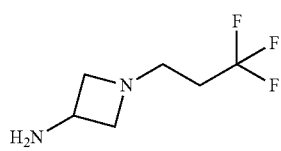

The synthetic route for I-100'-1 was repeated, which starts from I-100'-2-d to afford product I-100'-2. $^1$H NMR (500 MHz, DMSO-d6, δ, ppm): 3.5-3.4 (m, 2H), 3.4-3.3 (m, 1H), 2.6-2.4 (m, 4H), 2.3-2.2 (m, 2H).

Preparation of Intermediate I-60

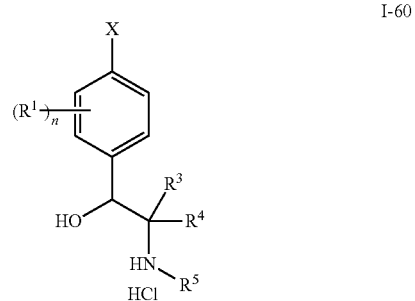

(2S)-1-(4-bromophenyl)-4-methyl-2-(methylamino)pentane-1-olhydrochloride (I-60-1)

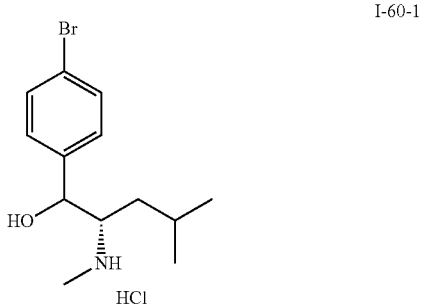 [SMILES: CN[C@@H](CC(C)C)C(O)c1ccc(Br)cc1 ; Cl]

Step 1: tert-butyl (S)-(1-(4-bromophenyl)-4-methyl-1-oxopent-2-yl) (methyl) carbamate (I-60-1-a)

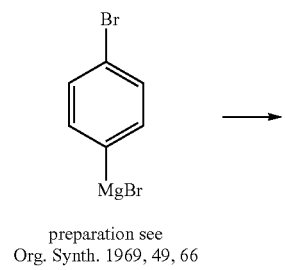

preparation see PCT 2004026293 preparation see Org. Synth. 1969, 49, 66

-continued

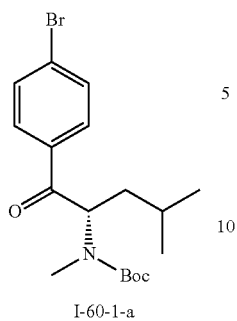

I-60-1-a

Compound I-60-1-a was synthesized from the above two known compounds by the methods known in J. Am. Chem. Soc. 2005, vol 127, 6152-6153 and its ancillary materials. The above two known compounds were synthesized by the methods known in WO2004026293 and Org. Synth. 1969, 49, 66. $^1$H NMR (500 MHz, DMSO-d6) δ (ppm): 7.83-7.72 (4H, m), 5.46-5.21 (1H, m), 2.60 (3H, d), 1.68-1.57 (2H, m), 1.57-1.46 (1H, m), 1.36 (9H, d, J=6.0 Hz), 0.99-0.92 (6H, m).

Step 2: tert-butyl ((2S)—1-(4-bromophenyl)-1-hydroxy-4-methylpent-2-yl) (methyl) carbamate (I-60-1-b)

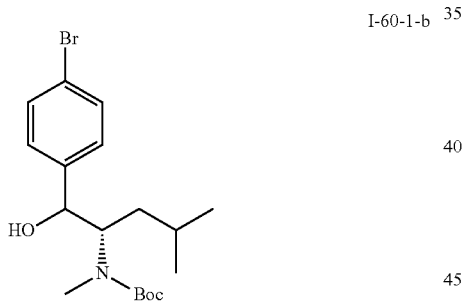

I-60-1-b

At room temperature, compound I-60-1-a (1 g) was dissolved in 10 ml of methanol, and then sodium borohydride (197 mg) was added. The reaction mixture was stirred at room temperature overnight. Then, water was added to quench the reaction, and the mixture was extracted with ethyl acetate. The collected ethyl acetate layer was then washed twice with an aqueous diluted sodium chloride solution, dried over anhydrous sodium sulfate, filtered, and concentrated. The residue was purified by silica gel column chromatography to afford Product as a yellow oil, I-60-1-b (1 g). $^1$H NMR (500 MHz, DMSO-d6) δ (ppm): 7.51-7.48 (2H, m), 7.27-7.23 (2H, m), 5.42-5.31 (1H, m), 4.55-4.53 (1H, m), 4.13-4.10 (1H, m), 2.68 (3H, d), 1.76-1.69 (1H, m), 1.78-1.34 (1H, m), 1.29 (3H, s), 1.24 (1H, s), 1.18 (6H, s), 0.87-0.76 (6H, m).

Step 3: (2S)-1-(4-bromophenyl)-4-methyl-2-(methylamino)pentane-1-olhydrochloride (I-60-1)

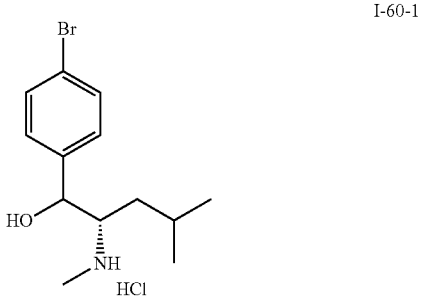 [SMILES: CN[C@@H](CC(C)C)C(O)c1ccc(Br)cc1 ; Cl]

I-60-1

Compound I-60-1-b (1 g) was dissolved in 10 ml of methanol, to which 6 M aqueous hydrochloric acid solution (9 ml) was added at room temperature. The reaction was stirred at room temperature overnight and then, concentrated to afford crude product as a yellow oil, I-60-1 (839 mg). $^1$H NMR (500 MHz, DMSO-d6) δ (ppm): 7.61-7.59 (2H, m), 7.41-7.38 (2H, m), 4.61 (1H, d, J=8.0 Hz), 3.23-3.19 (1H, m), 2.54-2.52 (3H, m), 1.47-1.42 (1H, m), 1.30-1.27 (3H, m), 1.26-1.12 (1H, m), 0.77 (3H, d, J=6.5 Hz), 0.62 (3H, d, J=6.5 Hz).

(2S)-1-(4-chloro-2,6-difluorophenyl)-4-methyl-2-(methylamino)pentane-1-ol hydrochloride (I-60-2)

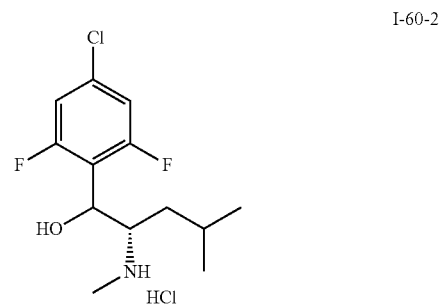 [SMILES: CN[C@@H](CC(C)C)C(O)c1c(F)cc(Cl)cc1F ; Cl]

I-60-2

Step 1: tert-butyl (S)-(1-(4-chloro-2,6-difluorophenyl)-4-methyl-1-oxopent-2-yl) (methyl) carbamate (I-60-2-a)

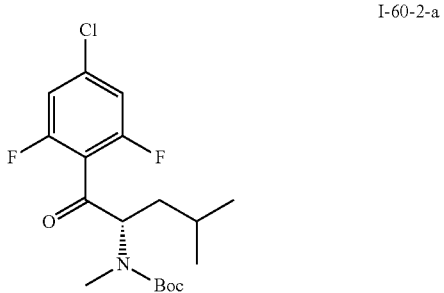 [SMILES: CC(C)C[C@@H](C(=O)c1c(F)cc(Cl)cc1F)N(C)C(=O)OC(C)(C)C]

I-60-2-a

The synthetic route for I-60-1-a was repeated, which starts from tert-butyl (S)-(1-(methoxy (methyl) amino)-4-methyl-1-oxopent-2-yl) (methyl) carbamate (CAS: 676628-64-1) and (4-chloro-2,6-difluorophenyl) magnesium bromide (see PCT 2016039404 for its synthesis) to afford product I-60-2-a. ¹H NMR (500 MHz, dmso-d6) δ (in ppm): 7.65-7.67 (1H, d, J=10.0 Hz), 7.57-7.58 (1H, d, J=8.0 Hz), 2.71-2.78 (3H, d, J=35.0 Hz), 2.22-2.23 (1H, d, J=5.0 Hz), 1.58-1.77 (4H, m), 1.32-1.35 (9H, d, J=15.0 Hz), 0.92-1.0 (18H, m).

Step 2: tert-butyl ((2S)-1-(4-chloro-2,6-difluorophenyl)-1-hydroxy-4-methylpent-2-yl) (methyl) carbamate (I-60-2-b)

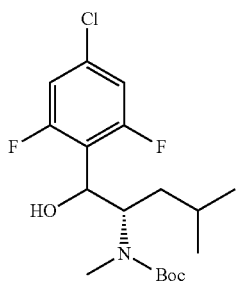

I-60-2-b

The synthetic route for I-60-1-b was repeated, which starts from I-60-2-a to afford I-60-2-b: LCMS ESI (+): 378 (M+1)⁺.

Step 3: (2S)-1-(4-chloro-2,6-difluorophenyl)-4-methyl-2-(methylamino)pentane-1-ol hydrochloride (I-60-2)

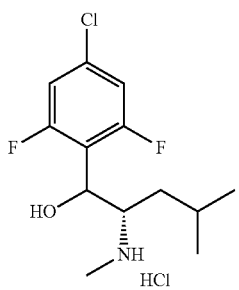

I-60-2

The synthetic route for I-60-1 was repeated, which starts from I-60-2-b to afford I-60-2: ESI (+): 278 (M+1)⁺.

(2S)-1-(4-chloro-2,6-difluorophenyl)-3-cyclopropyl-2-(methylamino)propan-1-ol hydrochloride (I-60-3)

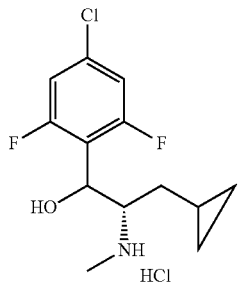

I-60-3

Step 1: tert-butyl (S)-(1-(4-chloro-2,6-difluorophenyl)-3-cyclopropyl-1-oxopropan-2-yl) (methyl) carbamate (I-60-3-a)

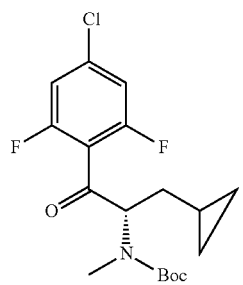

I-60-3-a

The synthetic route for I-60-1-a was repeated, which starts from tert-butyl (S)-(3-cyclopropyl-1-(methoxy (methyl) amino)-1-oxopropan-2-yl) (methyl) carbamate (CAS: 676628-64-1) and (4-chloro-2,6-difluorophenyl) magnesium bromide (see PCT 2016039404 for its synthesis) to afford product I-60-3-a: ¹H NMR (500 MHz, dmso-d6) δ (in ppm): 7.49 (d, J=8.3 Hz, 1H), 7.39 (d, J=8.3 Hz, 1H), 4.66 (s, 0.5H), 4.36 (dd, J=9.5, 4.6 Hz, 0.5H), 2.79 (s, 1.5H), 2.68 (s, 1.5H), 1.81 (dt, J=14.2, 5.4 Hz, 0.5H), 1.68 (dt, J=12.6, 5.6 Hz, 0.5H), 1.64-1.58 (m, 0.5H), 1.54 (dt, J=14.2, 8.8 Hz, 0.5H), 1.19 (s, 4.5H), 1.11 (s, 4.5H), 0.64-0.53 (m, 1H), 0.35 (dtd, J=25.9, 8.7, 4.3 Hz, 2H), 0.06--0.10 (m, 2H).

Preparation of tert-butyl (S)-(3-cyclopropyl-1-(methoxy (methyl) amino)-1-oxopropan-2-yl) (methyl) carbamate

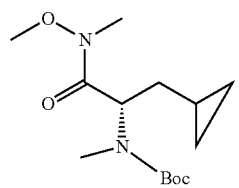 [SMILES: CON(C)C(=O)[C@H](CC1CC1)N(C)C(=O)OC(C)(C)C]

NaH (132 mg) was suspended in 10 ml of DMF, and cooled with an ice-water bath. And then to the mixture, tert-butyl (S)-(3-cyclopropyl-1-(methoxy (methyl) amino)-1-oxopropan-2-yl) carbonate (0.9 g; CAS: 882004-10-6; prepared according to the literature Bioorganic & Medicinal Chemistry Letters, 2006, 16 (6), 1621-1627) in DMF (5 ml) was added dropwise and was stirred in an ice water bath for 2 hours. Then methyl iodide (563 mg) was added dropwise. The reaction was stirred at room temperature overnight. An aqueous solution was added to quench the reaction, and the mixture was extracted with ethyl acetate. The collected ethyl acetate layer was then washed twice with an aqueous diluted sodium chloride solution, dried over anhydrous sodium sulfate, filtered, concentrated, and purified by column chromatographyto afford a pure product (570 mg). $^1$H NMR (500 MHz, DMSO-d6) δ 4.92 (d, J=83.0 Hz, 1H), 3.59 (s, 3H), 3.03 (d, J=5.6 Hz, 3H), 2.65 (d, J=25.9 Hz, 3H), 1.59-1.45 (m, 1H), 1.33 (s, 10H), 0.51 (pd, J=7.2, 3.7 Hz, 1H), 0.39-0.24 (m, 2H), 0.05-0.0 (m, 2H).

Step 2: tert-butyl ((2S)-1-(4-chloro-2,6-difluorophenyl)-3-cyclopropyl-1-hydroxypropan-2-yl) (methyl) carbamate (I-60-3-b)

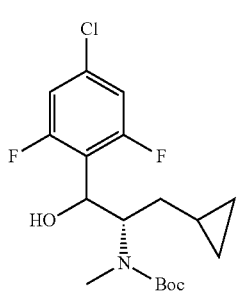

The synthetic route for I-60-1-b was repeated, which starts from I-60-2-a to afford I-60-2-b: LCMS ESI (+): 376 (M+1)$^+$.

Step 3: (2S)-1-(4-chloro-2,6-difluorophenyl)-3-cyclopropyl-2-(methylamino)propan-1-ol hydrochloride (I-60-3)

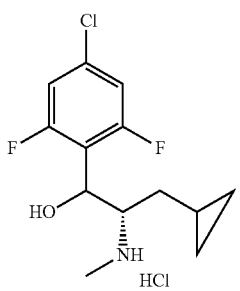

The synthetic route for I-60-1 was repeated, which starts from I-60-3-b to afford I-60-3: ESI (+): 276 (M+1)$^+$.

Example 1

1-(3-fluoropropyl)-N-(4-((6R, 7S)-7-isobutyl-8-methyl-6,7,8,9-tetrahydro-3H-pyrazolo [3,4-h]isoquinolin-6-yl) phenyl)azetidin-3-amine (1)

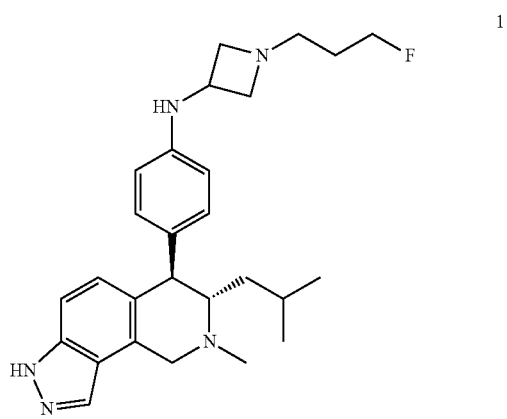 [SMILES: CC(C)C[C@H]1[C@H](c2ccc(NC3CN(CCCF)C3)cc2)c2ccc3[nH]ncc3c2CN1C]

Step 1: (2S)-2-(((1H-indazol-4-yl) methyl) (methyl) amino)-1-(4-bromophenyl)-4-methylpent-1-ol (1a)

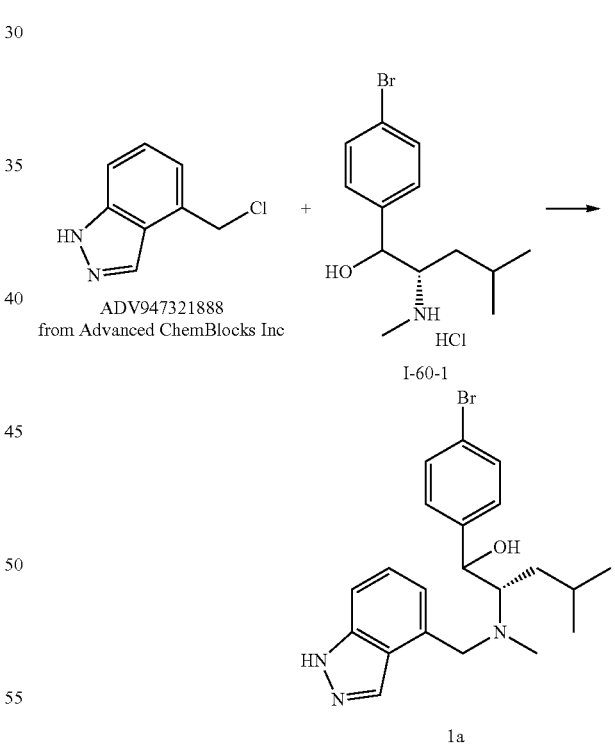

Compound I-60-1 (839 mg), 4-(chloromethyl)-1H-indazole (ADV947321888, available from Advanced ChemBlocks Inc., 739 mg), potassium carbonate (1.8 g), and sodium iodide (39 mg) were mixed in anhydrous DMF at room temperature. The reaction was stirred at room temperature overnight. Then, the mixture was extracted with ethyl acetate and water; and the organic phase was separated. The separated organic phase was washed twice with an aqueous diluted sodium chloride solution, dried over anhydrous sodium sulfate, filtered, and concentrated. The residue was purified by silica gel column chromatography to afford a yellow solid product 1a (950 mg). ¹H NMR (500 MHz, DMSO-d6) δ (ppm): 13.00 (1H, s), 8.07 (1H, s), 7.50 (2H, d, J=8.0 Hz), 7.40 (1H, d, J=8.5 Hz), 7.31-7.25 (3H, m), 6.99 (1H, d, J=7.0 Hz), 5.18 (1H, s), 4.56-4.55 (1H, d, J=8.0 Hz), 4.16-4.07 (2H, m), 2.84-2.80 (1H, m), 2.26 (3H, s), 1.42-1.35 (2H, m), 0.88-0.84 (1H, m), 0.73 (3H, d, J=6.5 Hz), 0.59 (3H, d, J=6.5 Hz).

Step 2: (6R, 7S)-6-(4-bromophenyl)-7-isobutyl-8-methyl-6,7,8,9-tetrahydro-3H-pyrazolo [3,4-h] Isoquinoline (1b)

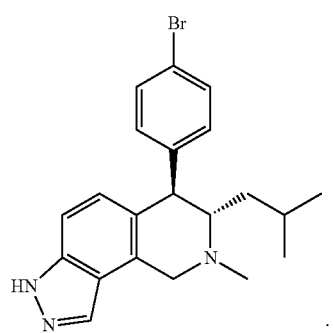

1b

Compound 1a (950 mg) was dissolved in anhydrous dichloromethane (5 ml), and then aluminum chloride (913 mg) was added at room temperature. The reaction was stirred at room temperature for 3 hours, to which an aqueous saturated sodium carbonate solution was poured and then ethyl acetate was added for extraction. The organic phase was separated, and the separated organic phase was washed twice with an aqueous diluted sodium chloride solution, dried over anhydrous sodium sulfate, filtered, and concentrated. The residue was purified by silica gel column chromatography to afford a yellow solid product 1b (900 mg). ¹H NMR (500 MHz, DMSO-d6) δ (ppm): 13.02 (1H, s), 8.05 (1H, s), 7.41 (2H, d, J=8.5 Hz), 7.26 (1H, d, J=8.5 Hz), 7.12 (2H, d, J=8.5 Hz), 6.80 (1H, d, J=9.0 Hz), 4.22 (1H, d), 3.99 (1H, d, J=4.0 Hz), 3.84 (1H, d), 2.90-2.87 (1H, m), 2.32 (3H, s), 1.80-1.73 (1H, m), 1.48-1.43 (1H, m), 0.99-0.93 (1H, m), 0.89 (3H, d, J=6.5 Hz), 0.81 (3H, d, J=6.5 Hz).

Step 3: (6R, 7S)-6-(4-bromophenyl)-7-isobutyl-8-methyl-3-(tetrahydro-2H-pyran-2-yl)-6,7,8,9-tetrahydro-3H-pyrazolo [3,4-h]isoquinoline (1c)

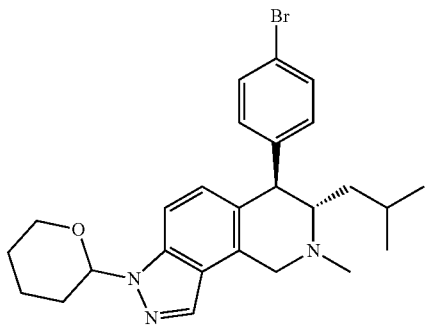

1c

Compound 1b (398 mg) was dissolved in dichloromethane (5 ml), and 3,4-dihydro-2H-pyran (252 mg) and p-toluenesulfonic acid monohydrate (228 mg) were added at room temperature. The reaction was stirred at room temperature for 3 hours. Then it was poured into an aqueous sodium carbonate aqueous solution and ethyl acetate was added for extraction. The organic phase was separated, and the separated organic phase was washed twice with an aqeuous diluted sodium chloride solution, dried over anhydrous sodium sulfate, filtered, and concentrated. The residue was purified by silica gel column chromatography to afford a yellow oily Product 1c (350 mg). ¹H NMR (500 MHz, DMSO-d6) δ (ppm): 8.10 (1H, s), 7.45-7.41 (3H, m), 7.12-7.09 (2H, m), 6.86 (1H, d, J=8.5 Hz), 5.77 (1H, d, J=9.0 Hz), 4.25-4.20 (1H, m), 4.05-4.01 (2H, m), 3.87-3.82 (2H, m), 3.73-3.67 (1H, m), 2.90-2.85 (1H, m), 2.31 (3H, s), 2.04-1.99 (1H, m), 1.95-1.92 (1H, m), 1.78-1.71 (2H, m), 1.57-1.56 (2H, m), 1.46-1.42 (1H, m), 0.99-0.93 (1H, m), 0.90-0.89 (3H, m), 0.81-0.73 (3H, m).

Step 4: tert-butyl 3-((4-(((6R, 7S)-7-isobutyl-8-methyl-3-(tetrahydro-2H-pyran-2-yl)-6,7,8,9-tetrahydro-3H-pyrazolo[3,4-h]isoquinolin-6-yl) phenyl) amino)azetidin-1-carboxylate (1d)

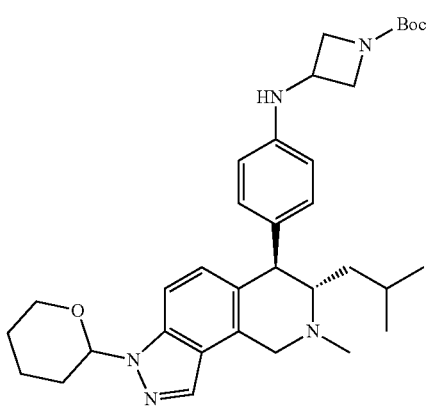

1d

Compound 1c (260 mg) was dissolved in 1,4-dioxane (5 ml), followed by tert-butyl 3-aminoazetidin-1-carboxylate (139 mg), Pd₂(dba)₃ (25 mg, CAS #: 51364-51-3), xantphos (47 mg, CAS #: 161265-03-8) and cesium carbonate (352 mg). The reaction was then refluxed under a nitrogen atmosphere overnight. Then, ethyl acetate and water were added for extraction. The organic phase was separated, and the separated organic phase was washed twice with an aqueous diluted sodium chloride solution, dried over anhydrous sodium sulfate, filtered, and concentrated. The residue was purified by silica gel column chromatography to afford a yellow oily product 1d (120 mg). ¹H NMR (500 MHz, DMSO-d6) δ (ppm): 8.15 (1H, s), 7.41-7.38 (1H, m), 6.86-6.83 (3H, m), 6.38-6.36 (2H, m), 6.05 (1H, d, J=8.0 Hz), 5.75 (1H, d, J=10.0 Hz), 4.23-4.13 (3H, m), 4.09-4.07 (1H, m), 3.86-3.79 (3H, m), 3.72-3.69 (1H, m), 3.67-3.57 (2H, m), 2.89-2.84 (1H, m), 2.42-2.37 (1H, m), 2.30 (3H, d, J=2.0 Hz), 2.04-2.01 (1H, m), 1.95-1.92 (1H, m), 1.76-1.70 (2H, m), 1.58-1.56 (2H, m), 1.37 (9H, s), 0.89-0.87 (3H, m), 0.79-0.77 (3H, m).

Step 5: N-(4-((6R, 7S)-7-isobutyl-8-methyl-6,7,8,9-tetrahydro-3H-pyrazolo [3,4-h]isoquinoline-6-yl) phenyl) azetidin-3-amine (1e)

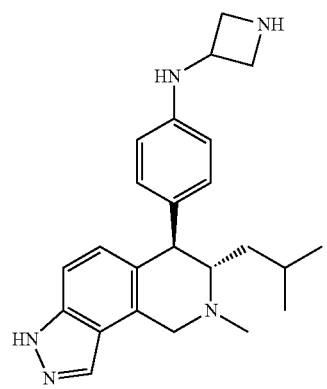

1e

Compound 1d (120 mg) was dissolved in dichloromethane (1.5 ml), and trifluoroacetic acid (0.5 ml) was added at room temperature. The reaction was performed at room temperature for 3 hours. Then it was poured into an aqueous saturated sodium carbonate solution and ethyl acetate was added for extraction. The organic phase was separated, and the separated organic phase was washed twice with an aqueous diluted sodium chloride solution, dried over anhydrous sodium sulfate, filtered, and concentrated to obtain a crude product 1e (81 mg). LCMS ESI (+): 390 (M+1)⁺.

Step 6: 1-(3-fluoropropyl)-N-(4-((6R, 7S)-7-isobutyl-8-methyl-6,7,8,9-tetrahydro-3H-pyrazolo [3,4-h]isoquinolin-6-yl) phenyl) azetidin-3-amine (1)

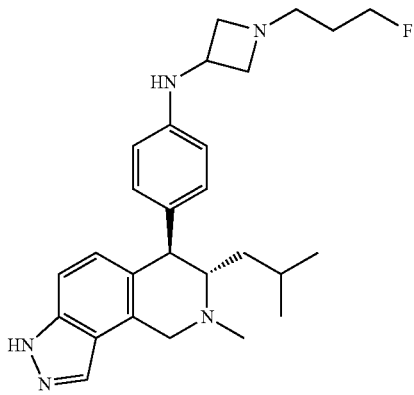

1

Compound 1e (81 mg) was dissolved in DMF (2 ml), followed by adding 1-bromo-3-fluoropropane (30 mg), diisopropylethylamine (54 mg), and sodium iodide (3 mg) at room temperature. The reaction was carried out at room temperature overnight. Then, ethyl acetate and water were added for extraction. The organic phase was separated, and the organic phase was washed twice with an aqueous diluted sodium chloride solution, dried over anhydrous sodium sulfate, filtered, and concentrated. The residue was purified by preparative silica gel chromatography to afford a yellow oily product 1 (16 mg). ¹H NMR (500 MHz, DMSO-d6) δ (ppm): 13.00 (1H, s), 9.87 (1H, s), 8.03 (1H, s), 7.22 (1H, d, J=7.5 Hz), 6.89 (2H, d, J=7.5 Hz), 6.76 (1H, d, J=8.5 Hz), 6.41 (2H, d, J=8.0 Hz), 6.06 (1H, s), 4.55 (1H, t, J=6.0 Hz), 4.45 (1H, t, J=6.0 Hz), 4.25-4.11 (3H, m), 3.80 (2H, s), 2.95-2.88 (3H, m), 2.36-2.33 (3H, m), 1.85-1.71 (4H, m), 1.48-1.43 (1H, m), 1.31-1.29 (1H, m), 0.87 (3H, d, J=6.0 Hz), 0.77 (3H, s). LCMS ESI(+): 450 (M+1).

Example 2

N-(3,5-difluoro-4-((6S, 7S)-7-isobutyl-8-methyl-6,7,8,9-tetrahydro-3H-pyrazolo [3,4-h]isoquinolin-6-yl) phenyl)-1-(3-fluoropropyl) azetidin-3-amine (2)

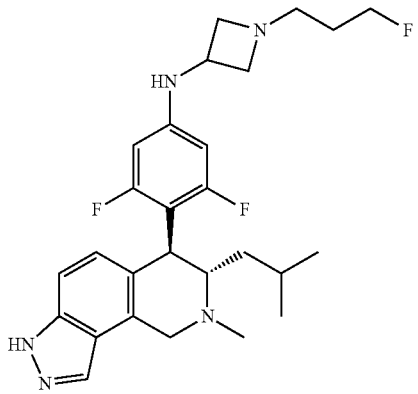

2

Step 1: (2S)-2-(((1H-indazol-4-yl) methyl) (methyl) amino)-1-(4-chloro-2,6-difluorophenyl)-4-methyl-pentane 1-ol (2a)

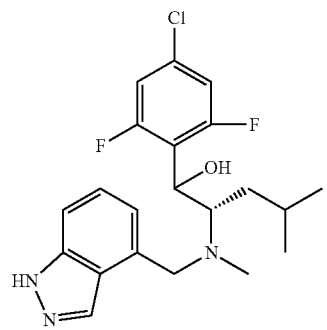

2a

Compound I-60-2 (1130 mg), 4-(chloromethyl)-1H-indazole (ADV947321888, available from Advanced Chem-Blocks Inc., 630 mg), potassium carbonate (2.5 g), and sodium iodide (54 Mg) were mixed in anhydrous DMF at room temperature. The reaction was stirred at room temperature overnight. Then, ethyl acetate and water were added for extraction. The organic phase was separated, and the separated organic phase was washed twice with an aqueous diluted sodium chloride solution, dried over anhydrous sodium sulfate, filtered, and concentrated. The residue was purified by silica gel column chromatography to afford a yellow solid product 2a (1660 mg). $^1$H NMR (500 MHz, dmso-d6) δ (in ppm): 12.98 (1H, s), 8.03 (1H, s), 7.40-7.41 (1H, d, J=5.0 Hz), 7.25-6.30 (3H, m), 7.02-7.03 (1H, d, J=5.0 Hz), 5.43-5.44 (1H, d, J=5.0 Hz), 5.01-5.05 (1H, m), 1.54-1.60 (1H, m), 1.35-1.42 (1H, m), 0.72-0.73 (3H, d, J=5.0 Hz), 0.59-0.63 (3H, m), 0.56-0.57 (3H, d, J=5.0 Hz).

Step 2: (6S, 7S)-6-(4-chloro-2,6-difluorophenyl)-7-isobutyl-8-methyl-6,7,8,9-tetrahydro-3H-pyrazolo [3,4-h]isoquinoline (2b)

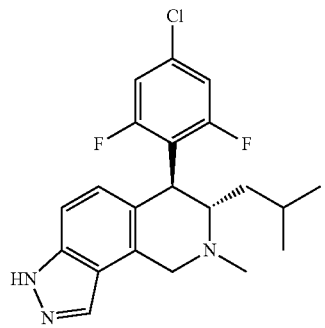

2b

The synthetic route for 1b was repeated, which starts from 2a. $^1$H NMR (500 MHz, dmso-d6) δ (in ppm): 13.02 (1H, s), 8.06 (1H, s), 7.32-7.34 (2H, d, J=10.0 Hz), 7.24-7.25 (1H, d, J=5.0 Hz), 6.68-6.70 (1H, d, J=10.0 Hz), 4.31-4.33 (1H, d, J=10.0 Hz), 4.25-4.28 (1H, d, J=15.0 Hz), 4.09-4.12 (1H, d, J=15.0 Hz), 3.20-3.26 (1H, m), 2.30 (3H, s), 1.72-1.80 (1H, m), 1.52-1.60 (1H, m), 0.83-0.89 (4H, m), 0.71-0.72 (3H, d, J=5.0 Hz). LCMS ESI(+): 390 (M+H).

Step 3: (6S, 7S)-6-(4-chloro-2,6-difluorophenyl)-7-isobutyl-8-methyl-3-(tetrahydro-2H-pyran-2-yl)-6,7,8,9-tetrahydro-3H-pyrazolo [3,4-h]isoquinoline (2c)

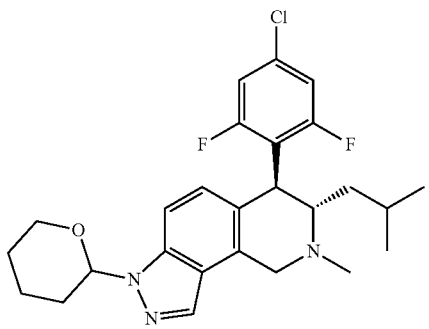

2c

The synthetic route for 2c was repeated, which starts from 2b. LCMS ESI(+): 474 (M+H).

Step 4: N-(3,5-difluoro-4-((6S, 7S)-7-isobutyl-8-methyl-3-(tetrahydro-2H-pyran-2-yl)-6,7, 8,9-tetrahydro-3H-pyrazolo [3,4-h]isoquinolin-6-yl) phenyl)-1-(3-fluoropropyl) azetidin-3-amine (2d)

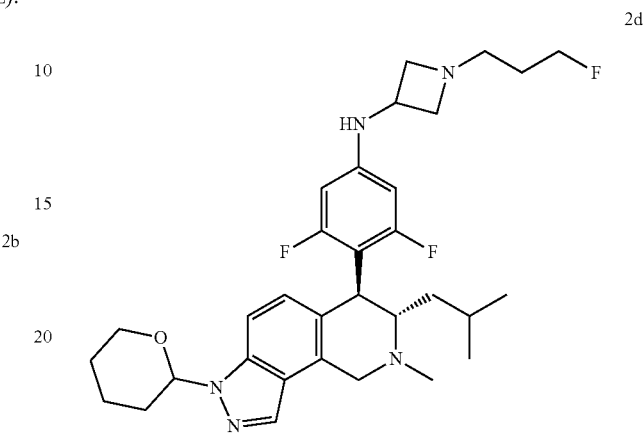

2d

Compound 2c (300 mg), 3-(3-fluoropropyl) azetidine (CAS: 1538772-53-0; 124 mg), Pd$_2$ (dba)$_3$ (29 mg), t-buXphos (CAS: 564483-19-8; 54 mg) and cesium carbonate (821 mg) were suspended in anhydrous toluene (5 ml). The mixture was refluxed under a nitrogen atmosphere for 12 hours. After cooling, an aqueous solution was added to quench the reaction and ethyl acetate was added for extraction. The collected ethyl acetate layer was then wash twice with an aqueous diluted sodium chloride solution, dried over anhydrous sodium sulfate, filtered, concentrated, and purified by column chromatography to afford 2d (210 mg). LCMS ESI (+): 570 (M+1)$^+$.

Step 5: N-(3,5-difluoro-4-((6S, 7S)-7-isobutyl-8-methyl-6,7,8,9-tetrahydro-3H-pyrazolo [3,4-h]isoquinolin-6-yl) phenyl)-1-(3-fluoropropyl) azetidin-3-amine (2)

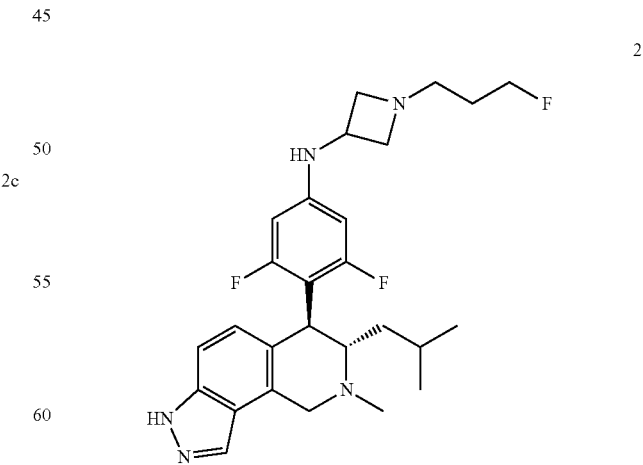

2

Compound 2d (215 mg) was dissolved in 15 ml of methanol, and then 5 ml of concentrated hydrochloric acid was added. The mixture was stirred at room temperature for 2 hours. Then, an aqueous saturated sodium bicarbonate solution was added and ethyl acetate was added for extraction. The collected ethyl acetate layer was then washed twice with an aqueous diluted sodium chloride solution, dried over anhydrous sodium sulfate, filtered, concentrated, and purified by column to afford product 2 (113 Mg). $^1$H NMR (500 MHz, dmso-d6) δ (in ppm): 12.96 (1H, s), 8.03 (1H, s), 7.21-7.23 (1H, d, J=10.0 Hz), 6.68-6.70 (1H, d, J=10.0 Hz), 6.59-6.60 (1H, d, J=5.0 Hz), 6.13-6.15 (2H, d, J=10.0 Hz), 4.50-4.52 (1H, t, J=5.0 Hz), 4.40-4.42 (1H, d, J=5.0 Hz), 4.21-4.24 (1H, m), 4.10-4.13 (1H, m), 3.93-3.80 (1H, m), 3.68 (2H, m), 3.51-3.55 (1H, m), 3.18 (1H, s), 2.82 (1H, s), 2.28 (3H, s), 1.91 (1H, s), 1.77 (1H, s), 1.63-1.72 (2H, m), 1.47-1.53 (1H, m), 0.89-0.95 (1H, m), 0.85-0.86 (3H, d, J=5.0 Hz), 0.71-0.72 (3H, d, J=5.0 Hz). LCMS ESI (+): 486 (M+1)$^+$.

Example 3

N-(3,5-difluoro-4-((6S, 7S)-7-isobutyl-8-methyl-6,7, 8,9-tetrahydro-3H-pyrazolo [3,4-h]isoquinolin-6-yl) phenyl)-1-(2,3-difluoropropyl) azetidin-3-amine (3)

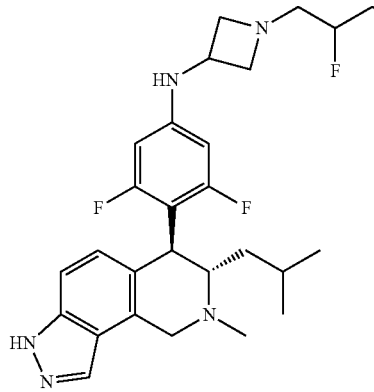

3

Step 1: N-(3,5-difluoro-4-((6S, 7S)-7-isobutyl-8-methyl-3-(tetrahydro-2H-pyran-2-yl)-6,7, 8,9-tetrahydro-3H-pyrazolo [3,4-h]isoquinolin-6-yl) phenyl)-1-(2,3-difluoropropyl) azetidin-3-amine (3a)

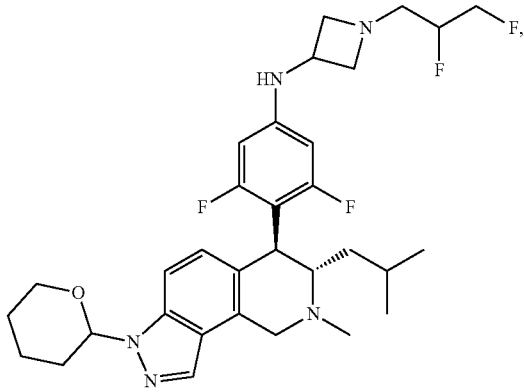 [SMILES: CC(C)C[C@H]1[C@H](c2c(F)cc(NC3CN(CC(F)CF)C3)cc2F)c2ccc3c(cnn3C3CCCCO3)c2CN1C]

The synthetic route for 2d was repeated, which started from 2c and I-100′-1. $^1$H NMR (500 MHz, DMSO-d6) δ 8.07 (s, 1H), 7.39 (dd, J=8.7, 4.7 Hz, 1H), 6.75 (d, J=8.7 Hz, 1H), 6.61 (d, J=6.6 Hz, 1H), 6.13 (d, J=12.4 Hz, 2H), 5.76 (dd, J=9.1, 3.6 Hz, 1H), 4.86-4.42 (m, 3H), 4.22 (t, J=13.8 Hz, 1H), 4.11 (t, J=13.8 Hz, 2H), 3.97 (q, J=6.6 Hz, 1H), 3.86 (d, J=11.6 Hz, 1H), 3.70 (d, J=8.7 Hz, 3H), 3.16 (s, 1H), 2.90 (s, 2H), 2.72 (dd, J=22.5, 5.4 Hz, 2H), 2.44-2.33 (m, 2H), 2.27 (s, 3H), 2.03 (d, J=12.3 Hz, 1H), 1.94 (d, J=13.0 Hz, 1H), 1.74 (s, 2H), 1.57 (s, 2H), 1.51 (d, J=11.8 Hz, 1H), 0.93 (s, 1H), 0.85 (d, J=6.7 Hz, 3H), 0.71 (d, J=6.5 Hz, 3H).

Step 2: N-(3,5-difluoro-4-((6S, 7S)-7-isobutyl-8-methyl-6,7,8,9-tetrahydro-3H-pyrazolo [3,4-h]isoquinolin-6-yl) phenyl)-1-(2,3-difluoropropyl) azetidin-3-amine (3)

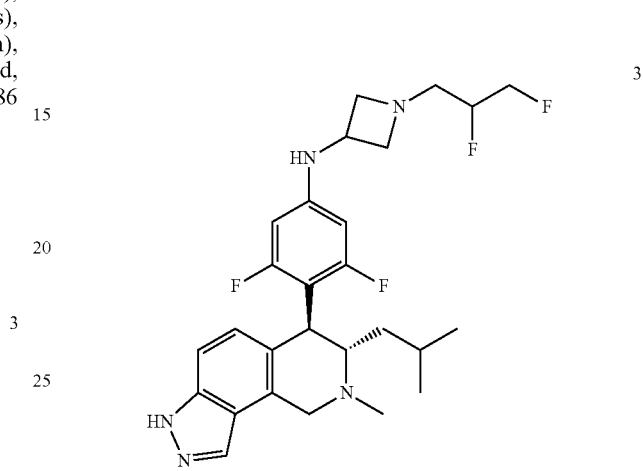

3

The synthetic route for 2 was repeated, which started from 3a. $^1$H NMR (500 MHz, DMSO-d$_6$) δ 12.98 (s, 1H), 8.02 (s, 1H), 7.21 (d, J=8.6 Hz, 1H), 6.69 (d, J=8.6 Hz, 1H), 6.62 (d, J=6.8 Hz, 1H), 6.13 (d, J=12.4 Hz, 2H), 4.82-4.44 (m, 3H), 4.22 (d, J=16.7 Hz, 1H), 4.13-4.05 (m, 2H), 3.96 (h, J=6.6 Hz, 1H), 3.72-3.66 (m, 2H), 3.18 (td, J=9.8, 3.8 Hz, 1H), 2.89 (t, J=6.6 Hz, 2H), 2.73 (d, J=5.4 Hz, 1H), 2.68 (d, J=5.4 Hz, 1H), 2.27 (s, 3H), 1.74 (dddd, J=13.1, 10.2, 6.3, 3.8 Hz, 1H), 1.49 (ddd, J=13.9, 9.7, 4.0 Hz, 1H), 0.91 (ddd, J=13.9, 9.7, 3.9 Hz, 1H), 0.85 (d, J=6.6 Hz, 3H), 0.71 (d, J=6.5 Hz, 3H). LCMS ESI (+): 504 (M+1)$^+$.

Example 4

N-(3,5-difluoro-4-((6S, 7S)-7-isobutyl-8-methyl-6,7, 8,9-tetrahydro-3H-pyrazolo [3,4-h]isoquinolin-6-yl) phenyl)-1-(3,3,3-trifluoropropyl) azetidin-3-amine (4)

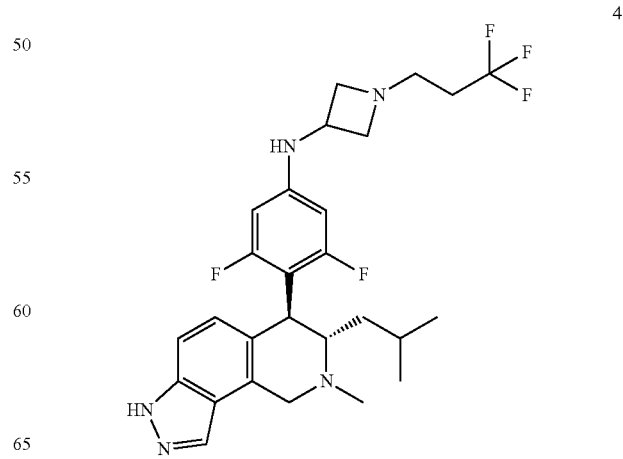

4

41

Step 1: N-(3,5-difluoro-4-((6S, 7S)-7-isobutyl-8-methyl-3-(tetrahydro-2H-pyran-2-yl)-6,7, 8,9-tetrahydro-3H-pyrazolo [3,4-h]isoquinolin-6-yl) phenyl)-1-(3,3,3-trifluoropropyl) azetidin-3-amine (4a)

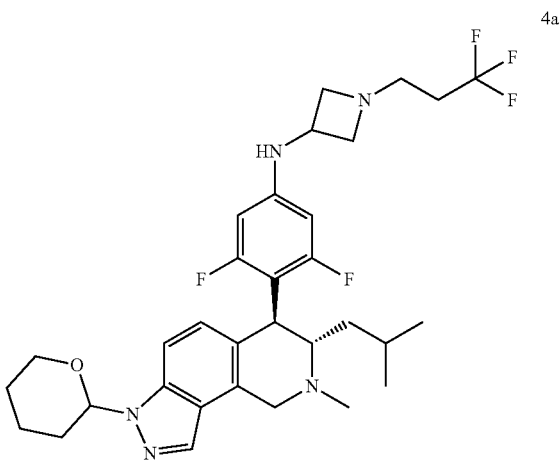 [SMILES: CC(C)C[C@H]1[C@H](c2c(F)cc(NC3CN(CCC(F)(F)F)C3)cc2F)c2ccc3c(cnn3C3CCCCO3)c2CN1C]

4a

The synthetic route for 2d was repeated, which started from 2c and I-100'-2. LCMS ESI (+): 606 (M+1)⁺.

Step 2: N-(3,5-difluoro-4-((6S, 7S)-7-isobutyl-8-methyl-6,7,8,9-tetrahydro-3H-pyrazolo [3,4-h]isoquinolin-6-yl) phenyl)-1-(3,3,3-trifluoropropyl) azetidin-3-amine (4)

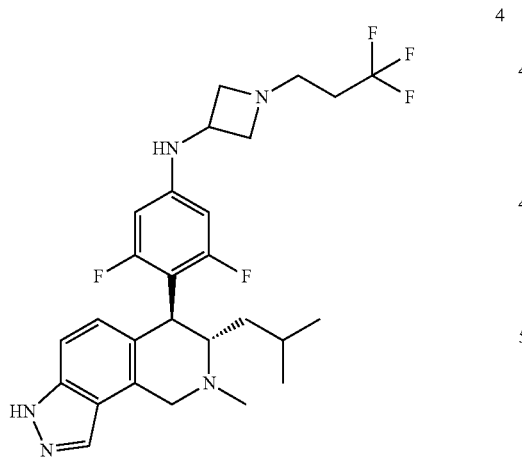

4

The synthetic route for 2 was repeated, which started from 4a. ¹H NMR (500 MHz, DMSO-d6, δ, ppm): 12.96 (s, 1H), 8.02 (s, 1H), 7.21 (d, J=8.5 Hz, 1H), 6.69 (d, J=8.5 Hz, 1H), 6.58 (d, J=5.0 Hz, 1H), 6.14 (d, J=12.0 Hz, 2H), 4.22 (d, J=16.5 Hz, 1H), 4.1-4.0 (m, 2H), 4.0-3.9 (m, 1H), 3.7-3.6 (m, 2H), 3.2-3.1 (m, 1H), 2.79 (t, J=6.5 Hz, 2H), 2.60 (t, J=7.5 Hz, 2H), 2.4-2.3 (m, 2H), 2.27 (s, 3H), 1.8-1.7 (m, 1H), 1.5-1.4 (m, 1H), 1.0-0.9 (m, 1H), 0.85 (d, J=6.5 Hz, 3H), 0.71 (d, J=6.5 Hz, 3H). LCMS ESI (+): 522 (M+1)⁺.

42

Example 5

N-(4-((6S, 7S)-7-cyclopropylmethyl-8-methyl-6,7,8,9-tetrahydro-3H-pyrazolo [3,4-h]isoquinolin-6-yl)-3,5-difluorophenyl)-1-(3-fluoropropyl) azetidin-3-amine (5)

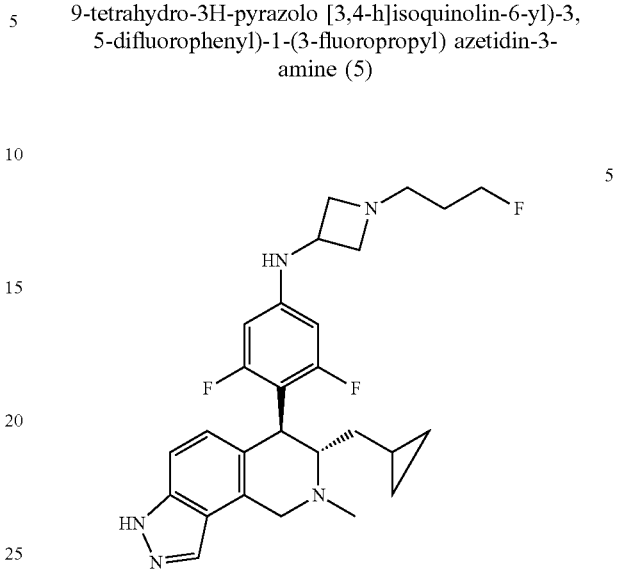

5

Step 1: (2S)-2-(((1H-indazol-4-yl) methyl) (methyl) amino)-1-(4-chloro-2,6-difluorophenyl)-3-cyclopropyl propan-1-ol (5a)

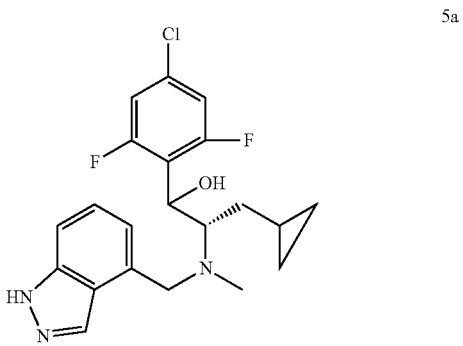 [SMILES: CN(Cc1cccc2[nH]ncc12)[C@@H](CC1CC1)C(O)c1c(F)cc(Cl)cc1F]

5a

The synthetic route for 2a was repeated, which started from I-60-3. ¹H NMR (500 MHz, DMSO-d6) δ 13.24 (s, 1H), 8.34 (d, J=1.3 Hz, 1H), 7.64 (d, J=8.3 Hz, 1H), 7.49 (t, J=8.1 Hz, 3H), 7.24 (d, J=6.9 Hz, 1H), 5.55 (d, J=3.5 Hz, 1H), 5.20 (dd, J=9.1, 3.4 Hz, 1H), 4.38 (q, J=13.7 Hz, 2H), 3.46 (td, J=8.5, 5.4 Hz, 1H), 2.57 (s, 3H), 1.88-1.76 (m, 1H), 0.95 (ddd, J=13.7, 7.8, 5.3 Hz, 1H), 0.87-0.77 (m, 1H), 0.55 (tdd, J=8.9, 5.3, 3.9 Hz, 1H), 0.48 (tq, J=9.0, 4.1 Hz, 1H), 0.16 (dq, J=9.3, 4.8 Hz, 1H), −0.00 (dq, J=9.4, 4.8 Hz, 1H). LCMS ESI (+): 406 (M+1)⁺.

Step 2: (6S, 7S)-6-(4-chloro-2,6-difluorophenyl)-7-cyclopropylmethyl-8-methyl-6,7,8,9-tetrahydro-3H-pyrazolo[3,4-h]isoquinoline (5b)

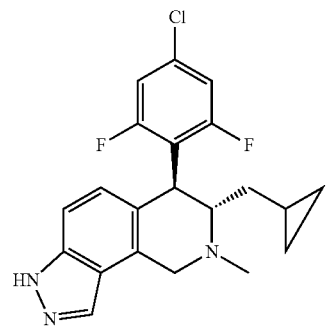

The synthetic route for 1b was repeated, which started from 5a. ¹H NMR (500 MHz, DMSO-d6) δ 13.30 (s, 1H), 8.31 (s, 1H), 7.54 (d, J=31.8 Hz, 3H), 6.96 (d, J=8.6 Hz, 1H), 4.71 (s, 1H), 4.50-4.23 (m, 2H), 3.36 (s, 1H), 2.70-2.50 (m, 3H), 1.89 (s, 1H), 1.23 (d, J=21.3 Hz, 1H), 1.03 (s, 1H), 0.61 (ddq, J=12.6, 8.6, 4.1 Hz, 2H), 0.25 (s, 1H), −0.01 (d, J=9.5 Hz, 1H). LCMS ESI (+): 388 (M+1)⁺.

Step 3: (6S, 7S)-6-(4-chloro-2,6-difluorophenyl)-7-(cyclopropylmethyl-8-methyl-3-(tetrahydro-2H-pyran-2-yl)-6,7,8,9-tetrahydro-3H-pyrazolo [3,4-h]isoquinoline (5c)

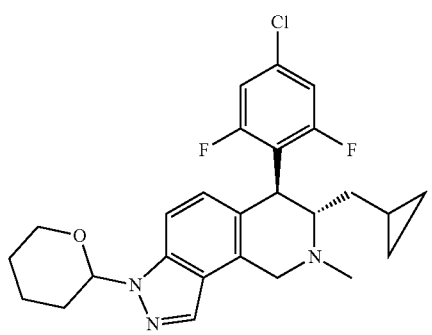

The synthetic route for 2c was repeated, which started from 5b. LCMS ESI (+): 472 (M+H).

Step 4: N-(4-((6S, 7S)-7-cyclopropylmethyl-8-methyl-3-(tetrahydro-2H-pyran-2-yl)-6,7,8,9-tetrahydro-3H-pyrazolo [3,4-h]isoquinolin-6-yl)-3,5-difluorophenyl)-1-(3-fluoropropyl) azetidin-3-amine (5d)

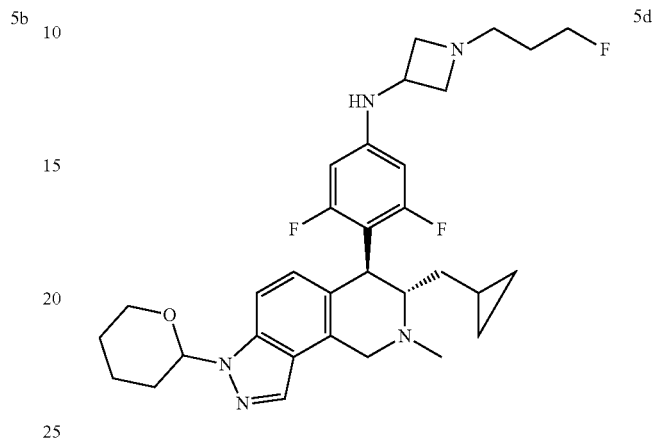

The synthetic route for 2d was repeated, which started from 5c and 3-(3-fluoropropyl) azetidine (CAS: 1538772-53-0). LCMS ESI(+): 568 (M+H).

Step 5: N-(4-((6S, 7S)-7-cyclopropylmethyl-8-methyl-6,7,8,9-tetrahydro-3H-pyrazolo [3,4-h]isoquinolin-6-yl)-3,5-difluorophenyl)-1-(3-fluoropropyl) azetidin-3-amine (5)

The synthetic route for 2 was repeated, which started from 5d. ¹H NMR (500 MHz, DMSO-d6) δ 12.96 (s, 1H), 8.02 (s, 1H), 7.22 (d, J=8.8 Hz, 1H), 6.67 (d, J=8.6 Hz, 1H), 6.13 (d, J=12.3 Hz, 2H), 5.33 (dd, J=5.5, 4.2 Hz, 1H), 4.51 (t, J=6.1 Hz, 1H), 4.41 (t, J=6.1 Hz, 1H), 4.25 (d, J=9.4 Hz, 1H), 4.14 (d, J=15.9 Hz, 1H), 3.93 (p, J=6.5 Hz, 1H), 3.86 (d, J=16.1 Hz, 1H), 3.65 (d, J=6.7 Hz, 2H), 2.77 (s, 3H), 2.37 (d, J=5.7 Hz, 3H), 1.69 (p, J=6.3 Hz, 1H), 1.64 (t, J=6.5 Hz, 1H), 1.47 (d, J=7.9 Hz, 2H), 1.30 (td, J=7.2, 4.4 Hz, 3H), 0.88-0.83 (m, 2H). LCMS ESI(+): 484 (M+H).

Example 6

N-(3,5-difluoro-4-((6S, 7S)-7-isobutyl-8-methyl-6,7,8,9-tetrahydro-3H-pyrazolo [3,4-h]isoquinolin-6-yl)phenyl)-1-propylazetidin-3-amine (6)

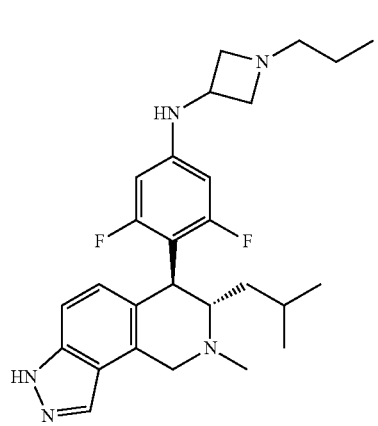

Step 1: tert-butyl 3-((3,5-difluoro-4-((6S, 7S)-7-isobutyl-8-methyl-3-(tetrahydro-2H-pyran-2-yl)-6,7,8,9-tetrahydro-3H-pyrazolo [3,4-h]isoquinolin-6-yl)phenyl) amino) azetidin-1-carboxylate (6a)

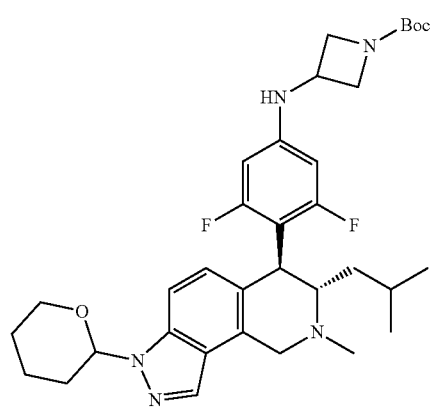

The synthetic route for 1d was repeated, which started from 2c and tert-butyl 3-aminoazetidin-1-carboxylate (CAS: 193269-78-2). LCMS ESI (+): 610 (M+1)$^+$.

Step 2: N-(3,5-difluoro-4-((6S, 7S)-7-isobutyl-8-methyl-6,7,8,9-tetrahydro-3H-pyrazolo [3,4-h]isoquinolin-6-yl) phenyl) azetidin-3-amine (6b)

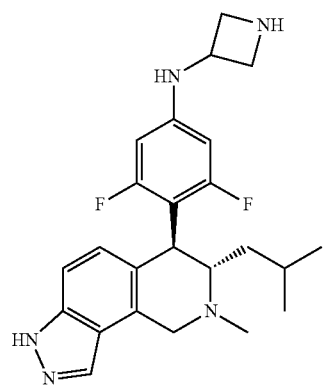

The synthetic route for 1e was repeated, which started from 6a. LCMS ESI (+): 426 (M+1)$^+$.

Step 3: N-(3,5-difluoro-4-((6S, 7S)-7-isobutyl-8-methyl-6,7,8,9-tetrahydro-3H-pyrazolo [3,4-h]isoquinolin-6-yl)phenyl)-1-propylazetidin-3-amine (6)

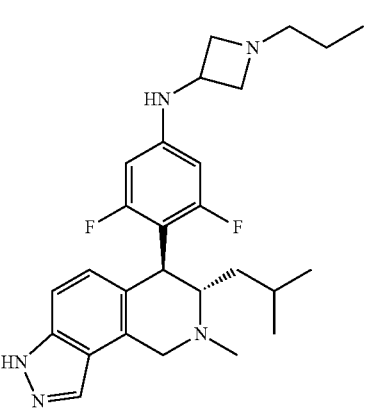

The synthetic route for 1 was repeated, which started from 6b and 1-bromopropane. LCMS ESI (+): 468 (M+1)$^+$.

47

Example 7

1-butyl-N-(3,5-difluoro-4-((6S, 7S)-7-isobutyl-8-methyl-6,7,8,9-tetrahydro-3H-pyrazolo [3,4-h]isoquinolin-6-yl) phenyl) azetidin-3-amine (7)

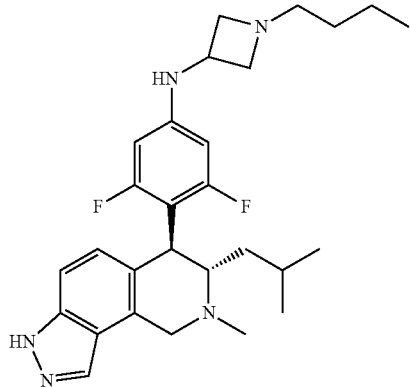

Step 1: 1-butyl-N-(3,5-difluoro-4-((6S, 7S)-7-isobutyl-8-methyl-6,7,8,9-tetrahydro-3H-pyrazolo [3,4-h]isoquinolin-6-yl) phenyl) azetidin-3-amine (7)

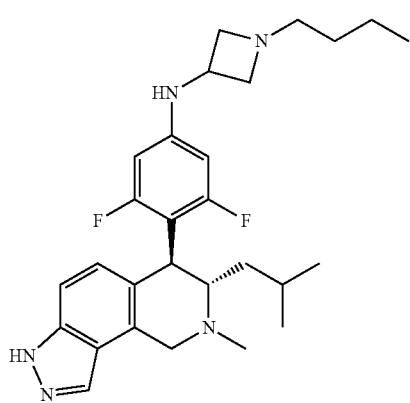

The synthetic route for 6 was repeated, which started from 6b and 1-bromobutane. LCMS ESI (+): 482 (M+1)⁺.

48

Example 8

N-(3,5-difluoro-4-((6S, 7S)-7-isobutyl-8-methyl-6,7,8,9-tetrahydro-3H-pyrazolo [3,4-h]isoquinolin-6-yl) phenyl)-1-isobutylazetidin-3-amine (8)

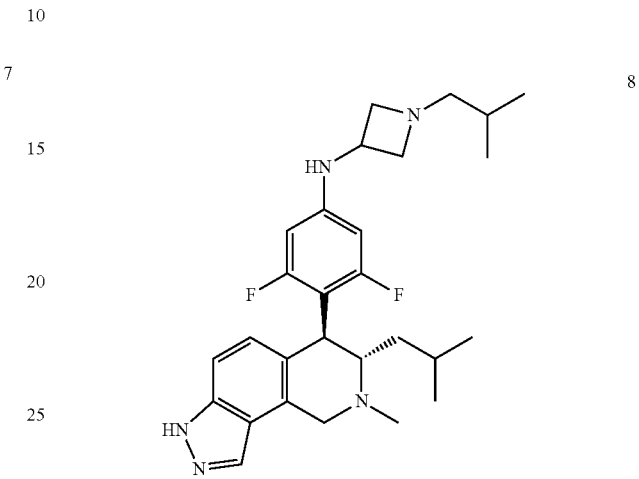

Step 1: N-(3,5-difluoro-4-((6S, 7S)-7-isobutyl-8-methyl-6,7,8,9-tetrahydro-3H-pyrazolo [3,4-h]isoquinolin-6-yl) phenyl)-1-isobutylazetidin-3-amine (8)

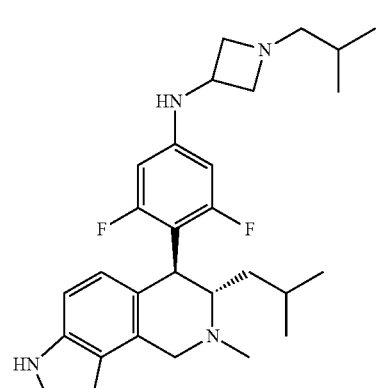

The synthetic route for 6 was repeated, which started from 6b and 1-bromo-2-methylpropane. LCMS ESI (+): 482 (M+1)⁺.

Example 9

N-(3,5-difluoro-4-((6S, 7S)-7-isobutyl-8-methyl-6,7,8,9-tetrahydro-3H-pyrazolo [3,4-h]isoquinolin-6-yl) phenyl)-1-pentylazetidin-3-amine (9)

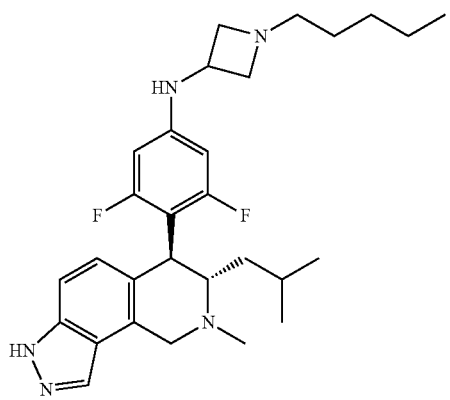

Step 1: N-(3,5-difluoro-4-((6S, 7S)-7-isobutyl-8-methyl-6,7,8,9-tetrahydro-3H-pyrazolo [3,4-h]isoquinolin-6-yl) phenyl)-1-pentylazetidin-3-amine (9)

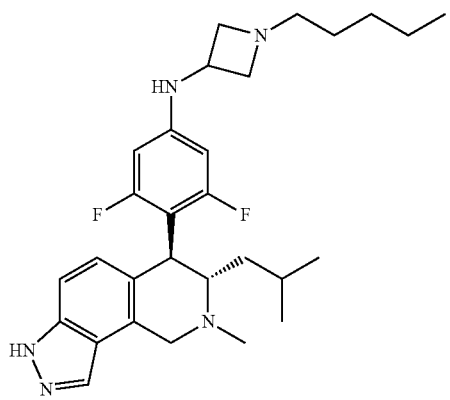

The synthetic route for 6 was repeated, which started from 6b and 1-bromo-pentane. LCMS ESI (+): 496 (M+1)+.

Example 10

(6S, 7S)-6-(2,6-difluoro-4-((1-(3-fluoropropyl) azetidin-3-yl) thio) phenyl)-7-isobutyl-8-methyl-6,7,8,9-tetrahydro-3H-pyrazolo [3,4-h]isoquinoline (10)

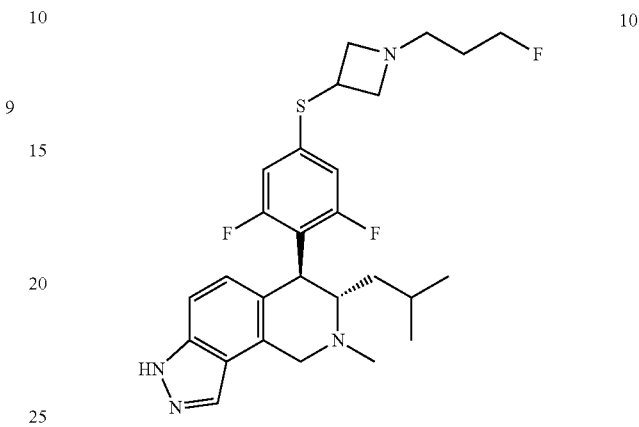

Step 1: tert-butyl 3-((3,5-difluoro-4-((6S, 7S)-7-isobutyl-8-methyl-3-(tetrahydro-2H-pyran-2-yl)-6,7,8,9-tetrahydro-3H-pyrazolo [3,4-h]isoquinolin-6-yl) phenyl) thio) azetidin-1-carboxylate (10a)

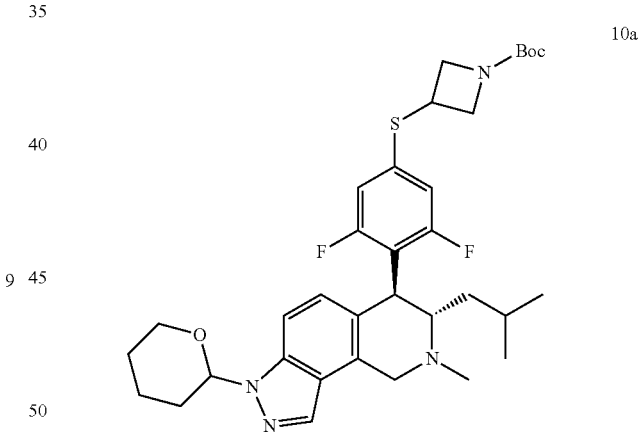

Coupling method according to the literature Org. Lett. 2004, vol. 6, 4587-5590: Compound 2c, tert-butyl 3-mercaptoazetidin-1-carboxylate (CAS: 941585-25-7), Pd$_2$(dba)$_3$, Xantphos and DIPEA were refluxed in anhydrous 1,6-dioxane. The reaction was then cooled. Water was added and then the mixture was extracted with ethyl acetate. The ethyl acetate layer was collected, then washed twice with an aqueous diluted sodium chloride solution, dried over anhydrous sodium sulfate, filtered, concentrated, and purified by column chromatograph to afford product 10a. LCMS ESI (+): 627 (M+1)+.

Step 2: (6S, 7S)-6-(4-(azetidin-3-ylthio)-2,6-difluorophenyl)-7-isobutyl-8-methyl-6,7, 8,9-tetrahydro-3H-pyrazolo [3,4-h]isoquinoline (10b)

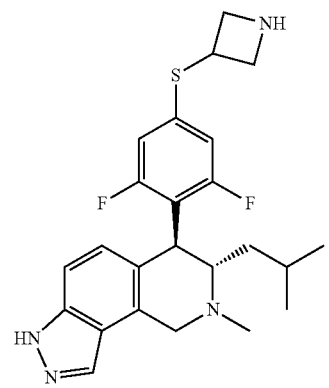

The synthetic route for 1e was repeated, which started from 10a. LCMS ESI (+): 443 (M+1)+.

Step 3: (6S, 7S)-6-(2,6-difluoro-4-((1-(3-fluoropropyl) azetidin-3-yl) thio) phenyl)-7-isobutyl-8-methyl-6,7,8,9-tetrahydro-3H-pyrazolo [3,4-h]isoquinoline (10)

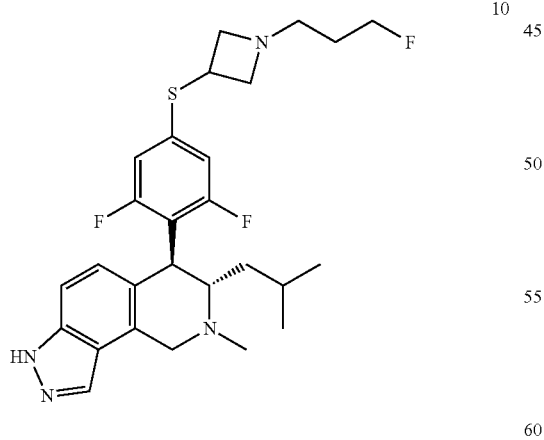

The synthetic route for 1 was repeated, which started from 10b and 1-bromo-3-fluoropropane. LCMS ESI (+): 503 (M+1)+.

Example 11

(6S, 7S)-6-(2,6-difluoro-4-((1-propyl) azetidin-3-yl) thio) phenyl)-7-isobutyl-8-methyl-6,7,8,9-tetrahydro-3H-pyrazolo [3,4-h]isoquinoline (11)

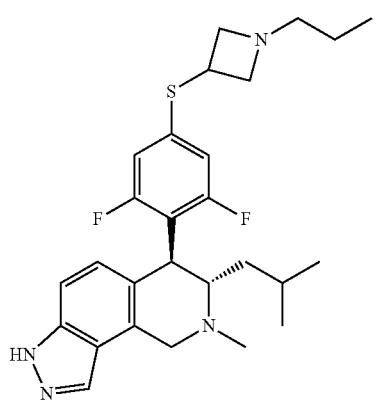

Step 1: (6S, 7S)-6-(2,6-difluoro-4-((1-propyl) azetidin-3-yl) thio) phenyl)-7-isobutyl-8-methyl-6,7,8,9-tetrahydro-3H-pyrazolo [3,4-h]isoquinoline (11)

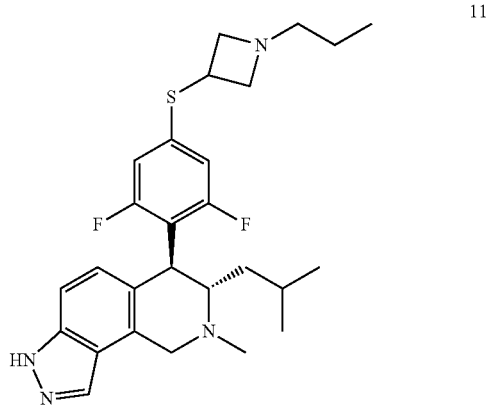 [SMILES: CCCN1CC(Oc2cc(F)c([C@@H]3c4ccc5[nH]ncc5c4CN(C)[C@H]3CC(C)C)c(F)c2)C1]

The synthetic route for 1 was repeated, which started from 10b and 1-bromo-propane. LCMS ESI (+): 485 (M+1)+.

Example 12

(6S, 7S)-6-(4-((1-butylazetidin-3-yl) thio)-2,6-difluorophenyl)-7-isobutyl-8-methyl-6,7,8,9-tetrahydro-3H-pyrazolo [3,4-h]isoquinoline (12)

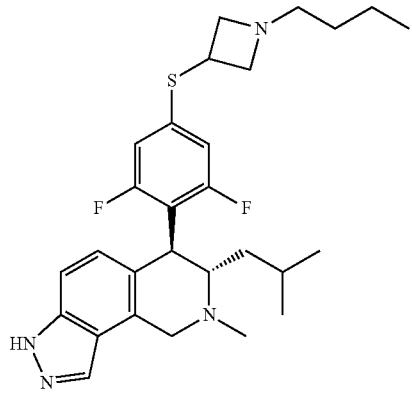

Step 1: (6S, 7S)-6-(4-((1-butylazetidin-3-yl) thio)-2,6-difluorophenyl)-7-isobutyl-8-methyl-6,7,8,9-tetrahydro-3H-pyrazolo [3,4-h]isoquinoline (12)

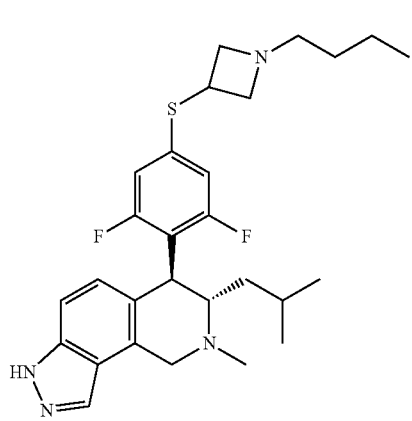

The synthetic route for 11 was repeated, which started from 10b and 1-bromobutane. LCMS ESI (+): 499 (M+1)$^+$.

Example 13

(6S, 7S)-6-(2,6-difluoro-4-((1-isobutylazetidin-3-yl) thio) phenyl)-7-isobutyl-8-methyl-6,7,8,9-tetrahydro-3H-pyrazolo [3,4-h]isoquinoline (13)

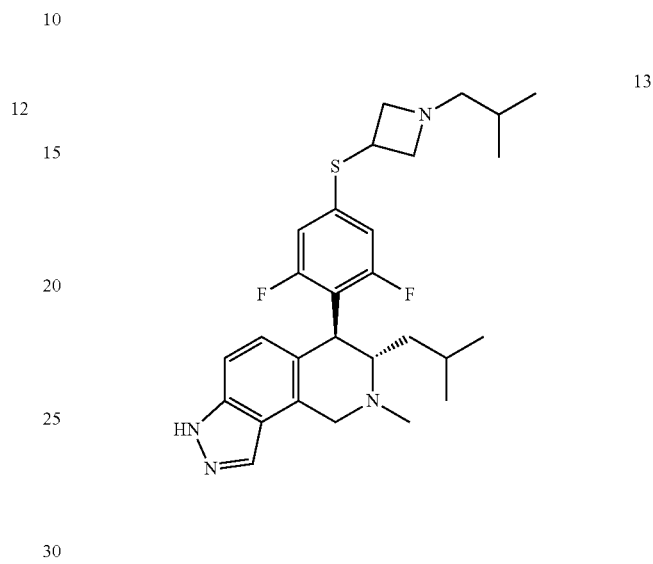

Step 1: (6S, 7S)-6-(2,6-difluoro-4-((1-isobutylazetidin-3-yl) thio) phenyl)-7-isobutyl-8-methyl-6,7,8,9-tetrahydro-3H-pyrazolo [3,4-h]isoquinoline (13)

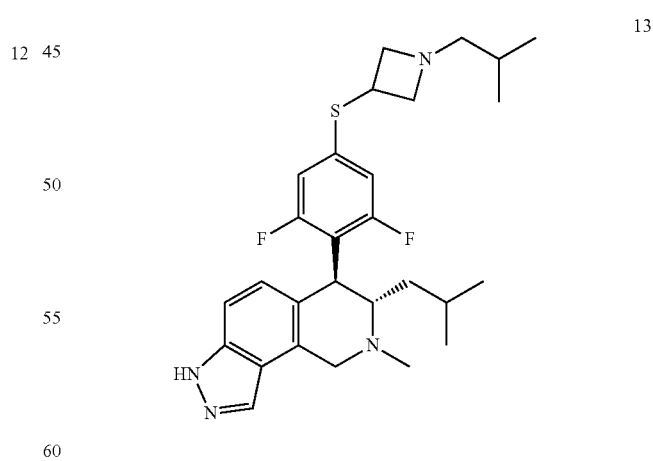

The synthetic route for 11 was repeated, which started from 10b and 1-bromo-2-methylpropane. LCMS ESI (+): 499 (M+1)$^+$.

Example 14

(6S, 7S)-6-(2,6-difluoro-4-((1-pentylazetidin-3-yl)thio) phenyl)-7-isobutyl-8-methyl-6,7,8,9-tetrahydro-3H-pyrazolo [3,4-h]isoquinoline (14)

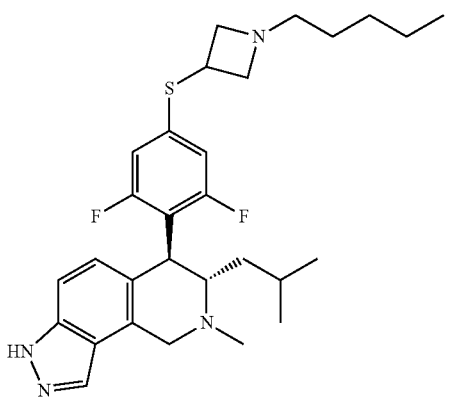

Step 1: (6S, 7S)-6-(2,6-difluoro-4-((1-pentylazetidin-3-yl) thio) phenyl)-7-isobutyl-8-methyl-6,7,8,9-tetrahydro-3H-pyrazolo [3,4-h]isoquinoline (14)

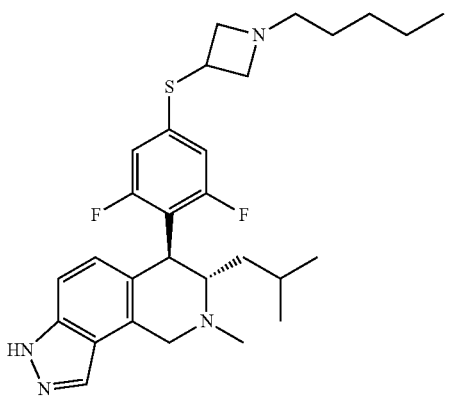

The synthetic route for 11 was repeated, which started from 10b and 1-bromo-pentane. LCMS ESI (+): 513 (M+1)$^+$.

Example 15

(6S, 7S)-6-(2,6-difluoro-4-((1-(3-fluoropropyl) azetidin-3-yl) oxy) phenyl)-7-isobutyl-8-methyl-6,7,8,9-tetrahydro-3H-pyrazolo [3,4-h]isoquinoline (15)

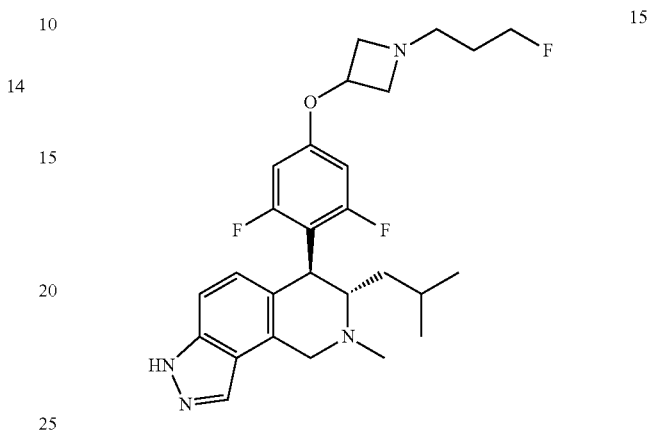

Step 1: tert-butyl 3-(3,5-difluoro-4-((6S, 7S)-7-isobutyl-8-methyl-3-(tetrahydro-2H-pyran-2-yl)-6,7,8,9-tetrahydro-3H-pyrazolo [3,4-h]isoquinolin-6-yl) phenoxy) azetidin-1-carboxylate (15a)

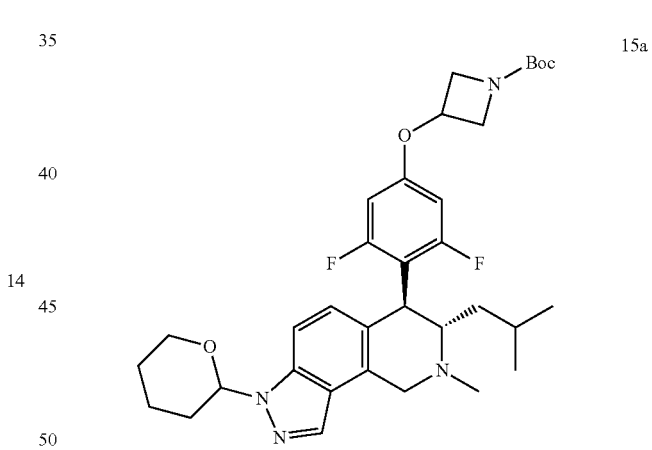

Compound 2c (100 mg), tert-butyl 3-hydroxyazetidin-1-carboxylate (CAS: 141699-55-0; 73 mg), Pd$_2$(dba)$_3$ (10 mg), t-buXphos (CAS: 564483-19-8; 9 mg) and cesium carbonate (202 mg) were suspended in anhydrous toluene (3 ml). The mixture was refluxed under a nitrogen atmosphere overnight. After cooling; water was added to quench the reaction and the mixture was extracted with ethyl acetate. The collected ethyl acetate layer was then washed twice with an aqueous diluted sodium chloride solution, dried over anhydrous sodium sulfate, filtered, concentrated, and purified to afford product 15a (63 mg). LCMS ESI (+): 611 (M+1)$^+$.

Step 2: (6S, 7S)-6-(4-(azetidin-3-yloxy)-2,6-difluorophenyl)-7-isobutyl-8-methyl-6,7,8,9-tetrahydro-3H-pyrazolo [3,4-h]isoquinoline (15b)

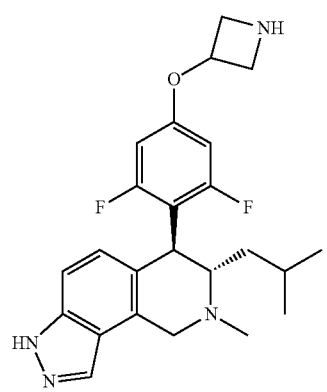

The synthetic route for 1e was repeated, which started from 15a. LCMS ESI (+): 427 (M+1)$^+$.

Step 3: (6S, 7S)-6-(2,6-difluoro-4-((1-(3-fluoropropyl) azetidin-3-yl) oxy) phenyl)-7-isobutyl-8-methyl-6,7,8,9-tetrahydro-3H-pyrazolo [3,4-h]isoquinoline (15)

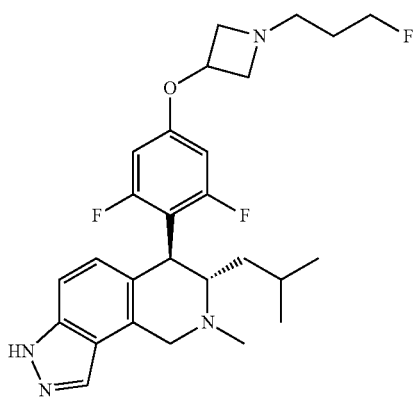

The synthetic route for 1 was repeated, which started from 15b and 1-bromo-3-fluoropropane. $^1$H NMR (500 MHz, dmso-d6) δ (in ppm): 12.99 (1H, s), 8.05 (1H, s), 7.22-7.24 (1H, d, J=10.0 Hz), 6.66-6.68 (1H, d, J=10.0 Hz), 6.59-6.61 (2H, d, J=10.0 Hz), 4.79-4.85 (1H, m), 4.49-4.52 (1H, t, J=5.0 Hz), 4.40-4.42 (1H, t, J=5.0 Hz), 4.20-4.26 (2H, m), 4.07-4.12 (1H, m), 3.70-3.74 (2H, m), 3.20-3.22 (1H, m), 3.17-3.18 (2H, d, J=5.0 Hz), 2.94-2.97 (2H, m), 2.29 (3H, s), 1.60-1.80 (3H, m), 1.49-1.56 (1H, m), 0.88-0.90 (1H, m), 0.84-0.86 (3H, d, J=10.0 Hz), 0.70-0.71 (3H, d, J=5.0 Hz). LCMS ESI (+): 487 (M+1)$^+$.

Example 16

(6S, 7S)-6-(2,6-difluoro-4-((1-propylazetidin-3-yl) oxy) phenyl)-7-isobutyl-8-methyl-6,7,8,9-tetrahydro-3H-pyrazolo [3,4-h]isoquinoline (16)

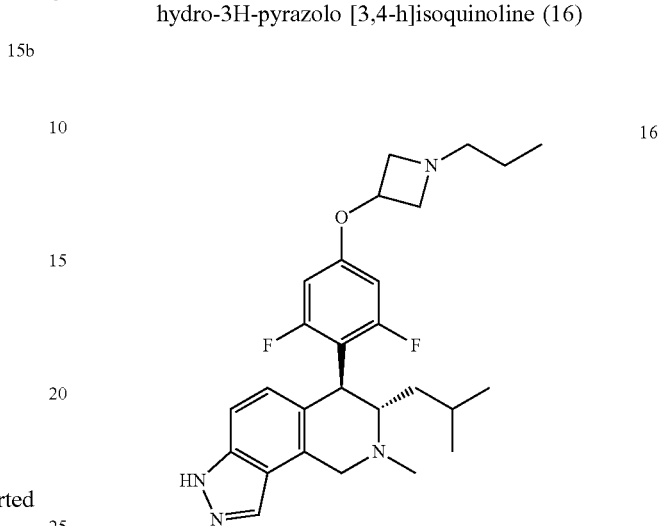

Step 1: (6S, 7S)-6-(2,6-difluoro-4-((1-propylazetidin-3-yl)oxy) phenyl)-7-isobutyl-8-methyl-6,7,8,9-tetrahydro-3H-pyrazolo [3,4-h]isoquinoline (16)

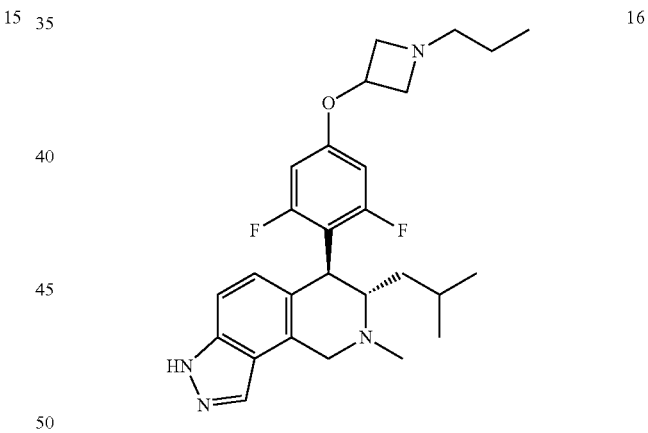

The synthetic route for 1 was repeated, which started from 15b and 1-bromopropane. $^1$H NMR (500 MHz, dmso-d6) δ (in ppm): 12.99 (1H, s), 8.05 (1H, s), 7.22-7.24 (1H, d, J=10.0 Hz), 6.66-6.68 (1H, d, J=10.0 Hz), 6.60-6.61 (2H, d, J=5.0 Hz), 4.78-4.83 (1H, m), 4.20-4.26 (2H, m), 4.08-4.11 (1H, m), 4.20-4.26 (2H, m), 3.69-3.73 (2H, m), 3.20-3.22 (1H, m), 3.17-3.22 (1H, m), 2.90-2.93 (2H, m), 2.36-2.39 (2H, m), 2.29 (3H, s), 1.70-1.78 (1H, m), 1.49-1.56 (1H, m), 1.26-1.34 (2H, m), 0.85-0.90 (1H, m), 0.83-0.85 (3H, d, J=10.0 Hz), 0.70-0.71 (3H, d, J=5.0 Hz). LCMS ESI (+): 469 (M+1)$^+$.

59
Example 17

(6S, 7S)-6-(2,6-difluoro-4-((1-isobutylazetidin-3-yl) oxy) phenyl)-7-isobutyl-8-methyl-6,7,8,9-tetrahydro-3H-pyrazolo [3,4-h]isoquinoline (17)

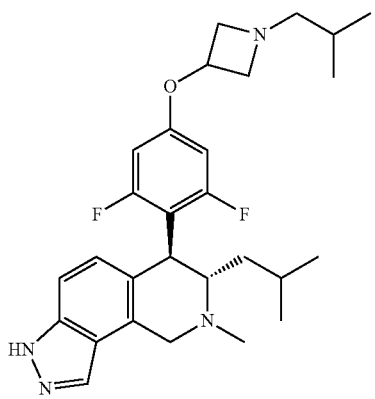

Step 1: (6S, 7S)-6-(2,6-difluoro-4-((1-isobutylazetidin-3-yl)oxy) phenyl)-7-isobutyl-8-methyl-6,7,8,9-tetrahydro-3H-pyrazolo [3,4-h]isoquinoline (17)

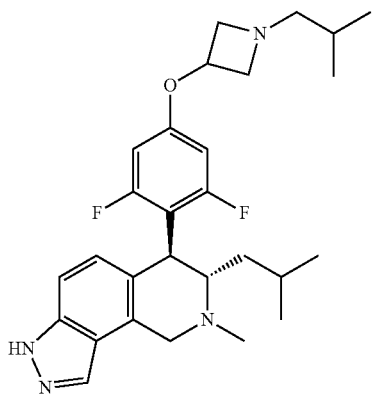

The synthetic route for 1 was repeated, which started from 15b and 1-bromo-2-methylpropane. $^1$H NMR (500 MHz, dmso-d6) δ (in ppm): 11.96 (1H, s), 8.00 (1H, s), 7.34-7.36 (1H, d, J=10.0 Hz), 6.75-6.77 (1H, d, J=10.0 Hz), 6.33-6.36 (2H, d, J=10.0 Hz), 4.94 (1H, s), 4.68 (1H, m), 4.41-4.45 (1H, m), 4.25 (1H, m), 3.60 (1H, m), 3.41 (2H, m), 3.04-3.14 (6H, m), 2.55-2.64 (4H, m), 1.71-1.84 (3H, m), 1.40 (9H, m), 0.96-0.98 (6H, d, J=10.0 Hz), 0.88-0.90 (3H, d, J=10.0 Hz), 0.75-0.76 (3H, d, J=5.0 Hz). LCMS ESI (+): 483 (M+1)$^+$.

60
Example 18

(6S, 7S)-6-(4-((1-butylazetidin-3-yl) oxy) phenyl)-7-isobutyl-8-methyl-6,7,8, 9-tetrahydro-3H-pyrazolo [3,4-h]isoquinoline (18)

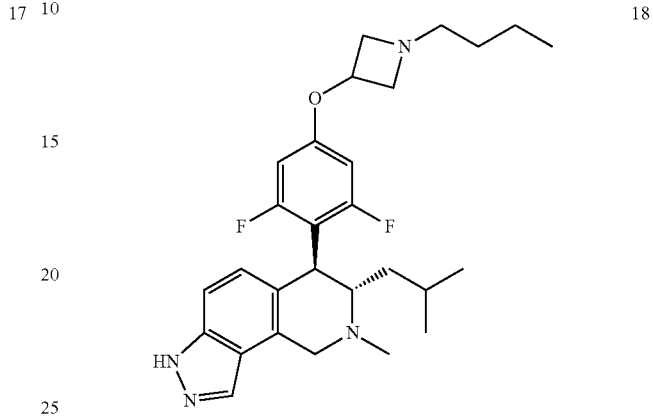

Step 1: (6S, 7S)-6-(4-((1-butylazetidin-3-yl) oxy) phenyl)-7-isobutyl-8-methyl-6,7,8, 9-tetrahydro-3H-pyrazolo [3,4-h]isoquinoline (18)

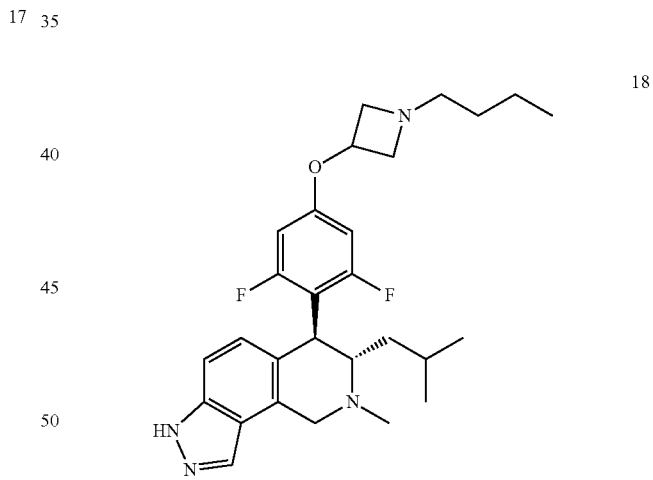

The synthetic route for 1 was repeated, which started from 15b and 1-bromo-butane. $^1$H NMR (500 MHz, dmso-d6) δ (in ppm): 12.99 (1H, s), 8.04 (1H, s), 7.22-7.24 (1H, d, J=10.0 Hz), 6.65-6.67 (1H, d, J=10.0 Hz), 6.60-6.62 (2H, d, J=10.0 Hz), 4.80-4.87 (1H, m), 4.20-4.28 (2H, m), 4.08-4.11 (1H, m), 3.87 (2H, m), 3.20 (3H, m), 2.55 (2H, m), 2.29 (3H, s), 1.71-1.76 (1H, m), 1.50-1.54 (1H, m), 1.29-1.32 (4H, m), 0.83-0.87 (6H, d, J=10.0 Hz), 0.70-0.71 (3H, d, J=5.0 Hz). LCMS ESI (+): 483 (M+1)$^+$.

Example 19

(6S, 7S)-6-(4-((1-pentylazetidin-3-yl) oxy) phenyl)-7-isobutyl-8-methyl-6,7,8,9-tetrahydro-3H-pyrazolo [3,4-h]isoquinoline (19)

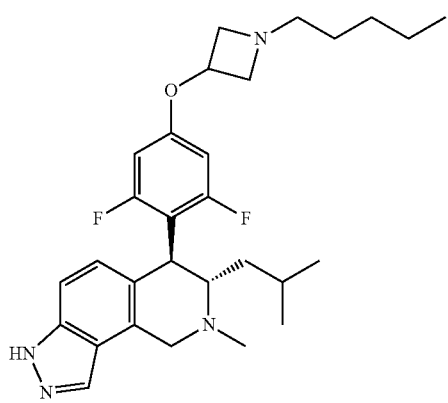

Step 1: (6S, 7S)-6-(4-((1-pentylazetidin-3-yl) oxy) phenyl)-7-isobutyl-8-methyl-6,7,8,9-tetrahydro-3H-pyrazolo [3,4-h]isoquinoline (19)

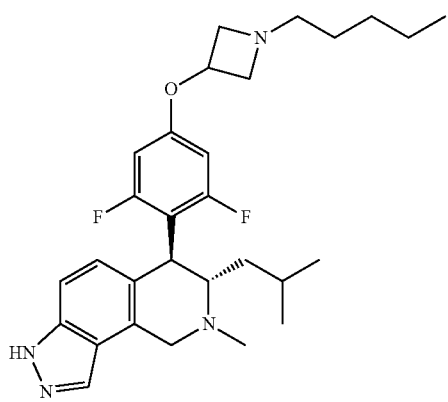

The synthetic route for 1 was repeated, which started from 15b and 1-bromo-pentane. $^1$H NMR (500 MHz, dmso-d6) δ (in ppm): 12.08 (1H, s), 8.01 (1H, s), 7.28-7.30 (1H, d, J=10.0 Hz), 6.78-6.79 (1H, d, J=5.0 Hz), 6.32-6.34 (2H, d, J=10.0 Hz), 4.95 (1H, s), 4.52-4.68 (1H, m), 4.22-4.44 (4H, m), 3.38-3.57 (3H, m), 2.80-2.86 (1H, m), 2.53 (3H, s), 2.04 (2H, s), 1.50-1.85 (4H, m), 1.31-1.35 (4H, m), 1.24-1.28 (4H, m), 0.86-0.92 (6H, m), 0.76-0.77 (3H, d, J=5.0 Hz). LCMS ESI (+): 497 (M+1)$^+$.

Example 20

(6S, 7S)-7-(cyclopropylmethyl)-6-(2,6-difluoro-4-((1-(3-fluoropropyl) azetidin-3-yl)oxy) phenyl)-8-methyl-6,7,8,9-tetrahydro-3H-pyrazolo [3,4-h]isoquinoline (20)

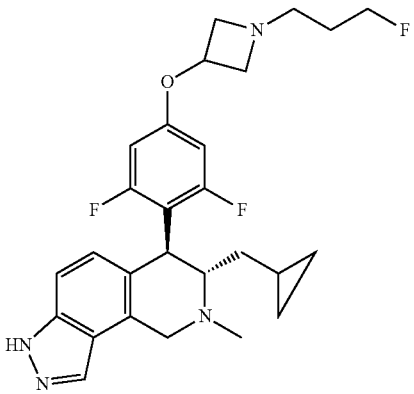

Step 1: tert-butyl 3-(4-((6S, 7S)-7-(isopropylmethyl)-8-methyl-3-(tetrahydro-2H-pyran-2-yl)-6,7,8,9-tetrahydro-3H-pyrazolo [3,4-h]isoquinolin-6-yl)-3,5-difluorophenoxy) azetidin-1-carboxylate (20a)

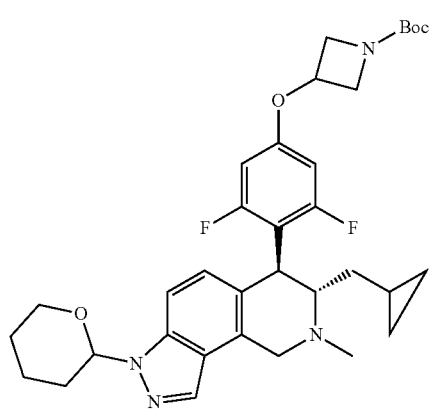

The synthetic route for 15a was repeated, which started from 5c and tert-butyl 3-hydroxylazetidin-1-carboxylate. LCMS ESI (+): 609 (M+1)$^+$.

Step 2: (6S, 7S)-6-(4-(azetidin-3-yloxy)-2,6-difluorophenyl)-7-cyclopropylmethyl-8-methyl-6,7,8,9-tetrahydro-3H-pyrazolo [3,4-h]isoquinoline (20b)

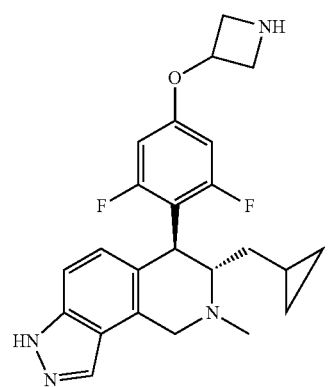

20b

The synthetic route for 1e was repeated, which started from 20a. LCMS ESI (+): 425 (M+1)+.

Step 3: (6S, 7S)-7-(cyclopropylmethyl)-6-(2,6-difluoro-4-((1-(3-fluoropropyl) azetidin-3-yl)oxy) phenyl)-8-methyl-6,7,8,9-tetrahydro-3H-pyrazolo [3,4-h] isoquinoline (20)

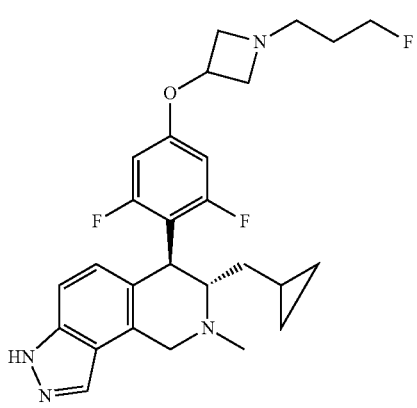

20

The synthetic route for 1 was repeated, which started from 20b and 1-bromo-3-fluoropropane. ¹H NMR (500 MHz, DMSO-d6) δ 12.99 (s, 1H), 8.04 (s, 1H), 7.23 (dd, J=8.8, 4.2 Hz, 1H), 6.71-6.55 (m, 3H), 5.52-5.36 (m, 2H), 4.81 (td, J=5.7, 3.6 Hz, 1H), 4.50 (t, J=6.0 Hz, 1H), 4.40 (t, J=6.1 Hz, 1H), 4.35 (d, J=9.0 Hz, 1H), 4.18-4.07 (m, 1H), 3.90 (d, J=16.2 Hz, 1H), 3.72 (qd, J=5.9, 4.9, 2.3 Hz, 2H), 2.97-2.87 (m, 3H), 2.38 (d, J=3.5 Hz, 3H), 2.23-2.16 (m, 1H), 2.05 (dt, J=13.7, 5.8 Hz, 1H), 1.68 (p, J=6.4 Hz, 1H), 1.63 (t, J=6.5 Hz, 1H), 1.60 (dd, J=6.1, 1.3 Hz, 2H), 1.02-0.95 (m, 0.5H), 0.80 (d, J=6.8 Hz, 0.5H), 0.38 (ddd, J=23.9, 8.8, 4.4 Hz, 1H), 0.00 (dt, J=9.3, 4.4 Hz, 0.5H), −0.28 (dt, J=9.3, 4.4 Hz, 0.5H). LCMS ESI (+): 485 (M+1)+.

Example 21

(6S, 7S)-7-cyclopropylmethyl-6-(2,6-difluoro-4-((1-propylazetidin-3-yl) oxy) phenyl)-8-methyl-6,7,8,9-tetrahydro-3H-pyrazolo [3,4-h]isoquinoline (21)

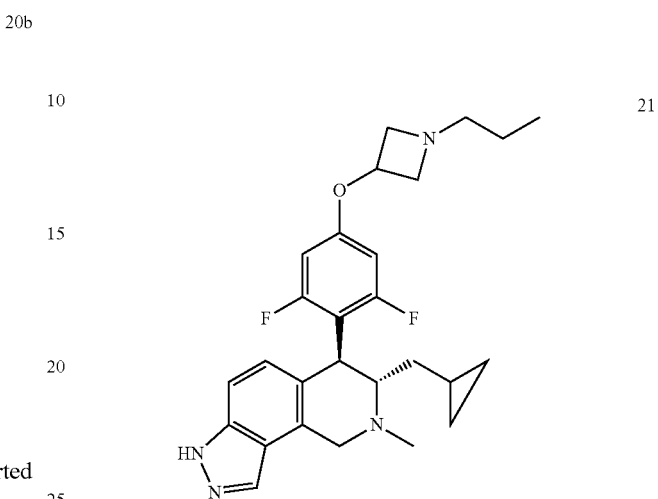

21

Step 1: (6S, 7S)-7-cyclopropylmethyl-6-(2,6-difluoro-4-((1-propylazetidin-3-yl) oxy) phenyl)-8-methyl-6,7,8,9-tetrahydro-3H-pyrazolo [3,4-h]isoquinoline (21)

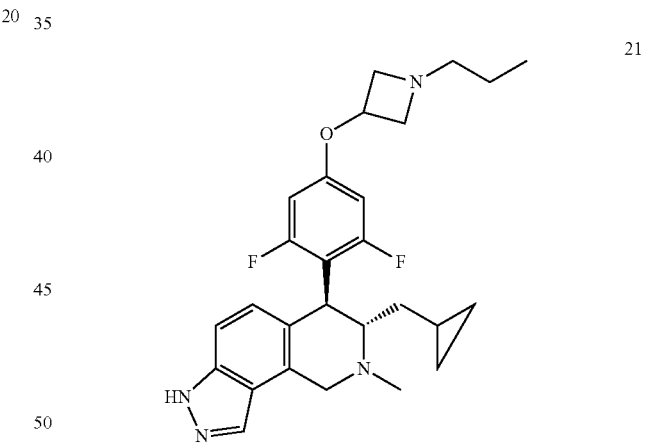

21

The synthetic route for 1 was repeated, which started from 20b and 1-bromopropane. ¹H NMR (500 MHz, DMSO-d6) δ 12.99 (s, 1H), 8.03 (s, 1H), 7.24 (dd, J=13.4, 8.8 Hz, 1H), 6.61 (dd, J=25.0, 9.9 Hz, 3H), 5.51-5.38 (m, 2H), 5.32 (t, J=4.7 Hz, 1H), 5.26 (d, J=3.1 Hz, 1H), 4.80 (q, J=5.5, 5.1 Hz, 1H), 4.35 (d, J=9.2 Hz, 1H), 4.16 (d, J=6.7 Hz, 1H), 4.12 (s, 1H), 3.90 (d, J=15.8 Hz, 1H), 3.80 (d, J=16.9 Hz, 1H), 3.70 (t, J=6.3 Hz, 2H), 2.90 (tt, J=5.5, 2.8 Hz, 2H), 2.40-2.34 (m, 4H), 2.18 (s, 1H), 2.09-2.02 (m, 1H), 2.01-1.95 (m, 1H), 1.60 (dd, J=5.9, 1.3 Hz, 1H), 1.29 (q, J=7.1 Hz, 2H), 1.16-1.11 (m, 1H), 0.89-0.83 (m, 3H). LCMS ESI (+): 467 (M+1)+.

Example 22

(6S, 7S)-7-cyclopropylmethyl-6-(2,6-difluoro-4-((1-isobutylazetidin-3-yl) oxy) phenyl)-8-methyl-6,7,8,9-tetrahydro-3H-pyrazolo [3,4-h]isoquinoline (22)

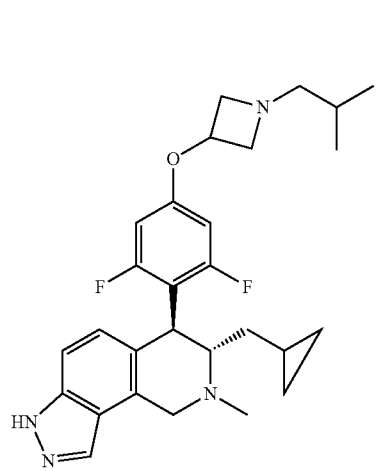

Step 1: (6S, 7S)-7-cyclopropylmethyl-6-(2,6-difluoro-4-((1-isobutylazetidin-3-yl) oxy) phenyl)-8-methyl-6,7,8,9-tetrahydro-3H-pyrazolo [3,4-h]isoquinoline (22)

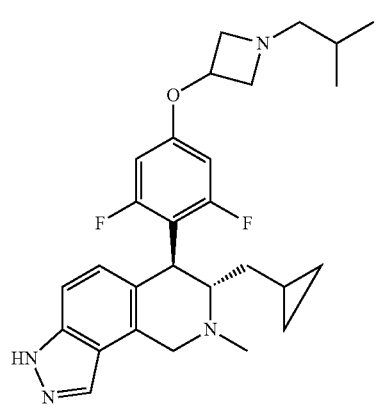

The synthetic route for 1 was repeated, which started from 20b and 1-bromo-2-methylpropane. LCMS ESI (+): 481 (M+1)$^+$.

Example 23

(6S, 7S)-6-(4-((1-butylazetidin-3-yl) oxy)-2,6-difluorophenyl)-7-cyclopropylmethyl-8-methyl-6,7,8,9-tetrahydro-3H-pyrazolo [3,4-h]isoquinoline (23)

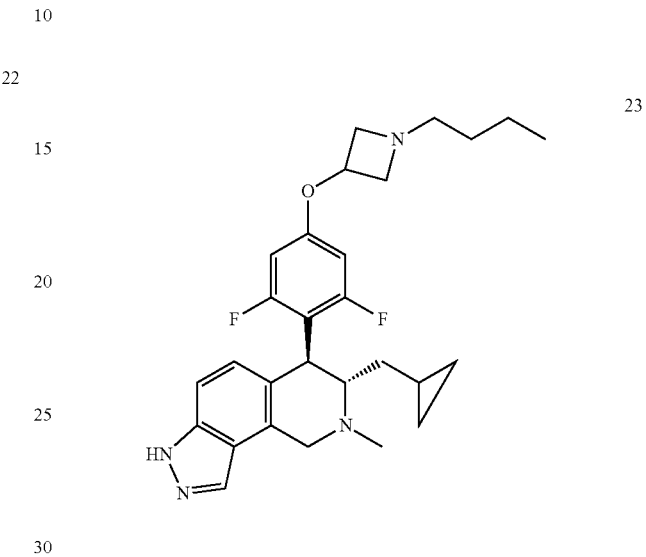

Step 1: (6S, 7S)-6-(4-((1-butylazetidin-3-yl) oxy)-2,6-difluorophenyl)-7-cyclopropylmethyl-8-methyl-6,7,8,9-tetrahydro-3H-pyrazolo [3,4-h]isoquinoline (23)

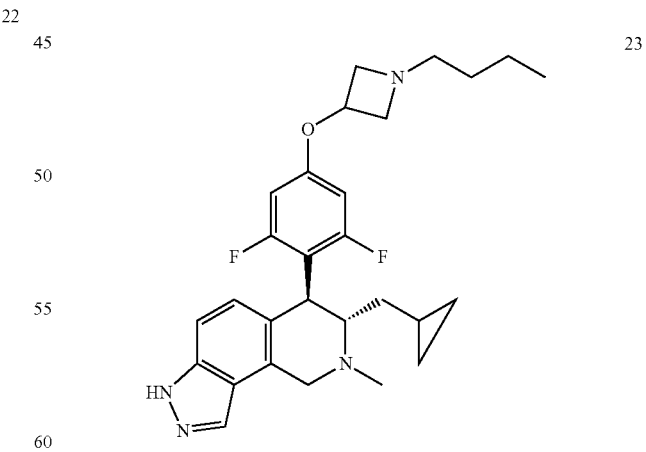

The synthetic route for 1 was repeated, which started from 20b and 1-bromo-butane. LCMS ESI (+): 481 (M+1)$^+$.

Example 24

(6S, 7S)-7-cyclopropylmethyl-6-(2,6-difluoro-4-((1-pentylazetidin-3-yl) oxy) phenyl)-8-methyl-6,7,8,9-tetrahydro-3H-pyrazolo [3,4-h]isoquinoline (24)

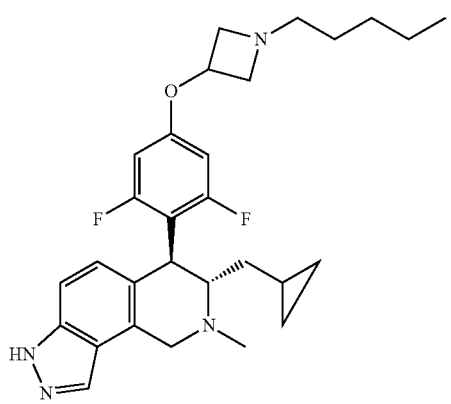

Step 1: (6S, 7S)-7-cyclopropylmethyl-6-(2,6-difluoro-4-((1-pentylazetidin-3-yl) oxy) phenyl)-8-methyl-6,7,8,9-tetrahydro-3H-pyrazolo [3,4-h]isoquinoline (24)

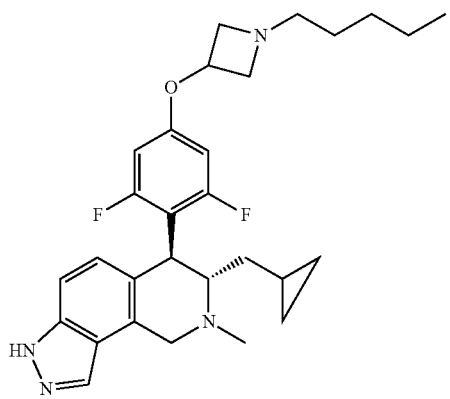

The synthetic route for 1 was repeated, which started from 20b and 1-bromo-pentane. LCMS ESI (+): 495 (M+1)$^+$.

Example 25

(6S, 7S)-7-cyclopropylmethyl-6-(2,6-difluoro-4-((1-(3-fluoropropyl) azetidin-3-yl) thio)) phenyl)-8-methyl-6,7,8,9-tetrahydro-3H-pyrazolo [3,4-h]isoquinoline (25)

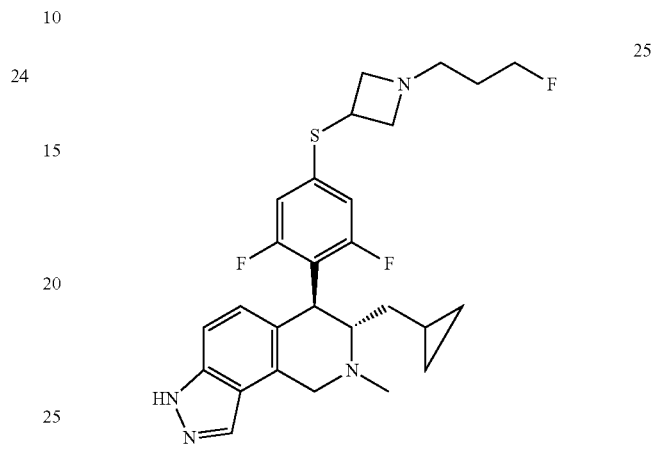

Step 1: tert-butyl 3-((4-((6S, 7S)-7-cyclopropylmethyl-8-methyl-3-(tetrahydro-2H-pyran-2-yl)-6,7,8,9-tetrahydro-3H-pyrazolo [3,4-h]isoquinolin-6-yl)-3,5-difluorophenyl) thio) azetidin-1-carboxylate (25a)

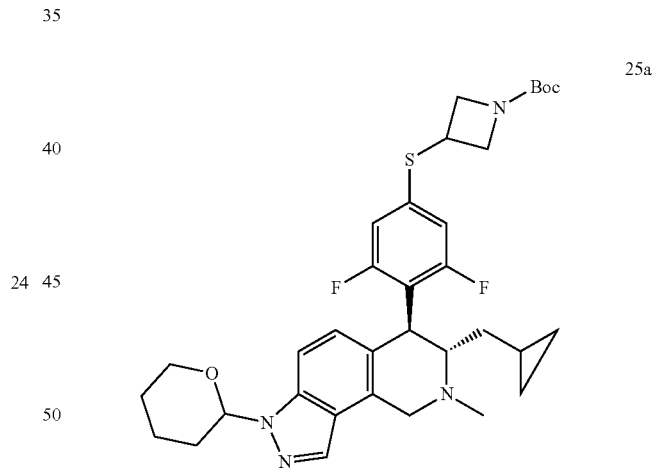

Coupling method according to the literature Org. Lett. 2004, vol. 6, 4587-5590: Compound 5c, tert-butyl 3-mercaptoazetidin-1-carboxylate (CAS: 941585-25-7), Pd$_2$(dba)$_3$, Xantphos and DIPEA were refluxed in anhydrous 1,6-dioxane. Ater cooling, water was added and then the mixture was extracted with ethyl acetate. The ethyl acetate layer was collected, then washed twice with an aqueous diluted sodium chloride solution, dried over anhydrous sodium sulfate, filtered, concentrated, and purified by column chromatograph to afford product 25a. LCMS ESI (+): 625 (M+1)$^+$.

Step 2: (6S, 7S)-6-(4-(azetidin-3-ylthio)-2,6-difluorophenyl)-7-cyclopropylmethyl-8-methyl-6,7,8,9-tetrahydro-3H-pyrazolo [3,4-h]isoquinoline (25b)

Example 26

(6S, 7S)-7-cyclopropylmethyl-6-(2,6-difluoro-4-((1-propylazetidin-3-yl) thio) phenyl)-8-methyl-6,7,8,9-tetrahydro-3H-pyrazolo [3,4-h]isoquinoline (26)

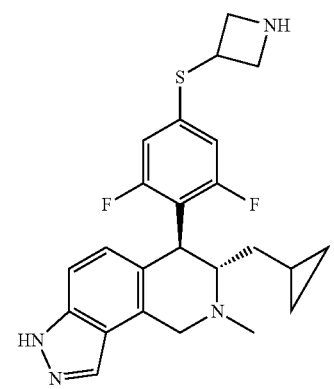

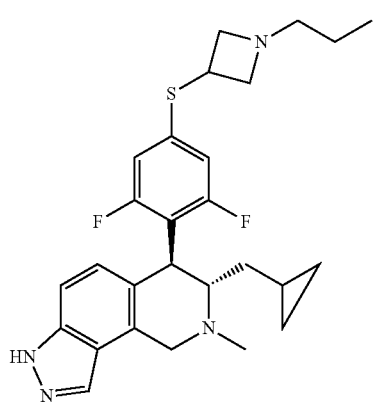

The synthetic route for 1e was repeated, which started from 25a. LCMS ESI (+): 441 (M+1)+.

Step 3: (6S, 7S)-7-cyclopropylmethyl-6-(2,6-difluoro-4-((1-(3-fluoropropyl) azetidin-3-yl) thio)) phenyl)-8-methyl-6,7,8,9-tetrahydro-3H-pyrazolo [3,4-h]isoquinoline (25)

Step 1: (6S, 7S)-7-cyclopropylmethyl-6-(2,6-difluoro-4-((1-propylazetidin-3-yl) thio) phenyl)-8-methyl-6,7,8,9-tetrahydro-3H-pyrazolo [3,4-h]isoquinoline (26)

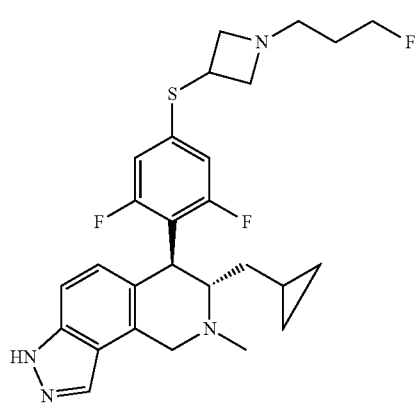

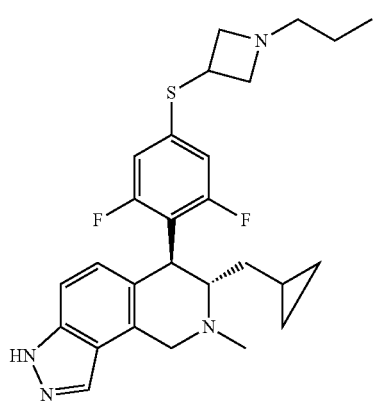

The synthetic route for 1 was repeated, which started from 25b and 1-bromo-3-fluoropropane. LCMS ESI (+): 501 (M+1)+.

The synthetic route for 1 was repeated, which started from 25b and 1-bromopropane. LCMS ESI (+): 483 (M+1)+.

71

Example 27

(6S, 7S)-6-(4-((1-butylazetidin-3-yl)thio)-2,6-difluorophenyl)-7-cyclopropylmethyl-8-methyl-6,7,8,9-tetrahydro-3H-pyrazolo [3,4-h]isoquinoline (27)

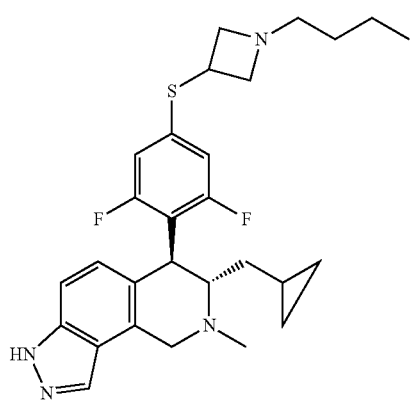

Step 1: (6S, 7S)-6-(4-((1-butylazetidin-3-yl)thio)-2,6-difluorophenyl)-7-cyclopropylmethyl-8-methyl-6,7,8,9-tetrahydro-3H-pyrazolo [3,4-h]isoquinoline (27)

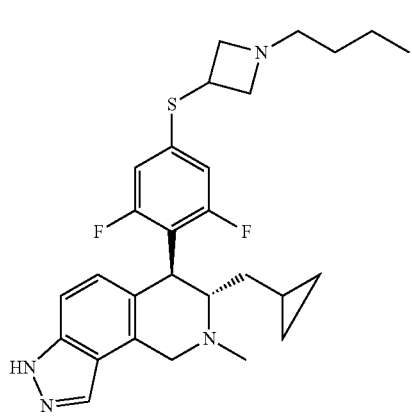

The synthetic route for 11 was repeated, which started from 25b and 1-bromobutane. LCMS ESI (+): 497 (M+1)⁺.

72

Example 28

(6S, 7S)-6-(4-((1-isobutylazetidin-3-yl) thio)-2,6-difluorophenyl)-7-cyclopropylmethyl-8-methyl-6,7,8,9-tetrahydro-3H-pyrazolo [3,4-h]isoquinoline (28)

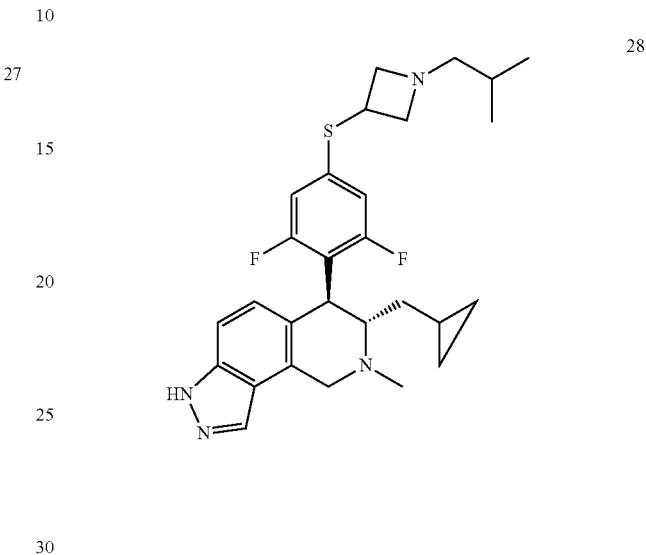

Step 1: (6S, 7S)-6-(4-((1-isobutylazetidin-3-yl) thio)-2,6-difluorophenyl)-7-cyclopropylmethyl-8-methyl-6,7,8,9-tetrahydro-3H-pyrazolo [3,4-h]isoquinoline (28)

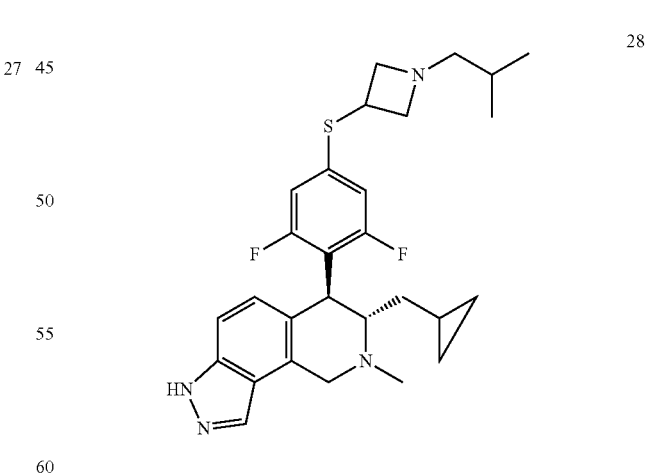

The synthetic route for 11 was repeated, which started from 25b and 1-bromo-2-methylpropane. LCMS ESI (+): 497 (M+1)⁺.

Example 29

(6S, 7S)-7-cyclopropylmethyl-6-(2,6-difluoro-4-((1-pentylazetidin-3-yl) thio) phenyl)-8-methyl-6,7,8,9-tetrahydro-3H-pyrazolo [3,4-h]isoquinoline (29)

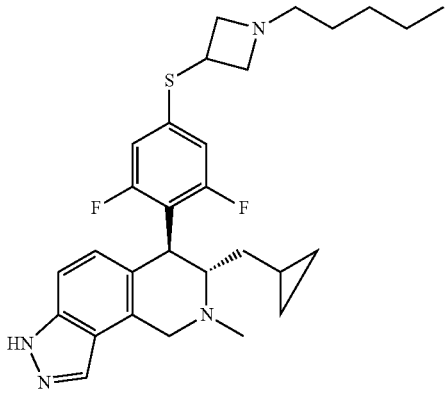

Step 1: (6S, 7S)-7-cyclopropylmethyl-6-(2,6-difluoro-4-((1-pentylazetidin-3-yl) thio) phenyl)-8-methyl-6,7,8,9-tetrahydro-3H-pyrazolo [3,4-h]isoquinoline (29)

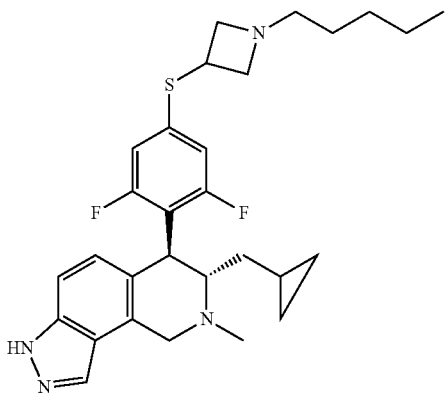

The synthetic route for 1 was repeated, which started from 25b and 1-bromo-pentane. LCMS ESI (+): 511 (M+1)$^+$.

Example 30

3-(3,5-difluoro-4-((6S, 7S)-7-isobutyl-8-methyl-6,7,8,9-tetrahydro-3H-pyrazolo [3,4-h]isoquinolin-6-yl) phenoxy) azetidin-1-aldehyde (30)

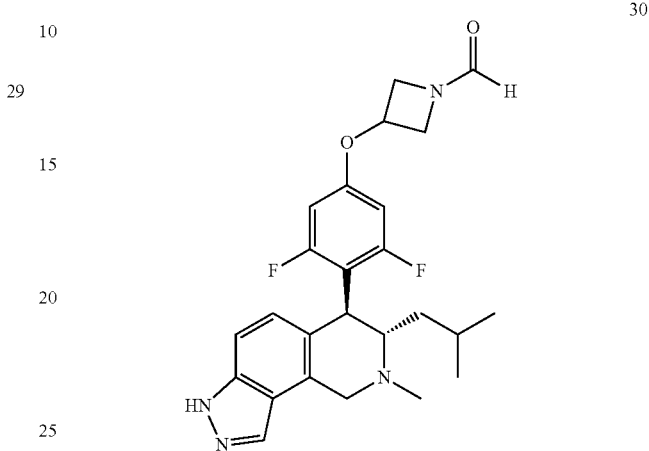

Step 1: 3-(3,5-difluoro-4-((6S, 7S)-7-isobutyl-8-methyl-6,7,8,9-tetrahydro-3H-pyrazolo [3,4-h]isoquinolin-6-yl) phenoxy) azetidin-1-aldehyde (30)

15b (727 mg), DIPEA (1.04 ml) and DMF (10 ml) were stirred at room temperature overnight. Water was added and the mixture was extracted with ethyl acetate. The ethyl acetate layer was collected, washed twice with an aqueous diluted sodium chloride solution, dried over anhydrous sodium sulfate, filtered, concentrated, and purified through a column chromatograph to afford 240 mg of product 30. $^1$H NMR (500 MHz, dmso-d6) δ (in ppm): 12.99 (1H, s), 8.04 (1H, s), 8.02 (1H, s), 7.22-7.24 (1H, d, J=10.0 Hz), 6.65-6.69 (3H, m), 5.11-5.16 (1H, m), 4.57-4.62 (1H, m), 4.33-4.38 (1H, m), 4.20-4.26 (2H, m), 4.07-4.11 (2H, m), 3.80-3.82 (2H, d, J=10.0 Hz), 2.29 (3H, s), 1.71-1.77 (1H, m), 1.49-1.56 (1H, m), 0.82-0.90 (4H, m), 0.70-0.71 (3H, d, J=5.0 Hz). LCMS ESI (+): 455 (M+1)$^+$.

Example 31

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) ethan-1-one (31)

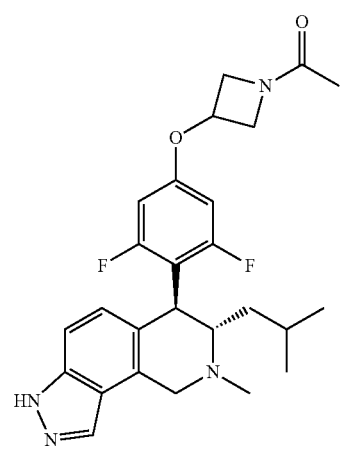

Step 1: 1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) ethan-1-one (31)

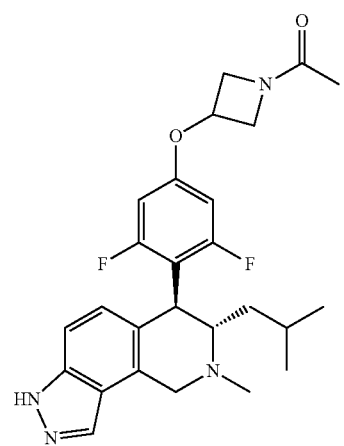

15b (1 equivalent), acetic anhydride (1.2 equivalents), DIPEA (3 equivalents), and DMF (20 volumes; relative to 15b) were stirred at room temperature overnight. Water was added and the mixture was extracted with ethyl acetate. The ethyl acetate layer was collected, washed twice with dilute sodium chloride aqueous solution, dried over anhydrous sodium sulfate, filtered, concentrated, and purified by column chromatography to afford product 31. LCMS ESI (+): 469 (M+1)⁺.

Example 32

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) propan-1-one (32)

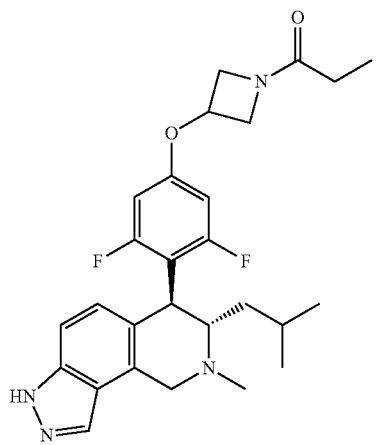

Step 1: 1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) propan-1-one (32)

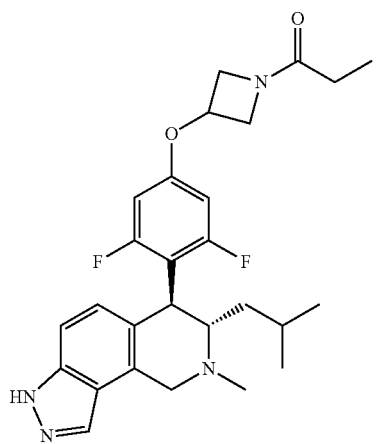

The synthetic route for 31 was repeated, which started from 15b and propionic anhydride. LCMS ESI (+): 483 (M+1)⁺.

Example 33

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) butan-1-one (33)

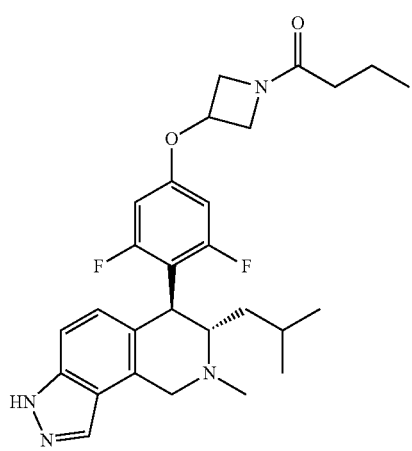

Step 1: 1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) butan-1-one (33)

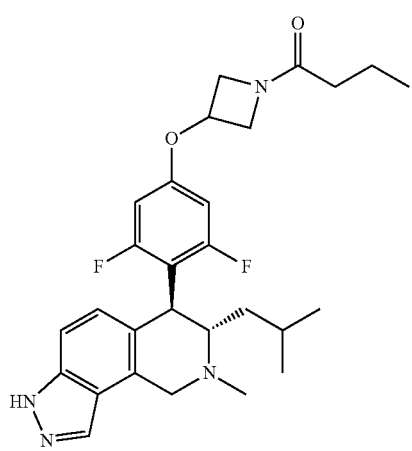

The synthetic route for 31 was repeated, which started from 15b and but anionic anhydride. LCMS ESI (+): 497 (M+1)⁺.

Example 34

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl)-2-methylpropan-1-one (34)

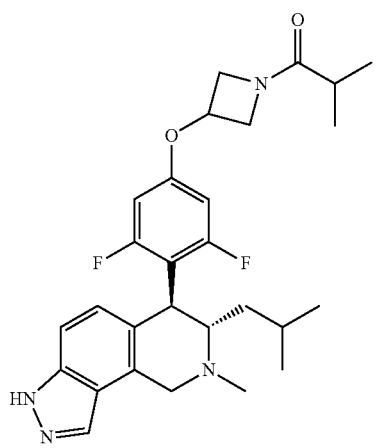

Step 1: 1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl)-2-methylpropan-1-one (1)

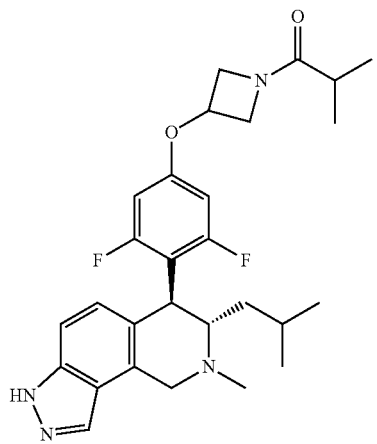

The synthetic route for 31 was repeated, which started from 15b and isobutanionic anhydride. LCMS ESI (+): 497 (M+1)⁺.

Evaluation of Pharmacological Activity

Assay 1. Effect of compounds of the present invention on degradation efficiency of estrogen receptors in MCF-7 and MCF-7/TAMR1 cells as measured by immunoblotting (Western Blot)

1. Experimental Materials:
1) Reagents: RIPA Lysate (ThermoFisher #89901), Protease Inhibitor (ThermoFisher #78438), BCA Quantitation Kit (ThermoFisher #23225), 4×LDS Sample Buffer (ThermoFisher #NP0007), 4-12% gradient precast gel (ThermoFisher #NW04120BOX), electrophoresis solution (ThermoFisher #B0002), transfer solution (ThermoFisher #BT00061), NC membrane (Merck #HATF00010), estrogen receptor (Cell Signaling Technology #8644), (3-actin (Cell Signaling Technology #4970), HRP-labeled murine secondary antibody (ThermoFisher #31430), HRP-labeled rabbit secondary antibody (ThermoFisher #31460), substrate color development kit (ThermoFisher #34076), TBST, PBS, skim milk powder 2) Instruments: Running glue tank (ThermoFisher #B1000), film transfer tank (ThermoFisher #NW2000), power supply (ThermoFisher #PS0301)

3) Cells: Human breast cancer cell lines MCF-7 and MCF-7/TAMR1 that are from cell bank of the Chinese Academy of Sciences and used directly.

2. Experimental Procedures:

1) 2 ml of MCF-7 or MCF-7/TAMR1 cells was added to a medium in a 6-well plate at a density of $0.6*10^6$ cells/ml in which the medium is DMEM high glucose medium supplemented with 10% FBS. The plate was incubated at 37° C. for 24 hours in a 5% $CO_2$ cell incubator.

2) To each culture, β-actin was added as an internal standard. Then different concentrations of corresponding compounds (10 nm or 100 nm of compounds of the present invention or 0.1% DMSO as a control) were added to the 6-well plate for incubating MCF-7 cells. The plate was incubated for 8 hours in a 5% $CO_2$ cell incubator.

3) Cells were harvested and extracted with with a volume volume of RIPA lysate that is 3-5 times of the volume of cells containing 1*protease inhibitor for total cellular proteins.

4) Immunoblotting analysis was carried out using equal amounts of cellular proteins.

Experimental Results

Figure 2:
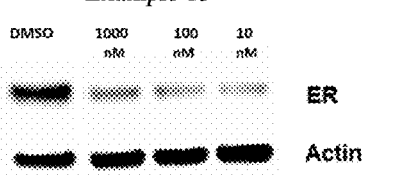
Figure 2:
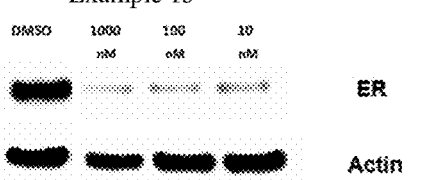
Figure 2:
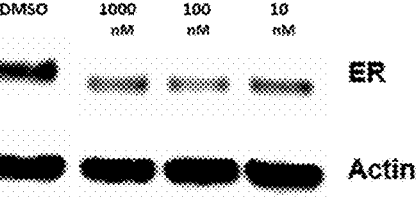
Figure 2:
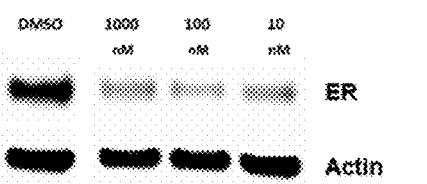
Figure 2:
Figure 2:
Figure 2:
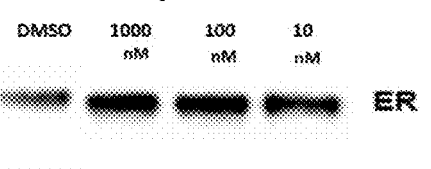
Figure 2:
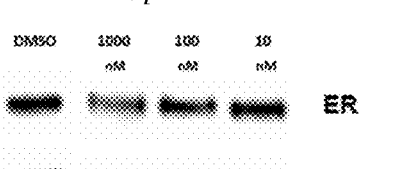
Figure 3:
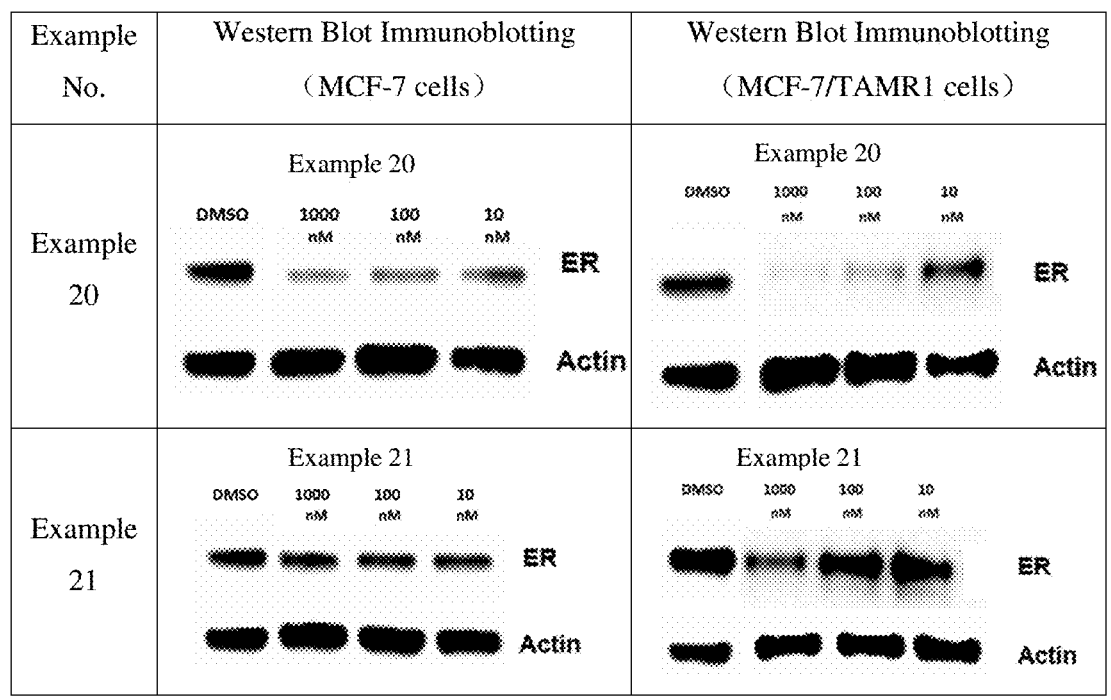

The experimental results were shown in FIGS. 1 to 3.

Assay 2: Inhibitory effect of compounds of the present invention on the growth of MCF-7 cells by a cell drug inhibition experiment 1. Experimental Materials 1) Reagents: DMEM high glucose medium (Lonza #12-604F), FBS (BI #04-00F1ACS), antibiotics (Thermofisher #15070063), bovine insulin (Western reagent #11070-73-8), trypsin (Thermofisher #25200-056), CellTiter-Glo reagent (Promega #G7571)

2) Instruments: American MD-M5 microplate reader 5;

3) Cells: as above.

2. Experimental Procedures:

1) 100 μl of MCF-7 cells was added to a medium in a white opaque 96-well plate at a density of 5000 cells/ml in which the medium is DMEM high-glucose medium supplemented with 10% FBS. The cells were cultured in a 5% $CO_2$ cell incubator at 37° C. for 24 hours.

2) Different concentrations of corresponding compounds were added to the 96-well plate for incubating MCF-7 cells. The cells were incubated for 10 days in a 5% $CO_2$ cell incubator.

3) To each well of MCF-7 cells, 100 μl of CellTiter-Glo reagent was added and then set aside at room temperature for 10 minutes. The chemiluminescence signal was read using an MD-M5 microplate reader, and the data was processed using GraphPad Prism to calculate $IC_{50}$ value.

3. Experimental Results:

| Examples | $IC_{50}$ value |
|---|---|
| Fulvestrant CAS: 129453-61-8 (positive control) | +++ |
| Example 1 | ++++ |
| Example 2 | +++++ |
| Example 3 | ++ |
| Example 4 | ++ |
| Example 5 | ++ |
| Example 6 | ++ |
| Example 7 | ++ |
| Example 8 | ++ |
| Example 9 | ++ |
| Example 10 | +++++ |
| Example 11 | +++++ |
| Example 12 | +++ |
| Example 13 | +++ |
| Example 14 | ++ |
| Example 15 | +++++ |
| Example 16 | +++++ |
| Example 17 | ++++ |
| Example 18 | ++ |
| Example 19 | ++ |
| Example 20 | ++ |
| Example 21 | ++ |
| Example 22 | ++ |
| Example 23 | ++ |
| Example 24 | ++ |
| Example 25 | +++ |
| Example 26 | +++ |
| Example 27 | ++ |
| Example 28 | ++ |
| Example 29 | ++ |
| Example 30 | +++++ |
| Example 31 | +++++ |
| Example 32 | +++++ |
| Example 33 | +++ |
| Example 34 | ++++ |

In the table:
++ represents: 1 μM < $IC_{50}$
+++ represensts: 0.01 μM < $IC_{50}$ ≤ 1 μM
++++ represensts: 1 nM < $IC_{50}$ ≤ 0.01 μM
+++++ represensts: $IC_{50}$ ≤ 1 nM As can be seen from the $IC_{50}$ value of compounds of above examples, compounds of the examples may inhibit proliferation of human breast cancer MCF-7 cells at extremely low concentrations. Some of compounds had a higher $IC_{50}$ ($IC_{50}$ value in the range of ++++ to +++++) activity than known SERD molecules (Cancer Research, 2016, 76: 3307).

It was shown from the above experimental results involving the degradation of estrogen receptors in MCF-7 and the inhibitory effects on growth of MCF-7 cells that the compounds of the present invention can effectively degrade estrogen receptors and inhibit the proliferation of human breast cancer MCF-7 cells and thus they can be used for the treatment or prevention of various diseases associated with estrogen by degrading estrogen receptor, such as cancer (breast cancer, ovarian cancer, colorectal cancer, prostate cancer, endometrial cancer), osteoporosis, neurodegenerative diseases, cardiovascular diseases, insulin resistance, lupus erythematosus, endometriosis, and obesity.

While embodiments of the present invention have been illustrated and described, it is not intended that all possible embodiments of the invention have been illustrated and described. Rather, the words used in the specification are merely illustrative and not restrictive, and it shall be understood that various changes may be made without departing from the spirit and scope of the invention.

The invention claimed is:
1. A compound of Formula I,

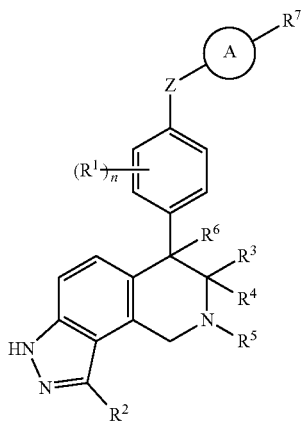

or an isotopically labeled compound thereof, or an optical isomer thereof, a geometric isomer thereof, a tautomer thereof or a mixture of various isomers, or a pharmaceutically acceptable salt thereof, or a prodrug thereof, in which
$R^1$ and $R^2$ are each independently selected from the group consisting of hydrogen, halo, cyano, C1 to C4 alkyl and substituted alkyl;
n is 1, 2, 3, or 4;
$R^3$, $R^4$, $R^6$ are each independently selected from the group consisting of hydrogen, C1 to C6 alkyl and substituted alkyl, aryl and heteroaryl;
$R^5$ is selected from the group consisting of C1 to C6 alkyl and substituted alkyl, aryl and heteroaryl;
$R^7$ is selected from the group consisting of C1 to C6 alkyl and substituted alkyl, C2 to C6 alkenyl and substituted alkenyl, C2 to C6 alkynyl and substituted alkynyl, and acyl having 1 to 6 carbon atoms;
Z is selected from the group consisting of O, S, C(=O), C ($R^9$)($R^{10}$), wherein, $R^9$ and $R^{10}$ are each independently selected from hydrogen, C1 to C6 alkyl and substituted alkyl;
A is a saturated four to six membered ring, which is a full carbocyclic ring or a heterocyclic ring containing one oxygen atom, one nitrogen atom, or two nitrogen atoms as ring atoms.

2. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein Z is selected from the group consisting of O, S, NH, C(=O), and $CH_2$.

3. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein Z is selected from O, S and NH.

4. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^6$ is selected from the group consisting of hydrogen, C1 to C4 alkyl and substituted C1 to C4 alkyl and $R^5$ is selected from the group consisting of C1 to C4 alkyl and substituted C1 to C4 alkyl.

5. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^6$ is hydrogen, or methyl and $R^5$ is methyl.

6. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^7$ is selected from the group consisting of C1 to C6 alkyl, substituted C1 to C6 alkyl, and acyl having 1 to 6 carbon atoms.

7. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^7$ is selected from the group consisting of propyl, butyl, pentyl, formyl, acetyl, propanoyl, butyryl, fluoro or difluoro propyl, and fluoro or difluoro butyl.

8. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^2$ is hydrogen or C1 to C4 alkyl.

9. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^3$ and $R^4$ are each independently selected from the group consisting of hydrogen, C1 to C4 alkyl, and substituted C1 to C4 alkyl.

10. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein one of $R^3$ and $R^4$ is hydrogen and the other is isobutyl or cyclopropylmethyl.

11. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^1$ is hydrogen or halogen and n is 1 or 2.

12. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein $R^1$ is hydrogen or F and n is 1 or 2.

13. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein A is a saturated four-membered carbocyclic ring or is a four-membered heterocyclic ring containing one oxygen atom, one nitrogen atom or two nitrogen atoms as ring atoms.

14. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein A is an azetidine ring.

15. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein the substituted alkyl is alkyl substituted with halogen.

16. The compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, wherein the substituted alkyl is alkyl substituted with one or two F.

17. A compound of Formula I, or an isotopically labeled compound thereof, or an optical isomer thereof, a geometric isomer thereof, a tautomer thereof or a mixture of various isomers, or a pharmaceutically acceptable salt thereof, or a prodrug thereof, wherein the compound is selected from the group consisting of:

1-(3-fluoropropyl)-N-(4-((6R, 7S)-7-isobutyl-8-methyl-6,7,8,9-tetrahydro-3H-pyrazolo [3,4-h] isoquinolin-6-yl) phenyl) azetidin-3-amine;

N-(3,5-difluoro-4-((6S, 7S)-7-isobutyl-8-methyl-6,7,8,9-tetrahydro-3H-pyrazolo [3,4 h] isoquinolin-6-yl) phenyl)-1-(3-fluoropropyl) azetidin-3-amine;

N-(3,5-difluoro-4-((6S, 7S)-7-isobutyl-8-methyl-6,7,8,9-tetrahydro-3H-pyrazolo [3,4 h] isoquinolin-6-yl) phenyl)-1-(2,3-difluoropropyl) azetidin-3-amine;

N-(3,5-difluoro-4-((6S, 7S)-7-isobutyl-8-methyl-6,7,8,9-tetrahydro-3H-pyrazolo [3,4-h] isoquinolin-6-yl) phenyl)-1-(3,3,3-trifluoropropyl) azetidin-3-amine;

N-(4-((6S, 7S)-7-cyclopropylmethyl-8-methyl-6,7,8,9-tetrahydro-3H-pyrazolo [3,4-h] isoquinolin-6-yl)-3,5-difluorophenyl)-1-(3-fluoropropyl) azetidin-3-amine;

N-(3,5-difluoro-4-((6S, 7S)-7-isobutyl-8-methyl-6,7,8,9-tetrahydro-3H-pyrazolo [3,4-h] isoquinolin-6-yl) phenyl)-1-propylazetidin-3-amine;

1-butyl-N-(3,5-difluoro-4-((6S, 7S)-7-isobutyl-8-methyl-6,7,8,9-tetrahydro-3H-pyrazolo [3,4-h] isoquinolin-6-yl) phenyl) azetidin-3-amine;

N-(3,5-difluoro-4-((6S, 7S)-7-isobutyl-8-methyl-6,7,8,9-tetrahydro-3H-pyrazolo [3,4-h] isoquinolin-6-yl) phenyl)-1-isobutylazetidin-3-amine;

N-(3,5-difluoro-4-((6S, 7S)-7-isobutyl-8-methyl-6,7,8,9-tetrahydro-3H-pyrazolo [3,4-h] isoquinolin-6-yl) phenyl)-1-pentylazetidin-3-amine;

(6S, 7S)-6-(2,6-difluoro-4-((1-(3-fluoropropyl) azetidin-3-yl) thio) phenyl)-7-isobutyl-8-methyl-6,7,8,9-tetrahydro-3H-pyrazolo [3,4-h] isoquinoline;

(6S, 7S)-6-(2,6-difluoro-4-((1-propyl) azetidin-3-yl) thio) phenyl)-7-isobutyl-8-methyl-6,7,8,9-tetrahydro-3H-pyrazolo [3,4-h] isoquinoline;

(6S, 7S)-6-(4-((1-butylazetidin-3-yl) thio)-2,6-difluorophenyl)-7-isobutyl-8-methyl-6,7,8,9-tetrahydro-3H-pyrazolo [3,4-h] isoquinoline;

(6S, 7S)-6-(2,6-difluoro-4-((1-isobutylazetidin-3-yl) thio) phenyl)-7-isobutyl-8-methyl-6,7,8,9-tetrahydro-3H-pyrazolo [3,4-h] isoquinoline;

(6S, 7S)-6-(2,6-difluoro-4-((1-pentylazetidin-3-yl) thio) phenyl)-7-isobutyl-8-methyl-6,7,8,9-tetrahydro-3H-pyrazolo [3,4-h] isoquinoline;

(6S, 7S)-6-(2,6-difluoro-4-((1-(3-fluoropropyl) azetidin-3-yl) oxy) phenyl)-7-isobutyl-8-methyl-6,7,8,9-tetrahydro-3H-pyrazolo [3,4-h] isoquinoline;

(6S, 7S)-6-(2,6-difluoro-4-((1-propylazetidin-3-yl) oxy) phenyl)-7-isobutyl-8-methyl-6,7,8,9-tetrahydro-3H-pyrazolo [3,4-h] isoquinoline;

(6S, 7S)-6-(2,6-difluoro-4-((1-isobutylazetidin-3-yl) oxy) phenyl)-7-isobutyl-8-methyl-6,7,8,9-tetrahydro-3H-pyrazolo [3,4-h] isoquinoline;

(6S, 7S)-6-(4-((1-butylazetidin-3-yl) oxy) phenyl)-7-isobutyl-8-methyl-6,7,8,9-tetrahydro-3H-pyrazolo [3,4-h] isoquinoline;

(6S, 7S)-6-(4-((1-pentylazetidin-3-yl) oxy) phenyl)-7-isobutyl-8-methyl-6,7,8,9-tetrahydro-3H-pyrazolo [3,4-h] isoquinoline;

(6S, 7S)-7-(cyclopropylmethyl)-6-(2,6-difluoro-4-((1-(3-fluoropropyl) azetidin-3-yl) oxy) phenyl)-8-methyl-6,7,8,9-tetrahydro-3H-pyrazolo [3,4-h] isoquinoline;

(6S, 7S)-7-cyclopropylmethyl-6-(2,6-difluoro-4-((1-propylazetidin-3-yl) oxy) phenyl)-8-methyl-6,7,8,9-tetrahydro-3H-pyrazolo [3,4-h] isoquinoline;

(6S, 7S)-7-cyclopropylmethyl-6-(2,6-difluoro-4-((1-isobutylazetidin-3-yl) oxy) phenyl)-8-methyl-6,7,8,9-tetrahydro-3H-pyrazolo [3,4-h] isoquinoline;

(6S, 7S)-6-(4-((1-butylazetidin-3-yl) oxy)-2,6-difluorophenyl)-7-cyclopropylmethyl-8-methyl-6,7,8,9-tetrahydro-3H-pyrazolo [3,4-h] isoquinoline;

(6S, 7S)-7-cyclopropylmethyl-6-(2,6-difluoro-4-((1-pentylazetidin-3-yl) oxy) phenyl)-8-methyl-6,7,8,9-tetrahydro-3H-pyrazolo [3,4-h] isoquinoline;

(6S, 7S)-7-cyclopropylmethyl-6-(2,6-difluoro-4-((1-(3-fluoropropyl) azetidin-3-yl) thio) phenyl)-8-methyl-6,7,8,9-tetrahydro-3H-pyrazolo [3,4-h] isoquinoline;

(6S, 7S)-7-cyclopropylmethyl-6-(2,6-difluoro-4-((1-propylazetidin-3-yl) thio) phenyl)-8-methyl-6,7,8,9-tetrahydro-3H-pyrazolo [3,4-h] isoquinoline;

(6S, 7S)-6-(4-((1-butylazetidin-3-yl) thio)-2,6-difluorophenyl)-7-cyclopropylmethyl-8-methyl-6,7,8,9-tetrahydro-3H-pyrazolo [3,4-h] isoquinoline;

(6S, 7S)-6-(4-((1-isobutylazetidin-3-yl) thio)-2,6-difluorobenzene)-7-cyclopropylmethyl-8-methyl-6,7,8,9-tetrahydro-3H-pyrazolo [3,4-h] isoquinoline;

(6S, 7S)-7-cyclopropylmethyl-6-(2,6-difluoro-4-((1-pentylazetidin-3-yl) thio) phenyl)-8-methyl-6,7,8,9-tetrahydro-3H-pyrazolo [3,4-h] isoquinoline;

3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-aldehyde;

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) ethan-1-one;

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) propan-1-one;

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl) butan-1-one;

1-(3-(3,5-difluoro-4-((6S, 7S)-7-isobutyl-8-methyl-6,7,8,9-tetrahydro-3H-pyrazolo [3,4-h] isoquinolin-6-yl) phenoxy) azetidin-1-yl)-2-methylpropan-1-one.

18. A pharmaceutical composition comprising a compound of formula I, or an isotopically labeled compound thereof, or an optical isomer thereof, a geometric isomer thereof, a tautomer thereof or a mixture of various isomers, or a pharmaceutically acceptable salt thereof, or a prodrug thereof according to claim 1, and one or more pharmaceutically acceptable carriers, adjuvants or excipients.

* * * * *

UNITED STATES PATENT AND TRADEMARK OFFICE
CERTIFICATE OF CORRECTION

Page 1 of 2

PATENT NO. : 11,236,088 B2
APPLICATION NO. : 16/762478
DATED : February 1, 2022
INVENTOR(S) : Dong Liu It is certified that error appears in the above-identified patent and that said Letters Patent is hereby corrected as shown below:

In the Specification

In Column 17 and 18, please change " 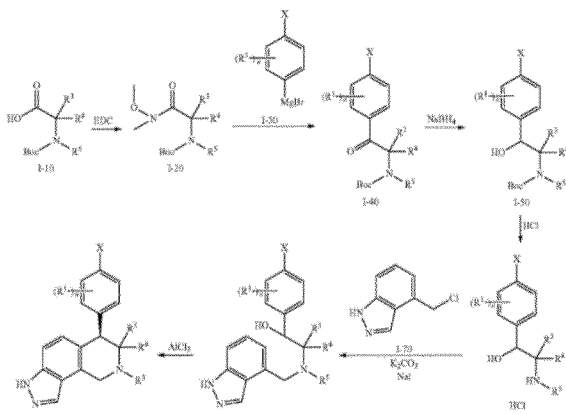 " to

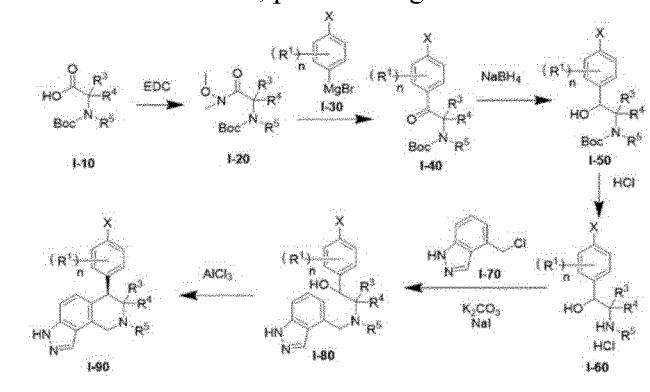

--

In Column 17, Line 42, please change "affortWeinreb" to --afford Weinreb--

In Column 17, Line 45, please change "affort" to --afford--

Signed and Sealed this
Tenth Day of May, 2022

Katherine Kelly Vidal
*Director of the United States Patent and Trademark Office*

CERTIFICATE OF CORRECTION (continued)
U.S. Pat. No. 11,236,088 B2

In Column 18, Line 36, please change "affort" to --afford--

In Column 18, Line 38, please change "affort" to --afford--

In Column 19, Line 58, please change "affort" to --afford--

In Column 19, Line 63, please change "affort" to --afford--

In Column 21, Line 41, please change "affort" to --afford--

In Column 25, Line 14, please change "affort" to --afford--

In Column 80, Line 55, please change "preventation" to --prevention--